United States Patent
Zhao et al.

(10) Patent No.: US 10,106,824 B2
(45) Date of Patent: Oct. 23, 2018

(54) PRODUCTION OF XYLITOL FROM A MIXTURE OF HEMICELLULOSIC SUGARS

(75) Inventors: Huimin Zhao, Champaign, IL (US); Nikhil Unni Nair, Urbana, IL (US); Michael Racine, Peoria, IL (US); Ryan Woodyer, Normal, IL (US)

(73) Assignees: The Board of Trustees of the University of Illinois, Urbana, IL (US); ZuChem, Inc., Chicago, IL (US)

(*) Notice: Subject to any disclaimer, the term of this patent is extended or adjusted under 35 U.S.C. 154(b) by 0 days.

(21) Appl. No.: 13/521,366

(22) PCT Filed: Jan. 14, 2011

(86) PCT No.: PCT/US2011/021277
§ 371 (c)(1),
(2), (4) Date: Jul. 10, 2012

(87) PCT Pub. No.: WO2011/088302
PCT Pub. Date: Jul. 21, 2011

(65) Prior Publication Data
US 2013/0065288 A1  Mar. 14, 2013

Related U.S. Application Data

(60) Provisional application No. 61/295,551, filed on Jan. 15, 2010, provisional application No. 61/328,609, filed on Apr. 27, 2010, provisional application No. 61/391,951, filed on Oct. 11, 2010.

(51) Int. Cl.
*C12P 7/18* (2006.01)

(52) U.S. Cl.
CPC ................. *C12P 7/18* (2013.01)

(58) Field of Classification Search
CPC .. C12P 7/10; C12P 19/14; C12P 19/02; C12P 7/18; C12P 7/065; C12P 7/08; C12P 2201/00; C12P 7/04; C12P 7/00; C12N 9/0006; C12N 9/2437; C12N 9/0004; C12Y 101/01009
See application file for complete search history.

(56) References Cited

U.S. PATENT DOCUMENTS

| 8,822,661 | B2 | 9/2014 | Zhao |
| 2004/0014185 | A1 | 1/2004 | Ojamo et al. |
| 2006/0035353 | A1 | 2/2006 | Zhao et al. |
| 2006/0110809 | A1 | 5/2006 | Taylor et al. |
| 2011/0159560 | A1* | 6/2011 | Donaldson ............ C12N 15/01 435/165 |
| 2013/0065288 | A1 | 3/2013 | Zhao et al. |
| 2013/0217070 | A1 | 8/2013 | Zhao et al. |

FOREIGN PATENT DOCUMENTS

| WO | WO 2009/009668 | 1/2009 |
| WO | 11/088302 | 7/2011 |

OTHER PUBLICATIONS

Liaw et al. Xylitol Production from Rice Straw Hemicellulose Hydrolyzate by Polyacrylic Hydrogel Thin Films with Immobilized Candida subtropicalis WF79, Journal of Bioscience and Bioengineering, vol. 105, Issue 2, Feb. 2008, pp. 97-105.*
Hong et al., "Cloning, overexpression, purification, and site-directed mutagenesis of xylitol-2-dehydrogenase from Candida albicans," *J. Mol. Catalysis B: Enzymatic*, 62: 40-45 (2009).
Nair et al, "Evolution in reverse: Engineering a D-Xylose-specific xylose reductase," *Chembiochem*, 9: 1213-1214 (2008).
Nair et al., Selective production of xylitol from hemicellulosic sugars using a combined protein and metabolic engineering approach, *AICHE 2009 Annual meeting*, Nashville, TN, (retrieved May 3, 2011 from the Internet: URL:chbe.illinois.edu/grad_symp/abstracts09/NairNikhil.pdf ) p. 1 (2009).
Nair et al. "Selective reduction of xylose to xylitol from a mixture of hemicellulosic sugars," *Metab. Engineer.*, 12(4): 462-468 (2010).
N. N., "Optimization of strains and fermentation processes for xylose production," *Northern Reg. Res. Cntr., CRIS* (Retrieved May 3, 2011 from the Internet: URL:www.reels.usda.gov/web/crisprojectpages/416503.html) p. 1-2 (2009).
Zhao, "Microbial synthesis of phloroglucinol and xylitol," (Retrieved May 3, 2011 from the Internet: URL:www.bio.org/ind/wc/08/breakout_pdfs/20080430/Track3_ContinentalC/Session8_1045am_1215pm/Zhao_Continental_C_Wed.pdf), 19-22 (2008).
Search Report and Written Opinion issued in App. No. PCT/US2011/021277 (2011).
Liaw et al., "Xylitol Production from Rice Straw Hemicellulose Hydrolyzate by Polyacrylic Hydrogel Thin Films with Immobilized Candida subtropicalis WF79", Journal of Bioscience and Bioengineering, vol. 105, Issue 2, 97-105 (2008).
Khankal et al., "Role of xylose transporters in xylitol production from engineered *Escherichia coli*", Journal of Biotechnology, 134:246-252 (2008).
N.N., "Optimization of strains and fermentation processes for xylose production", Northern Reg. Res. Cntr., CRIS (Retrieved May 3, 2011 from the Internet: URL:www.reels.usda.gov/web/crisporjectpages/416503.hmtl) p. 1-2 (2011).
Wen et al., "Protein engineering in deisgning tailored enzymes and microorganisms for biofuels production", Current Opinion in Biotechnology, 20:412-419 (2009).
Nair, "Synergy of protein and genome engineering for fuels and chemicals production", University of Illinois at Urbana-Champaign, Dissertation, 2010.
Sakakibara et al., "Microbial production of xylitol from L-arabinose by metabolically engineered *Escherichia coli*", Journal of Bioscience and Bioengineering, 107:506-511 (2009).

(Continued)

*Primary Examiner* — Iqbal H Chowdhury
(74) *Attorney, Agent, or Firm* — McDonnell Boehnen Hulbert & Berghoff LLP

(57) ABSTRACT

Materials and methods are described to produce xylitol from a mixture of hemicellulosic sugars by several routes. Examples include either as a direct co-product of a biorefinery or ethanol facility, or as a stand-alone product produced from an agricultural or forestry biomass feedstock including using, e.g. ethanol waste streams.

18 Claims, 35 Drawing Sheets

Specification includes a Sequence Listing.

(56) References Cited

OTHER PUBLICATIONS

Yoon et al., "L-arabinose pathway engineering for arabitol-free xylitol production in Candida tropicalis", Biotechnology Letters, 33:747-753 (2010).
Office Action for U.S. Appl. No. 13/877,803, dated Apr. 6, 2016.
Office Action for U.S. Appl. No. 13/877,803, dated Sep. 17, 2015.
Office Action for U.S. Appl. No. 13/877,803, dated Feb. 23, 2015.
Office Action for U.S. Appl. No. 13/877,803, dated Jul. 24, 2014.
Carvalheiro et al., "Hemicellulose biorefineries: a review on biomass pretreatments", Journal of Scientific & Industrial Research, 67:849-864 (2008).
N.N., "Optimization of strains and fermentation processes for xylose production", Northern Reg. Res. Cntr., CRIS (Retrieved May 3, 2011 from the Internet: URL:www.reels.usda.gov/web/crisprojectpages/416503.hmtl) p. 1-2 (published Jun. 9, 2010).

* cited by examiner

A
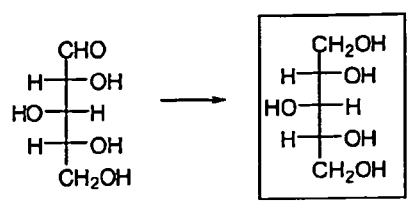
B
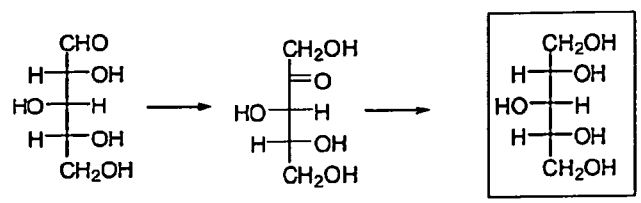
C
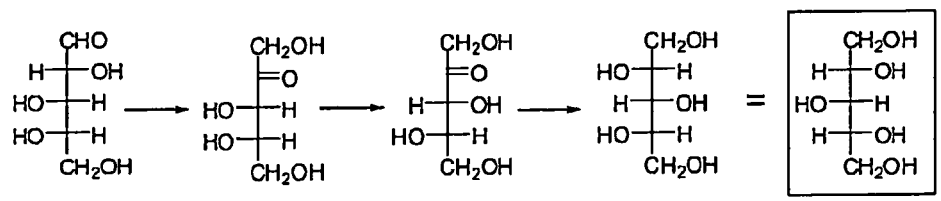
FIG. 1

A
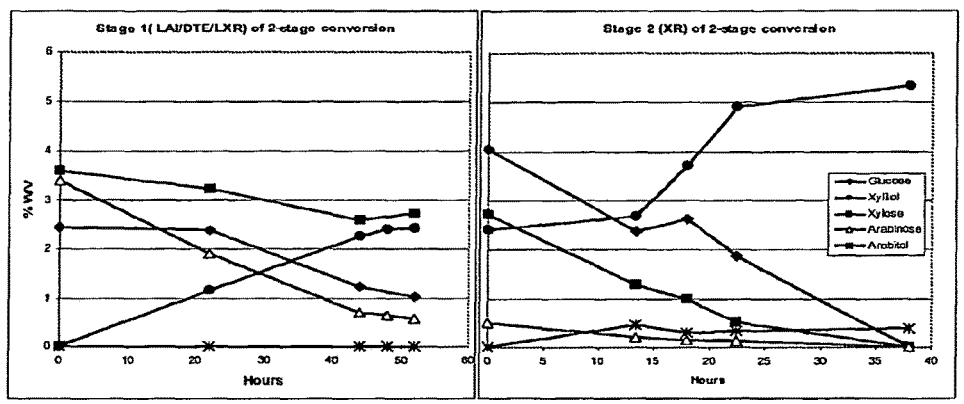
B
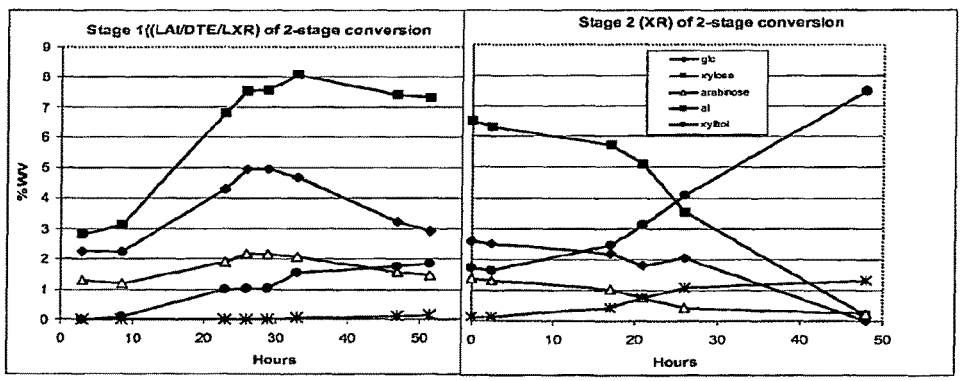
FIG. 5

SEQUENCE. Gene Sequence of Xylose reductase from Chaetomium globosum

An unannotated gene XM_001221042.1 (listed as hypothetical protein) was identified by BLAST search using known xylose reductase sequences. The predicted protein sequence of this gene is:

"MAPVIKLNSGYDMPQVGFGLWKVDNAVASDVVYNAIKAGYRLFDGACDYGNEVECGQGVARAISEGIVK
REDLFIVSKLWNTFHDAERVEPIVKKQLADWGIEYFDLYLIHFPVALEWVDPAVRYPPGWHYDGKEEIRP
SKATIQETWTALESLVSKGLSKSIGISNFQAQLIYDLLRYAKIRPATLQVEHHPYLVQQELINLAKREGI
AVTAYSSFGPASFKEFNMKHADALAPLIEDETIKKIAAKHNRPASQVLLRWATQRGLAIIPKSTRPQIMA
ENFQSIDFDLSEEDIATISAFDRGIRFNQPSNYFPTELLWIFG" (SEQ ID NO: 1)

A gene was synthetically constructed with optimized sequence for *E. coli* expression with the following DNA sequence:

atggcgccggtgattaaactgaacagcggctatgatatgccgcaggtgggctttggcctgtggaaagtgg
ataacgcggtggcgagcgatgtggtgtataacgcgattaaagcgggctatcgtctgtttgatggcgcgtg
cgattatggcaacgaagtggaatgcggccagggtgtggcgcgtgccatcagcgaaggcattgtgaaacgt
gaggacctgttcattgtgagcaaactgtggaacacctttcatgatgcggaacgtgtggaaccgattgtga
aaaaacagctggccgattggggcattgaatatttcgatctgtatctgatccatttccggtggcgctgga
atgggttgatccggcggtgcgttatccgccgggttggcattatgatggcaaagaagaaattcgtccgagc
aaagcgaccattcaggaaacctggaccgcgctggaaagcctggtgagcaaaggcctgagcaaaagcattg
gcattagcaactttcaggcgcagctgatttatgatctgctgcgctatgcgaaaattcgtccggcgaccct
gcaggtggaacatcatccgtatctggtgcagcaggaactgattaacctggccaaacgtgaaggcattgcg
gtgaccgcgtatagcagcttggtccggccagctttaaagaatttaacatgaaacatgcggatgcgctgg
ccccgctgattgaagatgaaaccatcaaaaaaatcgcggcgaaacataaccgtccggcgagccaggttct
gctgcgttgggcgacccagcgtggcctggccattattccgaaaagcacccgtccgcagattatggcggaa
aactttcagagcatcgatttgatctgagcgaagaagatattgcgaccattagcgcgtttgatcgtggca
ttcgtttttaaccagccgagcaactatttccgaccgaactgctgtggattttggctaa (SEQ ID NO: 2)

This gene was placed in the expression vector pTRP200 under the pTRP promoter allowing constitutive expression.

FIG. 16

NcXR wt atggttcctgctatcaagctcaactccggcttcgacatgccccaggtcggcttcggcctctggaaggtcg
acggctccatcgcttccgatgtcgtctacaacgctatcaaggcaggctaccgcctcttcgatggtgcctg
cgactacggcaacgaggttgagtgcggccagggtgtagcccgcgccatcaaggagggcatcgtcaagcgc
gaggagctctttatcgtctccaagctctggaacaccttccacgacggcgaccgcgtcgagcccatcgtcc
gcaagcagcttgccgactggggtctcgagtacttcgatctctacctgatccacttccccgtcgccctcga
gtacgtcgacccctcggtccgttaccctcccggctggcactttgacggcaagagcgagatccgcccctcc
aaggccaccatccaagagacctggacggccatggagtcgctcgtcgagaagggtctctccaagagcattg
gcgtctccaacttccaggcccagctcctgtacgacctcctccgctacgccaaggtccgccccgccactct
ccagatcgagcaccacccctacctcgtccagcagaacctcctcaaccttgccaaggctgagggcatcgcc
gtgaccgcctactcctccttcggccctgcttctttccgcgagttcaacatggagcacgcccagaagctcc
agcctctcctcgaggaccccaccatcaaggctattggtgacaagtacaacaaggatcctgcccaggtcct
cctccgttgggccacccagcgcggcctggccatcatccccaagtctagccgcgaggccaccatgaagtcc
aacctcaactctcttgatttcgatctctccgaggaggacatcaagaccatctctggtttcgaccgcggca
tccgcttcaaccagcccaccaactacttctccgctgagaacctctggattttcggttag (SEQ ID
NO: 3)

MVPAIKLNSGFDMPQVGFGL
WKVDGSIASDVVYNAIKAGY
RLFDGACDYGNEVECGQGVA
RAIKEGIVKREELFIVSKLW
NTFHDGDRVEPIVRKQLADW
GLEYFDLYLIHFPVALEYVD
PSVRYPPGWHFDGKSEIRPS
KATIQETWTAMESLVEKGLS
KSIGVSNFQAQLLYDLLRYA
KVRPATLQIEHHPYLVQQNL
LNLAKAEGIAVTAYSSFGPA
SFREFNMEHAQKLQPLLEDP
TIKAIGDKYNKDPAQVLLRW
ATQRGLAIIPKSSREATMKS
NLNSLDFDLSEEDIKTISGF
DRGIRFNQPTNYFSAENLWI
FG* (SEQ ID NO: 4)

FIG. 18 pACYC-ncxr ggggaattgtgagcggataacaattcccctgtagaaataattttgtttaacttaataaggagatataccatgggcag
cagccatcaccatcatcaccacagccaggatccgaattcgatggttcctgctatcaagctcaactccggcttcgacat
gccccaggtcggcttcggcctctggaaggtcgacggctccatcgcttccgatgtcgtctacaacgctatcaaggcagg
ctaccgcctcttcgatggtgcctgcgactacggcaacgaggttgagtgcggccagggtgtagcccgcgccatcaagga
gggcatcgtcaagcgcgaggagctcttatcgtctccaagctctggaacaccttccacgacggcgaccgcgtcgagcc
catcgtccgcaagcagcttgccgactgggtctcgagtacttcgatctctacctgatccacttcccgtcgccctcga
gtacgtcgacccctcggtccgttaccctcccggctggcactttgacggcaagagcgagatccgcccctccaaggccac
catccaagagacctggacggccatggagtcgctcgtcgagaagggtctctccaagagcattggcgtctccaacttcca
ggcccagctcctgtacgacctcctccgctacgccaaggtccgccccgccactctccagatcgagcaccaccctacct
cgtccagcagaacctcctcaaccttgccaaggctgagggcatcgccgtgaccgcctactcctccttcggccctgcttc
tttccgcgagttcaacatggagcacgcccagaagctccagcctctcctcgaggacccccaccatcaaggctattggtga
caagtacaacaaggatcctgcccaggtcctcctccgttgggccacccagcgcggcctggccatcatccccaagtctag
ccgcgaggccaccatgaagtccaacctcaactctcttgatttcgatctctccgaggaggacatcaagaccatctctgg
tttcgaccgcggcatccgcttcaaccagcccaccaactacttctccgctgagaacctctggattttcggttagagatc
tcaattggatatcggccggccacgcgatcgctgacgtcggtaccctcgagtctggtaaagaaaccgctgctgcgaaat
ttgaacgccagcacatggactcgtctactagcgcagcttaattaacctaggctgctgccaccgctgagcaataactag
cataacccttgggccctctaaacgggtcttgagggtttttgctgaaacctcaggcatttgagaagcacacggtca
cactgcttccggtagtcaataaaccggtaaaccagcaatagacataagcggctatttaacgaccctgccctgaaccga
cgaccgggtcgaatttgctttcgaatttctgccattcatccgcttattatcacttattcaggcgtagcaccaggcgtt
taagggcaccaataactgccttaaaaaaaattacgccccgccctgccactcatcgcagtactgttgtaattcattaagc
attctgccgacatggaagccatcacagacggcatgatgaacctgaatcgccagcggcatcagcaccttgtcgccttgc
gtataatatttccccatagtgaaaacgggggcgaagaagttgtccatattggccacgtttaaatcaaaactggtgaaa
ctcacccagggattggctgagacgaaaaacatattctcaataaacccttaggggaaataggccaggttttccaccgtaa
cacgccacatcttgcgaatatatgtgtagaaactgccggaaatcgtcgtggtattcactccagagcgatgaaaacgtt
tcagtttgctcatggaaaacggtgtaacaagggtgaacactatcccatatccaccagctcaccgtctttcattgccata
cggaactccggatgagcattcatcaggcgggcaagaatgtgaataaaggccggataaaacttgtgcttatttttcttt
acggtctttaaaaaggccgtaatatccagctgaacggtctggttataggtacattgagcaactgactgaaatgcctca
aaatgttcttacgatgccattgggatatatcaacggtggtatatccagtgattttttctccattttagcttcctta
gctcctgaaaatctcgataactcaaaaaatacgcccggtagtgatcttatttcattatggtgaaagttggaacctctt
acgtgccgatcaacgtctcattttcgccaaaagttggcccaggggcttcccggtatcaacagggacaccaggatttatt
tattctgcgaagtgatcttccgtcacaggtatttattcggcgcaaagtgcgtcgggtgatgctgccaacttactgatt
tagtgtatgatggtgttttgaggtgctccagtggcttctgtttctatcagctgtccctcctgttcagctactgacgg
ggtggtgcgtaacggcaaaagcaccgccggacatcagcgctagcggagtgtatactggcttactatgttggcactgat
gagggtgtcagtgaagtgcttcatgtggcaggagaaaaaaggctgcaccggtgcgtcagcagaatatgtgatacagga
tatattccgcttcctcgctcactgactcgctacgctcggtcgttcgactgcggcgagcggaaatggcttacgaacggg
gcggagatttcctggaagatgccaggaagatacttaacagggaagtgagagggccgcggcaaagccgttttccatag
gctccgccccctgacaagcatcacgaaatctgacgctcaaatcagtggtggcgaaacccgacaggactataaagata
ccaggcgtttcccctggcggctccctcgtgcgctctcctgttcctgccttcggtttaccggtgtcattccgctgtta
tggccgcgtttgtctcattccacgcctgacactcagttccgggtaggcagttcgctccaagctggactgtatgcacga
accccccgttcagtccgaccgctgcgccttatccggtaactatcgtcttgagtccaacccgaaagacatgcaaaagc
accactggcagcagccactggtaattgatttagaggagtagtcttgaagtcatgcgccggttaaggctaaactgaaa
ggacaagtttggtgactgcgctcctccaagccagttacctcggttcaaagagttggtagctcagagaaccttcgaaa
aaccgccctgcaaggcggttttttcgttttcagagcaagagattacgcgcagaccaaaacgatctcaagaagatcatc
ttattaatcagataaaatatttctagatttcagtgcaatttatctcttcaaatgtagcacctgaagtcagcccccatac
gatataagttgtaattctcatgttagtcatgccccgcgcccaccggaaggagctgactgggttgaaggctctcaaggg
catcggtcgagatcccggtgcctaatgagtgagctaacttacattaattgcgttgcgctcactgcccgctttccagtc
gggaaacctgtcgtgccagctgcattaatgaatcggccaacgcgcgggagagggcggtttgcgtattgggcgccaggg
tggttttctttcaccagtgagacgggcaacagctgattgcccttcaccgcctggccctgagagagttgcagcaagc
ggtccacgctgctttgcccagcaggcgaaaatcctgtttgatggtggttaacggcgggatataacatgagctgtctt
cggtatcgtcgtatcccactaccgagatgtccgcaccaacgcgcagcccggactcggtaatggcgcgcattgcgccca
gcgccatctgatcgttggaaccagcatcgcagtgggaacgatgccctcattcagcatttgcatggtttgttgaaaac
cggacatggcactccagtcgccttcccgttccgctatcggctgaatttgattgcgagtgagatatttatgccagccag
ccagacgcagacgcgccgagacagaacttaatgggcccgctaacagcgcgatttgctggtgacccaatgcgaccagat
gctccacgcccagtcgcgtaccgtcttcatgggagaaaaataatactgttgatgggtgtctggtcagagacatcaagaa
ataacgccggaacattagtgcaggcagcttccacagcaatggcatcctggtcatccagcggatagttaatgatcagcc
cactgacgcgttgcgcgagaagattgtgcaccgccgctttacaggcttcgacgccgcttcgttctaccatcgacacca
ccacgctggcaccagttgatcggcgcgagatttaatcgccgcgacaatttgcgacggcgcgtgcagggccagactgg
aggtggcaacgccaatcagcaacgactgtttgcccgccagttgttgtgccacgcggttgggaatgtaattcagctccg
ccatcgccgcttccacttttcccgcgttttcgcagaaacgtggctggcctggttcaccacgcgggaaacggtctgat
aagagacaccggcatactctgcgacatcgtataacgttactggtttcacattcaccaccctgaattgactctcttccg
ggcgctatcatgccataccgcgaaaggttttgcgccattcgatggtgtccgggatctcgacgctctcccttatgcgac
tcctgcattaggaaattaatacgactcactata (SEQ ID NO: 5)

FIG. 19 pXXR atgcatttccatttatttttgcgagcgagcgcacacttgtgaattatctcaatagcagtgtgaaataacataattgag
caactgaaagggagtgcccaatattacgacatcatccatcacccgcggcattacctgattatggttcctgctatcaag
ctcaactccggcttcgacatgccccaggtcggcttcggcctctggaaggtcgacaggctccatcgcttccgatgtcgtc
tacaacgctatcaaggcaggctaccgcctcttcgatggtgcctgcgactacggcaacgaggttgagtgcggccagggt
gtagcccgcgccatcaaggagggcatcgtcaagcgcgaggagctctttatcgtctccaagctctggaacaccttccac
gacggcgaccgcgtcgagccatcgtccgcaagcagcttgccgactggggtctcgagtacttcgatctctacctgatc
cacttcccgtcgccctcgagtacgtcgaccctcggtccgttaccctcccggctggcactttgacggcaagagcgag
atccgccctccaaggccaccatccaagagacctggacggccatggagtcgctcgtcgagaagggtctctccaagagc
attggcgtctccaacttccaggcccagctcctgtacgacctcctccgctacgccaaggtccgccccgccactctccag
atcgagcaccacccctacctcgtccagcagaacctcctcaaccttgccaaggctgagggcatcgccgtgaccgcctac
tcctccttcggccctgcttctttccgcgagttcaacatggagcacgcccagaagctccagcctctcctcgaggacccc
accatcaaggctattggtgacaagtacaacaaggatcctgcccaggtcctcctccgttgggcacccagcgcggcctg
gccatcatccccaagtctagccgcgcgaggccaccatgaagtccaacctcaactctcttgatttcgatctctccgaggag
gacatcaagaccatctctggtttcgaccgcggcatccgcttcaaccagcccaccaactacttctccgctgagaacctc
tggattttcggttagagatcctctagagtcgacctgcaggcatgcaagcttggctgttttggcggatgagagaagatt
ttcagcctgatacagattaaatcagaacgcagaagcggtctgataaaacagaatttgcctggcggcagtagcgcggtg
gtcccacctgacccatgccgaactcagaagtgaaacgccgtagcgcgatggtagtgtggggtctccccatgcgaga
gtagggaactgccaggcatcaaataaaacgaaaggctcagtcgaaagactgggcctttcgttttatctgttgtttgtc
ggtgaacgctctcctgagtaggacaaatccgccgggagcggatttgaacgttgcgaagcaacggcccggagggtggcg
ggcaggacgcccgccataaactgccaggcatgcaggcatcctgacggatggccttttttgcgtttct
acaaactcttttttgtttattttttctaaatacattcaaatatgtatccgctcatgagacaataaccctgataaatgctt
caataatattgaaaaggaagagtatgagtattcaacatttccgtgtcgcccttattccctttttgcggcattttgc
cttcctgttttgctcacccagaaacgctggtgaaagtaaaagatgctgaagatcagttgggtgcacgagtgggttac
atcgaactggatctcaacagcggtaagatccttgagagttttcgccccgaagaacgttttccaatgatgagcactttt
aaagttctgctatgtggcgcggtattatcccgtgttgacgccgggcaagagcaactcggtcgccgcatacactattct
cagaatgacttggttgagtactcaccagtcacagaaaagcatcttacggatggcatgacagtaagagaattatgcagt
gctgccataaccatgagtgataacactgcggccaacttacttctgacaacgatcggaggaccgaaggagctaaccgct
tttttgcacaacatgggggatcatgtaactcgccttgatcgttgggaaccggagctgaatgaagccataccaaacgac
gagcgtgacaccacgatgcctacagcaatggcaacaacgttgcgcaaactattaactggcgaactacttactctagct
tcccggcaacaattaatagactggatggaggcggataaagttgcaggaccacttctgcgctcggcccttccggctggc
tggtttattgctgataaatctggagccggtgagcgtgggtctcgcggtatcattgcagcactggggccagatggtaag
ccctcccgtatcgtagttatctacacgacgggagtcaggcaactatggatgaacgaaatagacagatcgctgagata
ggtgcctcactgattaagcattggtaactgtcagaccaagtttactcatatatactttagattgatttaaaacttcat
ttttaatttaaaaggatctaggtgaagatcctttttgataatctcatgaccaaaatcccttaacgtgagttttcgttc
cactgagcgtcagacccgtagaaaagatcaaaggatcttcttgagatcctttttttctgcgcgtaatctgctgcttg
caaacaaaaaaaccaccgctaccagcggtggtttgtttgccggatcaagagctaccaactctttttccgaaggtaact
ggcttcagcagagcgcagataccaaatactgtccttctagtgtagccgtagttaggccaccacttcaagaactctgta
gcaccgcctacatacctcgctctgctaatcctgttaccagtggctgctgccagtggcgataagtcgtgtcttaccggg
ttggactcaagacgatagttaccggataaggcgcagcggtcgggctgaacggggggttcgtgcacacagcccagcttg
gagcgaacgacctacaccgaactgagatacctacagcgtgagctatgagaaagcgccacgcttcccgaagggagaaag
gcggacaggtatccggtaagcggcagggtcggaacaggagagcgcacgagggagcttccaggggaaacgcctggtat
ctttatagtcctgtcgggtttcgccacctctgacttgagcgtcgatttttgtgatgctcgtcaggggggcggagccta
tggaaaaacgccagcaacgcggcctttttacggttcctggccttttgctggccttttgctcacatgttctttcctgcg
ttatccctgattctgtggataaccgtattaccgcctttgagtgagctgataccgctcgccgcagccgaacgaccgag
cgcagcgagtcagtgagcgaggaagcggaagagcgcctgatgcggtattttctccttacgcatctgtgcggtatttca
caccgcatatggtgcactctcagtacaatctgctctgatccgcatagttaagccagtatacactccgctatcgctac
gtgactgggtcatggctgcgcccgacacccgccaacacccgctgacgcgccctgacgggcttgtctgctcccggcat
ccgcttacagacaagctgtgaccgtctccgggagctgcatgtgtcagaggttttcaccgtcatcaccgaaacgcgcga
ggcagcagatcaattcgcgcgcgaaggcgaagcggc (SEQ ID NO: 6)

FIG. 20 pTrcXR gtttgacagcttatcatcgactgcacggtgcaccaatgcttctggcgtcaggcagccatcggaagctgtg
gtatggctgtgcaggtcgtaaatcactgcataattcgtgtcgctcaaggcgcactcccgttctggataat
gtttttttgcgccgacatcataacggttctggcaaatattctgaaatgagctgttgacaattaatcatccg
gctcgtataatgtgtggaattgtgagcggataacaatttcacacaggaaacagaccatggaattcgagct
cggtaccatggttcctgctatcaagctcaactccggcttcgacatgccccaggtcggcttcggcctctgg
aaggtcgacggctccatcgcttccgatgtcgtctacaacgctatcaaggcaggctaccgcctcttcgatg
gtgcctgcgactacggcaacgaggttgagtgcggccagggtgtagcccgcgccatcaaggagggcatcgt
caagcgcgaggagctctttatcgtctccaagctctggaacaccttccacgacggcgaccgcgtcgagccc
atcgtccgcaagcagcttgccgactgggtctcgagtacttcgatctctacctgatccacttccccgtcg
ccctcgagtacgtcgacccctcggtccgttaccctcccggctggcactttgacggcaagagcgagatccg
cccctccaaggccaccatccaagagacctggacggccatggagtcgctcgtcgagaagggtctctccaag
agcattggcgtctccaacttccaggcccagctcctgtacgacctcctccgctacgccaaggtccgcccg
ccactctccagatcgagcaccaccctacctcgtccagcagaacctcctcaaccttgccaaggctgaggg
catcgccgtgaccgcctactcctccttcggccctgcttctttccgcgagttcaacatggagcacgcccag
aagctccagcctctcctcgaggaccccaccatcaaggctattggtgacaagtacaacaaggatcctgccc
aggtcctcctccgttgggccacccagcgcggcctggccatcatccccaagtctagccgcgaggccaccat
gaagtccaacctcaactctcttgatttcgatctctccgaggaggacatcaagaccatctctggtttcgac
cgcggcatccgcttcaaccagccaccaactacttctccgctgagaacctctggatttcggttagagat
cctctagagtcgacctgcaggcatgcaagcttggctgttttggcggatgagagaagattttcagcctgat
acagattaaatcagaacgcagaagcggtctgataaaacagaatttgcctggcggcagtagcgcggtggtc
ccacctgacccatgccgaactcagaagtgaaacgccgtagcgccgatggtagtgtggggtctcccatg
cgagagtagggaactgccaggcatcaaataaaacgaaaggctcagtcgaaagactgggcctttcgtttta
tctgttgtttgtcggtgaacgctctcctgagtaggacaaatccgccgggagcggatttgaacgttgcgaa
gcaacggcccggagggtggcgggcaggacgcccgcataaaactgccaggcatcaaattaagcagaaggcc
atcctgacggatggcctttttgcgtttctacaaactcttttttgtttatttttctaaatacattcaaatat
gtatccgctcatgagacaataaccctgataaatgcttcaataatattgaaaaaggaagagtatgagtatt
caacatttccgtgtcgcccttattccctttttgcggcatttgccttcctgttttgctcacccagaaa
cgctggtgaaagtaaaagatgctgaagatcagttgggtgcacgagtgggttacatcgaactggatctcaa
cagcggtaagatccttgagagttttcgccccgaagaacgttttccaatgatgagcacttttaaagttctg
ctatgtggcgcggtattatcccgtgttgacgccgggcaagagcaactcggtcgccgcatacactattctc
agaatgacttggttgagtactcaccagtcacagaaaagcatcttacggatgcatgacagtaagagaatt
atgcagtgctgccataaccatgagtgataacactgcggccaacttacttctgacaacgatcggaggaccg
aaggagctaaccgcttttttgcacaacatgggggatcatgtaactcgccttgatcgttgggaaccggagc
tgaatgaagccataccaaacgacgagcgtgacaccacgatgcctacagcaatggcaacaacgttgcgcaa
actattaactggcgaactacttactctagcttcccggcaacaattaatagactggatgaggcggataaa
gttgcaggaccacttctgcgctcggcccttccggctggctggttattgctgataaatctggagccggtg
agcgtgggtctcgcggtatcattgcagcactggggccagatggtaagccctcccgtatcgtagttatcta
cacgacggggagtcaggcaactatggatgaacgaaatagacagatcgctgagataggtgcctcactgatt
aagcattggtaactgtcagaccaagtttactcatatatactttagattgatttaaaacttcattttttaat
ttaaaaggatctaggtgaagatcctttttgataatctcatgaccaaaatcccttaacgtgagttttcgtt
ccactgagcgtcagaccccgtagaaaagatcaaaggatcttcttgagatcctttttttctgcgcgtaatc
tgctgcttgcaaacaaaaaaaccaccgctaccagcggtggtttgtttgccggatcaagagctaccaactc
tttttccgaaggtaactggcttcagcagagcgcagataccaaatactgtccttctagtgtagccgtagtt
aggccaccacttcaagaactctgtagcaccgcctacatacctcgctctgctaatcctgttaccagtggct
gctgccagtggcgataagtcgtgtcttaccgggttggactcaagacgatagttaccggataaggcgcagc
ggtcgggctgaacggggggttcgtgcacacagcccagcttggagcgaacgacctacaccgaactgagata
cctacagcgtgagctatgagaaagcgccacgcttcccgaagggagaaaggcggacaggtatccggtaagc
ggcagggtcggaacaggagagcgcacgagggagcttccaggggaaacgcctggtatctttatagtcctg
tcgggtttcgccacctctgacttgagcgtcgatttttgtgatgctcgtcaggggggcggagcctatgaa
aaacgccagcaacgcggccttttacggttcctggccttttgctggccttttgctcacatgttctttcct
gcgttatcccctgattctgtggataaccgtattaccgcctttgagtgagctgataccgctcgccgcagcc
gaacgaccgagcgcagcgagtcagtgagcgaggaagcggaagagcgcctgatgcggtattttctccttac
gcatctgtgcggtatttcacaccgcatatggtgcactctcagtacaatctgctctgatgccgcatagtta

FIG. 21

```
agccagtatacactccgctatcgctacgtgactgggtcatggctgcgcccgacaccgccaacaccgc
tgacgcgccctgacgggcttgtctgctcccggcatccgcttacagacaagctgtgaccgtctccgggagc
tgcatgtgtcagaggttttcaccgtcatcaccgaaacgcgcgaggcagcagatcaattcgcgcgcgaagg
cgaagcggcatgcatttacgttgacaccatcgaatggtgcaaaacctttcgcggtatggcatgatagcgc
ccggaagagagtcaattcagggtggtgaatgtgaaaccagtaacgttatacgatgtcgcagagtatgccg
gtgtctcttatcagaccgtttcccgcgtggtgaaccaggccagccacgtttctgcgaaaacgcgggaaaa
agtggaagcggcgatggcggagctgaattacattcccaaccgcgtggcacaacaactggcgggcaaacag
tcgttgctgattggcgttgccacctccagtctggccctgcacgcgccgtcgcaaattgtcgcggcgatta
aatctcgcgccgatcaactgggtgccagcgtggtggtgtcgatggtagaacgaagcggcgtcgaagcctg
taaagcggcggtgcacaatcttctcgcgcaacgcgtcagtgggctgatcattaactatccgctggatgac
caggatgccattgctgtggaagctgcctgcactaatgttccggcgttatttcttgatgtctctgaccaga
cacccatcaacagtattattttctcccatgaagacggtacgcgactgggcgtggagcatctggtcgcatt
gggtcaccagcaaatcgcgctgttagcgggcccattaagttctgtctcggcgcgtctgcgtctggctggc
tggcataaatatctcactcgcaatcaaattcagccgatagcggaacgggaaggcgactggagtgccatgt
ccggttttcaacaaaccatgcaaatgctgaatgagggcatcgttcccactgcgatgctggttgccaacga
tcagatggcgctgggcgcaatgcgcgccattaccgagtccgggctgcgcgttggtgcggatatctcggta
gtgggatacgacgataccgaagacagctcatgttatatcccgccgtcaaccaccatcaaacaggattttc
gcctgctggggcaaaccagcgtggaccgcttgctgcaactctctcagggccaggcggtgaagggcaatca
gctgttgcccgtctcactggtgaaaagaaaaaccacctggcgcccaatacgcaaaccgcctctcccgc
gcgttggccgattcattaatgcagctggcacgacaggtttcccgactggaaagcgggcagtgagcgcaac
gcaattaatgtgagttagcgcgaattgatctg (SEQ ID NO: 7)
```

FIG. 21 (cont.)

pAraXR catatggttcctgctatcaagctcaactccggcttcgacatgccccaggtcggcttcggcctctggaaggtcgacggc
tccatcgcttccgatgtcgtctacaacgctatcaaggcaggctaccgcctcttcgatggtgcctgcgactacgcaac
gaggttgagtgcggccagggtgtagcccgcgccatcaaggagggcatcgtcaagcgcgaggagctctttatcgtctcc
aagctctggaacaccttccacgacggcgaccgcgtcgagcccatcgtccgcaagcagcttgccgactggggtctcgag
tacttcgatctctacctgatccacttccccgtcgccctcgagtacgtcgaccccctcggtccgttaccctcccggctgg
cactttgacggcaagagcgagatccgccctccaaggccaccatccaagagacctggacggccatggagtcgctcgtc
gagaagggtctctccaagagcattggcgtctccaacttccaggccagctcctgtacgacctcctccgctacgccaag
gtccgccccgccactctccagatcgagcaccaccccctacctcgtccagcagaacctcctcaaccttgccaaggctgag
ggcatcgccgtgaccgcctactcctccttcggccctgcttctttccgcgagttcaacatggagcacgcccagaagctc
cagcctctcctcgaggacccaccatcaaggctattggtgacaagtacaacaaggatcctgcccaggtcctcctccgt
tgggccacccagcgcggcctggccatcatcccccaagtctagccgcgaggccaccatgaagtccaacctcaactctctt
gatttcgatctctccgaggaggacatcaagaccatctctggtttcgaccgcggcatccgcttcaaccagcccaccaac
tacttctccgctgagaacctctggatttcggttagagatcctctagagtcgacctgcaggcatgcaagcttggctgt
tttggcggatgagaagatttcagcctgatacagattaaatcagaacgcagaagcggtctgataaaacagaatttg
cctggcggcagtagcgcggtggtcccacctgaccccatgccgaactcagaagtgaaacgccgtagcgccgatggtagt
gtggggtctccccatgcgagagtagggaactgccaggcatcaaataaaacgaaaggctcagtcgaaagactgggcctt
tcgttttatctgttgtttgtcggtgaacgctctcctgagtaggacaaatccgccgggagcggatttgaacgttgcgaa
gcaacggcccggagggtggcgggcaggacgccgccataaactgccaggcatcaaattaagcagaaggccatcctgac
ggatggccttttttgcgtttctacaaactcttttttgtttatttttctaaatacattcaaatatgtatccgctcatgaga
caataaccctgataaatgcttcaataattattgaaaaaggaagagtatgagtattcaacatttccgtgtcgcccttatt
ccctttttttgcggcattttttgccttcctgtttttgctcacccagaaacgctggtgaaagtaaaagatgctgaagatcag
ttgggtgcacgagtgggttacatcgaactggatctcaacagcggtaagatccttgagagtttttcgccccgaagaacgt
tttccaatgatgagcacttttaaagttctgctatgtggcgcggtattatcccgtgttgacgccgggcaagagcaactc
ggtcgccgcatacactattctcagaatgacttggttgagtactcaccagtcacagaaaagcatcttacggatggcatg
acagtaagagaattatgcagtgctgccataaccatgagtgataacactgcggccaacttacttctgacaacgatcgga
ggaccgaaggagctaaccgcttttttgcacaacatggggggatcatgtaactcgccttgatcgttgggaaccggagctg
aatgaagccataccaaacgacgagcgtgacaccacgatgcctacagcaatggcaacaacgttgcgcaaactattaact
ggcgaactacttactctagcttcccggcaacaattaatagactggatggaggcggataaagttgcaggaccacttctg
cgctcggcccttccggctggctggtttattgctgataaatctggagccggtgagcgtgggtctcgcggtatcattgca
gcactggggccagatggtaagccctcccgtatcgtagttatctacacgacggggagtcaggcaactatggatgaacga
aatagacagatcgctgagataggtgcctcactgattaagcattggtaactgtcagaccaagtttactcatatatactt
tagattgatttaaaacttcattttttaatttaaaaggatctaggtgaagatcctttttgataatctcatgaccaaaatc
ccttaacgtgagttttcgttccactgagcgtcagaccccgtagaaaagatcaaaggatcttcttgagatcctttttt
ctgcgcgtaatctgctgcttgcaaacaaaaaaaccaccgctaccagcggtggtttgtttgccggatcaagagctacca
actcttttttccgaaggtaactggcttcagcagagcgcagataccaaatactgtccttctagtgtagccgtagttaggc
caccacttcaagaactctgtagcaccgcctacatacctcgctctgctaatcctgttaccagtggctgctgccagtggc
gataagtcgtgtcttaccgggttggactcaagacgatagttaccggataaggcgcagcggtcgggctgaacgggggt
tcgtgcacacagcccagcttggagcgaacgacctacaccgaactgagatacctacagcgtgagctatgagaaagcgcc
acgcttcccgaagggagaaaggcggacaggtatccggtaagcggcagggtcggaacaggagagcgcacgagggagctt
ccagggggaaacgcctggtatctttatagtcctgtcgggtttcgccacctctgacttgagcgtcgatttttgtgatgc
tcgtcagggggcggagcctatggaaaaacgccagcaacgcggcctttttacggttcctggccttttgctggccttttt
gctcacatgttctttcctgcgttatcccctgattctgtggataaccgtattaccgcctttgagtgagctgataccgct
cgccgcagccgaacgaccgagcgcagcgagtcagtgagcgaggaagcggaagagcgcctgatgcggtattttctcctt
acgcatctgtgcggtatttcacaccgcatatggtgcactctcagtacaatctgctctgatgccgcatagttaagccag
tatacactccgctatcgctacgtgactgggtcatggctgcgccccgacacccgccaacacccgctgacgcgccctgac
gggcttgtctgctcccggcatccgcttacagacaagctgtgaccgtctccgggagctgcatgtgtcagaggttttcac
cgtcatcaccgaaacgcgcgaggcagcagatcaattcgcgcgcgaaggcgaagcggcatgcagcgccattcagagaag
aaaccaattgtccatattgcatcagacattgccgtcactgcgtcttttactggctcttctcgctaaccaaaccggtaa
ccccgcttattaaaagcattctgtaacaaagcgggaccaaggccatgacaaaaacgcgtagcaaaagtgtctataatc
acggcagaaaagtccacattgattatttgcacggcgtcacactttgctatgccatagcatttttatccataagattag
cggatcctacctgacgctttttatcgcaactctctactgtttctccataccgttttttgg (SEQ ID NO: 8)

FIG. 22

NcXR mutant S

Atggttcctgctatcaagctcaactccggcttcgacatgccccaggtcggcttcggcctctggaaggtcg
acggctccatcgcttccgatgtcgtctacaacgctatcaaggcaggctaccgcctcttcgatggtgcctg
cgactacggcaacgaggttgagtgcggccagggtgtagcccgcgccatcaaggagggcatcgtcaagcgc
gaggagctctttatcgtctccaagctctggaacaccttccacgacggcgaccgcgtcgagcccatcgtcc
gcaagcagcttgccgactggggtctcgagtacttcgatctctacctgatccactcgccgtcgccctcga
gtacgtcgaccctcggtccgttaccctcccggctggcactttgacggcaagagcgagatccgcccctcc
aaggccaccatccaagagacctggacggccatggagtcgctcgtcgagaagggtctctccaagagcattg
gcgtctccaacttccaggcccagctcctgtacgacctcctccgctacgccaaggtccgccccgccactct
ccagatcgagcaccaccctacctcgtccagcagaacctcctcaaccttgccaaggctgagggcatcgcc
gtgaccgctactcctccttcggccctgcttctttccgcgagttcaacatggagcacgcccagaagctcc
agcctctcctcgaggacccccaccatcaaggctattggtgacaagtacaacaaggatcctgcccaggtcct
cctccgttgggccacccagcgcggcctggccatcatccccaagtctagccgcgaggccaccatgaagtcc
aacctcaactctcttgatttcgatctctccgaggaggacatcaagaccatctctggtttcgaccgcggca
tccgcttcaaccagcccaccaactacttctccgctgagaacctctggattttcggttag (SEQ ID
NO: 9)

MVPAIKLNSGFDMPQVGFGL
WKVDGSIASDVVYNAIKACY
RLFDGACDYGNEVECGQGVA
RAIKEGIVKREELFIVSKLW
NTFHDGDRVEPIVRKQLADW
GLEYFDLYLIHSPVALEYVD
PSVRYPPGWHFDGKSEIRPS
KATIQETWTAMESLVEKGLS
KSIGVSNFQAQLLYDLLRYA
KVRPATLQIEHHPYLVQQNL
LNLAKAEGIAVTAYSSFGPA
SFREFNMEHAQKLQPLLEDP
TIKAIGDKYNKDPAQVLLRW
ATQRGLAIIPKSSREATMKS
NLNSLDFDLSEEDIKTISGF
DRGIRFNQPTNYFSAENLWI
FG* (SEQ ID NO: 10)

FIG. 23

NcXR mutant Q

Atggttcctgctatcaagctcaactccggcttcgacatgccccaggtcggcttcggcctctggaaggtcg
acggctccatcgcttccgatgtcgtctacaacgctatcaaggcaggctaccgcctcttcgatggtgcctg
cgactacggcaacgaggttgagtgcggccagggtgtagcccgcgccatcaaggagggcatcgtcaagcgc
gaggagctctttatcgtctccaagctctggaacaccttccacgacggcgaccgcgtcgagcccatcgtcc
gcaagcagcttgccgactggggtctcgagtacttcgatctctaccagatccacttccccgtcgccctcga
gtacgtcgacccctcggtccgttaccctcccggctggcactttgacggcaagagcgagatccgcccctcc
aaggccaccatccaagagacctggacggccatggagtcgctcgtcgagaagggtctctccaagagcattg
gcgtctccaacttccaggcccagctcctgtacgacctcctccgctacgccaaggtccgccccgccactct
ccagatcgagcaccaccccctacctcgtccagcagaacctcctcaaccttgccaaggctgagggcatcgcc
gtgaccgcctactcctccttcggccctgcttctttccgcgagttcaacatggagcacgcccagaagctcc
agcctctcctcgaggaccccaccatcaaggctattggtgacaagtacaacaaggatcctgcccaggtcct
cctccgttgggccacccagcgcggcctggccatcatccccaagtctagccgcgaggccaccatgaagtcc
aacctcaactctcttgatttcgatctctccgaggaggacatcaagaccatctctggtttcgaccgcggca
tccgcttcaaccagcccaccaactacttctccgctgagaacctctggattttcggttag (SEQ ID
NO: 11)

MVPAIKLNSGFDMPQVGFGL
WKVDGSIASDVVYNAIKAGY
RLFDGACDYGNEVECGQGVA
RAIKEGIVKREELFIVSKLW
NTFHDGDRVEPIVRKQLADW
GLEYFDLYQIHPPVALEYVD
PSVRYPPGWHFDGKSEIRPS
KATIQETWTAMESLVEKGLS
KSIGVSNFQAQLLYDLLRYA
KVRPATLQIEHHPYLVQQNL
LNLAKAEGIAVTAYSSFGPA
SFREFNMEHAQKLQPLLEDP
TIKAIGDKYNKDPAQVLLRW
ATQRGLAIIPKSSREATMKS
NLNSLDFDLSEEDIKTISGF
DRGIRFNQPTNYFSAENLWI
FG* (SEQ ID NO: 12)

FIG. 24

NcXR mutant QC

Atggttcctgctatcaagctcaactccggcttcgacatgccccaggtcggcttcggcctctggaaggtcg
acggctccatcgcttccgatgtcgtctacaacgctatcaaggcaggctaccgcctcttcgatggtgcctg
cgactacggcaacgaggttgagtgcggccagggtgtagcccgcgccatcaaggagggcatcgtcaagcgc
gaggagctctttatcgtctccaagctctggaacaccttccacgacggcgaccgcgtcgagcccatcgtcc
gcaagcagcttgccgactggggtctcgagtacttcgatctctaccagtgccacttccccgtcgccctcga
gtacgtcgaccccgtccgttaccctcccggctggcactttgacggcaagagcgagatccgcccctcc
aaggccaccatccaagagacctggacggccatggagtcgctcgtcgagaagggtctctccaagagcattg
gcgtctccaacttccaggcccagctcctgtacgacctcctccgctacgccaaggtccgccccgccactct
ccagatcgagcaccaccccctacctcgtccagcagaacctcctcaaccttgccaaggctgagggcatcgcc
gtgaccgcctactcctccttcggccctgcttctttccgcgagttcaacatggagcacgcccagaagctcc
agcctctcctcgaggaccccaccatcaaggctattggtgacaagtacaacaaggatcctgcccaggtcct
cctccgttgggccacccagcgcggcctggccatcatccccaagtctagccgcgaggccaccatgaagtcc
aacctcaactctcttgatttcgatctctccgaggaggacatcaagaccatctctggtttcgaccgcggca
tccgcttcaaccagcccaccaactacttctccgctgagaacctctggattttcggttag (SEQ ID
NO: 13)

```
MVPAIKLNSGFDMPQVGFGL
WKVDGSIASDVVYNAIKAGY
RLFDGACDYGNEVECGQGVA
RAIKEGIVKREELFIVSKLW
NTFHDGDRVEPIVRKQLADW
GLEYFDLYQCHFPVALEYVD
PSVRYPPGWHFDGKSEIRPS
KATIQETWTAMESLVEKGLS
KSIGVSNFQAQLLYDLLRYA
KVRPATLQIEHHPYLVQQNL
LNLAKAEGIAVTAYSSFGPA
SFREFNMEHAQKLQPLLEDP
TIKAIGDKYNKDPAQVLLRW
ATQRGLAIIPKSSREATMKS
NLNSLDFDLSEEDIKTISGF
DRGIRFNQPTNYFSAENLWI
FG* (SEQ ID NO: 14)
```

FIG. 25

NcXR mutant MQC

Atggttcctgctatcaagctcaactccggcttcgacatgccccaggtcggcttcggcctctggaaggtcg
acggctccatcgcttccgatgtcgtctacaacgctatcaaggcaggctaccgcctcttcgatggtgcctg
cgactacggcaacgaggttgagtgcggccagggtgtagcccgcgccatcaaggagggcatcgtcaagcgc
gaggagctctttatcgtctccaagctctggaacaccttccacgacggcgaccgcgtcgagcccatcgtcc
gcaagcagcttgccgactggggtctcgagtacttcgatatgtaccagtgccacttccccgtcgccctcga
gtacgtcgacccctcggtccgttaccctcccggctggcactttgacggcaagagcgagatccgcccctcc
aaggccaccatccaagagacctggacggccatggagtcgctcgtcgagaagggtctctccaagagcattg
gcgtctccaacttccaggcccagctcctgtacgacctcctccgctacgccaaggtccgccccgccactct
ccagatcgagcaccaccccacctcgtccagcagaacctcctcaaccttgccaaggctgagggcatcgcc
gtgaccgcctactcctccttcggccctgcttctttccgcgagttcaacatggagcacgcccagaagctcc
agcctctcctcgaggaccccaccatcaaggctattggtgacaagtacaacaaggatcctgcccaggtcct
cctccgttgggccacccagcgcggcctggccatcatccccaagtctagccgcgaggccaccatgaagtcc
aacctcaactctcttgatttcgatctctccgaggaggacatcaagaccatctctggtttcgaccgcggca
tccgcttcaaccagcccaccaactacttctccgctgagaacctctggatttcggttag (SEQ ID
NO: 15)

MVPAIKLNSGFDMPQVGFGL
WKVDGSIASDVVYNAIKAGY
RLFDGACDYGNEVECGQGVA
RAIKEGIVKREELFIVSKLW
NTFHDGDRVEPIVRKQLADW
GLEYFDMYQCHFPVALEYVD
PSVRYPPGWHFDGKSEIRPS
KATIQETWTAMESLVEKGLS
KSIGVSNFQAQLLYDLLRYA
KVRPATLQIEHHPYLVQQNL
LNLAKAEGIAVTAYSSFGPA
SFREFNMEHAQKLQPLLEDP
TIKAIGDKYNKDPAQVLLRW
ATQRGLAIIPKSSREATMKS
NLNSLDFDLSEEDIKTISGF
DRGIRFNQPTNYFSAENLWI
FG* (SEQ ID NO: 16)

FIG. 26

NcXR mutant MQCI

Atggttcctgctatcaagctcaactccggcttcgacatgccccaggtcggcttcggcctctggaaggtcg
acggctccatcgcttccgatgtcgtctacaacgctatcaaggcaggctaccgcctcttcgatggtgcctg
cgactacggcaacgaggttgagtgcggccagggtgtagcccgcgccatcaaggagggcatcgtcaagcgc
gaggagctctttatcgtctccaagctctggaacaccttccacgacggcgaccgcgtcgagcccatcgtcc
gcaagcagcttgccgactggggtctcgagtacttcgatatgtaccagtgccacttccccatcgccctcga
gtacgtcgaccctcggtccgttaccctcccggctggcactttgacggcaagagcgagatccgcccctcc
aaggccaccatccaagagacctggacggccatggagtcgctcgtcgagaagggtctctccaagagcattg
gcgtctccaacttccaggccagctcctgtacgacctcctccgctacgccaaggtccgcccgccactct
ccagatcgagcaccaccctacctcgtccagcagaacctcctcaaccttgccaaggctgagggcatcgcc
gtgaccgcctactcctccttcggccctgcttctttccgcgagttcaacatggagcacgcccagaagctcc
agcctctcctcgaggaccccaccatcaaggctattggtgacaagtacaacaaggatcctgcccaggtcct
cctccgttgggccacccagcgcggcctggccatcatccccaagtctagccgcgaggccaccatgaagtcc
aacctcaactctcttgatttcgatctctccgaggaggacatcaagaccatctctggttttcgaccgcggca
tccgcttcaaccagcccaccaactacttctccgctgagaacctctggattttcggttag (SEQ ID
NO: 17)

MVPAIKLNSGFDMPQVGFGL
WKVDGSIASDVVYNAIKAGY
RLFDGACDYGNEVECGQGVA
RAIKEGIVKREELFIVSKLW
NTFHDGDRVEPIVRKQLADW
GLEYFDMYQCHFPIALEYVD
PSVRYPPGWHFDGKSEIRPS
KATIQETWTAMESLVEKGLS
KSIGVSNFQAQLLYDLLRYA
KVRPATLQIEHHPYLVQQNL
LNLAKAEGIAVTAYSSFGPA
SFREFNMEHAQKLQPLLEDP
TIKAIGDKYNKDPAQVLLRW
ATQRGLAIIPKSSREATMKS
NLNSLDFDLSEEDIKTISGF
DRGIRFNQPTNYFSAENLWI
FG* (SEQ ID NO: 18)

FIG. 27

NcXR mutant VMQCI

```
atggttcctgctatcaagctcaactccggcttcgacatgccccaggtcggcttcggcctctggaaggtcg
acggctccatcgcttccgatgtcgtctacaacgctatcaaggcaggctaccgcctcttcgatggtgcctg
cgactacggcaacgaggttgagtgcggccagggtgtagcccgcgccatcaaggagggcatcgtcaagcgc
gaggagctctttatcgtctccaagctctggaacaccttccacgacggcgaccgcgtcgagcccatcgtcc
gcaagcagcttgccgactggggtgtggagtacttcgatatgtaccagtgccacttccccatcgccctcga
gtacgtcgacccctcggtccgttaccctcccggctggcactttgacggcaagagcgagatccgcccctcc
aaggccaccatccaagagacctggacggccatggagtcgctcgtcgagaagggtctctccaagagcattg
gcgtctccaacttccaggcccagctcctgtacgacctcctccgctacgccaaggtccgcccgccactct
ccagatcgagcaccaccctacctcgtccagcagaacctcctcaaccttgccaaggctgagggcatcgcc
gtgaccgcctactcctccttcggccctgcttctttccgcgagttcaacatggagcacgcccagaagctcc
agcctctcctcgaggacccccaccatcaaggctattggtgacaagtacaacaaggatcctgcccaggtcct
cctccgttgggccacccagcgcggcctggccatcatccccaagtctagccgcgaggccaccatgaagtcc
aacctcaactctcttgatttcgatctctccgaggaggacatcaagaccatctctggtttcgaccgcggca
tccgcttcaaccagcccaccaactacttctccgccgagaacctctggattttcggttag (SEQ ID
NO: 19)
```

```
MVPAIKLNSGFDMPQVGFGL
WKVDGSIASDVVYNAIKAGY
RLFDGACDYGNEVECGQGVA
RAIKEGIVKREELFIVSKLW
NTFHDGDRVEPIVRKQLADW
GVEYFDMYQCHFPIALEYVD
PSVRYPPGWHFDGKSEIRPS
KATIQETWTAMESLVEKGLS
KSIGVSNFQAQLLYDLLRYA
KVRPATLQIEHHPYLVQQNL
LNLAKAEGIAVTAYSSFGPA
SFREFNMEHAQKLQPLLEDP
TIKAIGDKYNKDPAQVLLRW
ATQRGLAIIPKSSREATMKS
NLNSLDFDLSEEDIKTISGF
DRGIRFNQPTNYFSAENLWI
FG* (SEQ ID NO: 20)
```

FIG. 28 pACYCAraXylE ggggaattgtgagcggataacaattcccctgtagaaataattttgtttaactttaataaggagatatacc
atgtctgttactggtgatcaccctgtggctgtgtaattcgaaacggctgaagcgggagtaaaaagtcagc
acgccgaaatggcgcggcgtgctggacaggaagattacagcgtagcagtttgttgtgttttcttcgtttc
cggttcccagagcgcttccagctcctcaagggttttacctttggtttccgggacaaatttccacataaac
agtgctgccagaacgcccatacaaccgtaaatccagtaggagaaaccgttgtggaaatgggccaccagcc
aggagttttgtccatcatcgggaaggtccaggagacgaagtagttcgccagccactgggccgccaccgc
gattgccagcgctttaccacgaatagcattcgggaagatttccgacagcagtacccagcataccggaccc
caggacatggcaaaggcggcaacatagaacagcatcgacagtagcgccacaatacccggtgcctgagtgt
aaaacgcggtaccgaggctaaacataccgattgccattccgagtgcgccgataatttgcagtggcttacg
accaaatttatccaccgtcataattgccagaacggtgaaggtgaggttgataactccgacaataatggtc
tgcaacagcgcgatatccgtgctggcccccagcgtttttgaacacttccggcgcgtagtacagcaccacat
tgatgccgacaaattgctggaagatggagagcattacgccgattacaatcacgcccacgccaaacatcag
cagacgaccaccggttttgcggccatgatccagggagtgtttaatttcctgtactgcctgagttgcaagc
gtgttgcccataattttgcgcaggataccttccgcctgttcttgcttgccgcgcgacatcagccagcgag
gactttctggcacggtatacagcagcattaagaacagcagtgcagggatacattccgaggcaaacatata
acgccagccgtcagtattcagccagctggcatcaccggaacgggcaataaaatagtttacgcagtaaact
aaaagttgcccgaaaataatcgcaaactggttaaaagagaccagtttcccgcgaatatgagctggagcca
gttccgcaatatacattggcgagagcattgaggctaaaccaacgccaataccgccaataatgcgataaat
aacaaattccgggacataacctgccagataaacaggcacagtgttgtccgggtttatagaggtaaaacca
agttctggccaggcagaacctacaccagaaataaaaaacaggacagcagcaatcttaagtgaatcacgac
gaccgaagcggttactgcaataaccaccgagggcaccgccgatgatgcaaccaatcagagcgctggccac
gcaaaacccctaacagggagttggcagcggattcacttaagttttgtggagcaacaaagacggtattgagt
gactcaacagtaccggaaataacggcggtgtcgtagccaaataataaaccacctaatgtagcgactaagg
taatcgaaaatatataactggaattatactgggtattcatatgccaaaaaaacgggtatggagaaacagt
agagagttgcgataaaaagcgtcaggtaggatccgctaatctttatggataaaaatgctatggcatagcaa
agtgtgacgccgtgcaaataatcaatgtggacttttctgccgtgattatagacactttttgctacgcgttt
ttgtcatggccttggtcccgctttgttacagaatgcttttaataagcggggttaccggtttggttagcga
gaagagccagtaaaagacgcagtgacggcaatgtctgatgcaatatggacaattggttttcttctctgaat
ggcgctgcaggtcgacaagcttgcggccgcataatgcttaagtcgaacagaaagtaatcgtattgtacac
ggccgcataatcgaaattaatacgactcactatagggggaattgtgagcggataacaattcccatcttag
tatattagttaagtataagaaggagatatacatatggcagatctcaattggatatcggccggccacgcga
tcgctgacgtcggtaccctcgagtctggtaaagaaaccgctgctgcgaaatttgaacgccagcacatgga
ctcgtctactagcgcagcttaattaacctaggctgctgccaccgctgagcaataactagcataaccccctt
ggggcctctaaacgggtcttgagggttttttgctgaaacctcaggcatttgagaagcacacggtcacac
tgcttccggtagtcaataaaccggtaaaccagcaatagacataagcggctatttaacgaccctgccctga
accgacgaccgggtcgaatttgctttcgaatttctgccattcatccgcttattatccttattcaggcgt
agcaccaggcgtttaagggcaccaataactgccttaaaaaaattacgccccgccctgccactcatcgcag
tactgttgtaattcattaagcattctgccgacatggaagccatcacagacggcatgatgaacctgaatcg
ccagcggcatcagcaccttgtcgccttgcgtataatatttgcccatagtgaaaacggggggcgaagaagtt
gtccatattggccacgtttaaatcaaaactggtgaaactcacccagggattggctgagacgaaaaacata
ttctcaataaacccctttagggaaataggccaggttttcaccgtaacacgccacatcttgcgaatatatgt
gtagaaactgccggaaatcgtcgtggtattcactccagagcgatgaaaacgtttcagtttgctcatggaa
aacggtgtaacaagggtgaacactatcccatatcaccagctcaccgtctttcattgccatacggaactcc
ggatgagcattcatcaggcgggcaagaatgtgaataaaggccggataaaacttgtgcttattttttcttta
cggtctttaaaaaggccgtaatatccagctgaacggtctggttataggtacattgagcaactgactgaaa
tgcctcaaaatgttctttacgatgccattgggatatatcaacggtggtatatccagtgatttttttctcc
attttagcttccttagctcctgaaaatctcgataactcaaaaaatacgcccggtagtgatcttatttcat
tatggtgaaagttggaacctcttacgtgccgatcaacgtctcatttttcgccaaaagttggcccagggctt
cccggtatcaacagggacaccaggatttatttattctgcgaagtgatcttccgtcacaggtatttattcg
gcgcaaagtgcgtcggtgatgctgccaacttactgatttagtgtatgatggtgttttgaggtgctcca
gtggcttctgtttctatcagctgtccctcctgttcagctactgacggggtggtgcgtaacggcaaaagca
ccgccggacatcagcgctagcggagtgtatactggcttactatgttggcactgatgagggtgtcagtgaa
gtgcttcatgtggcaggagaaaaaggctgcaccggtgcgtcagcagaatatgtgatacaggatatattc
cgcttcctcgctcactgactcgctacgctcggtcgttcgactgcggcgagcggaaatggcttacgaacgg

FIG. 29

```
ggcggagatttcctggaagatgccaggaagatacttaacagggaagtgagagggccgcggcaaagccgtt
tttccataggctccgccccctgacaagcatcacgaaatctgacgctcaaatcagtggtggcgaaacccg
acaggactataaagataccaggcgtttcccctggcggctccctcgtgcgctctcctgttcctgcctttcg
gtttaccggtgtcattccgctgttatggccgcgtttgtctcattccacgcctgacactcagttccgggta
ggcagttcgctccaagctggactgtatgcacgaaccccccgtcagtccgaccgctgcgccttatccggt
aactatcgtcttgagtccaacccggaaagacatgcaaaagcaccactggcagcagccactggtaattgat
ttagaggagttagtcttgaagtcatgcgccggttaaggctaaactgaaaggacaagttttggtgactgcg
ctcctccaagccagttacctcggttcaaagagttggtagctcagagaaccttcgaaaaaccgccctgcaa
ggcggttttttcgtttcagagcaagagattacgcgcagaccaaaacgatctcaagaagatcatcttatt
aatcagataaaatatttctagatttcagtgcaatttatctcttcaaatgtagcacctgaagtcagcccca
tacgatataagttgtaattctcatgttagtcatgccccgcgcccaccggaaggagctgactgggttgaag
gctctcaagggcatcggtcgagatcccggtgcctaatgagtgagctaacttacattaattgcgttgcgct
cactgcccgctttccagtcgggaaacctgtcgtgccagctgcattaatgaatcggccaacgcgcggggag
aggcggtttgcgtattgggcgccagggtggttttttcttttcaccagtgagacgggcaacagctgattgcc
cttcaccgcctggccctgagagagttgcagcaagcggtccacgctggtttgccccagcaggcgaaaatcc
tgttgatggtggttaacggcgggatataacatgagctgtcttcggtatcgtcgtatcccactaccgaga
tgtccgcaccaacgcgcagcccggactcggtaatggcgcgcattgcgcccagcgccatctgatcgttggc
aaccagcatcgcagtgggaacgatgccctcattcagcatttgcatggtttgttgaaaaccggacatggca
ctccagtcgccttcccgttccgctatcggctgaatttgattgcgagtgagatatttatgccagccagcca
gacgcagacgcgccgagacagaacttaatgggcccgctaacagcgcgatttgctggtgacccaatgcgac
cagatgctccacgcccagtcgcgtaccgtcttcatgggagaaaataatactgttgatgggtgtctggtca
gagacatcaagaaataacgccggaacattagtgcaggcagcttccacagcaatggcatcctggtcatcca
gcggatagttaatgatcagcccactgacgcgttgcgcgagaagattgtgcaccgccgctttacaggcttc
gacgccgcttcgttctaccatcgacaccaccacgctggcacccagttgatcggcgcgagatttaatcgcc
gcgacaatttgcgacggcgcgtgcagggccagactggaggtggcaacgccaatcagcaacgactgtttgc
ccgccagttgttgtgccacgcggttgggaatgtaattcagctccgccatcgccgcttccacttttttcccg
cgttttcgcagaaacgtggctggcctggttcaccacgcgggaaacggtctgataagagacaccggcatac
tctgcgacatcgtataacgttactggtttcacattcaccaccctgaattgactctcttccgggcgctatc
atgccataccgcgaaaggttttgcgccattcgatggtgtccgggatctcgacgctctcccttatgcgact
cctgcattaggaaattaatacgactcactata (SEQ ID NO: 21)
```

FIG. 29 (cont.)

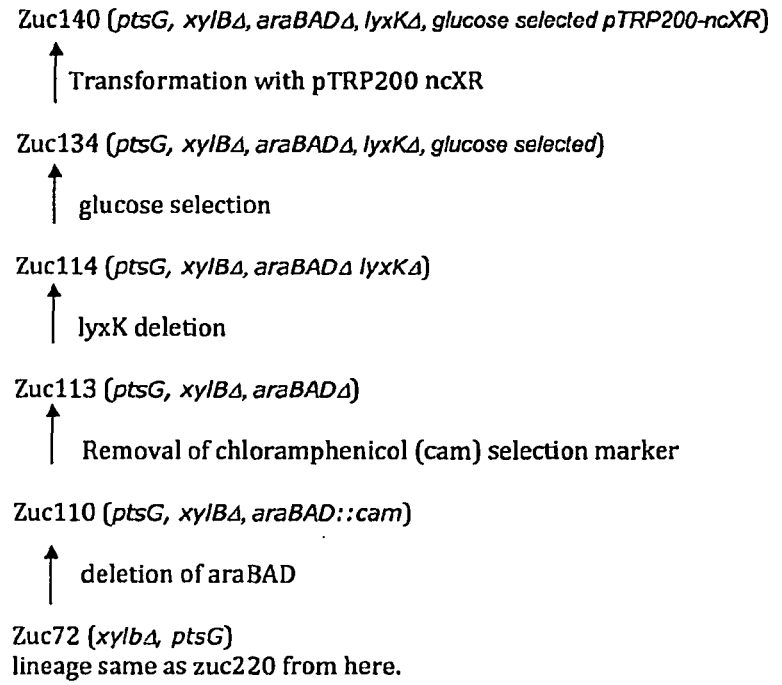
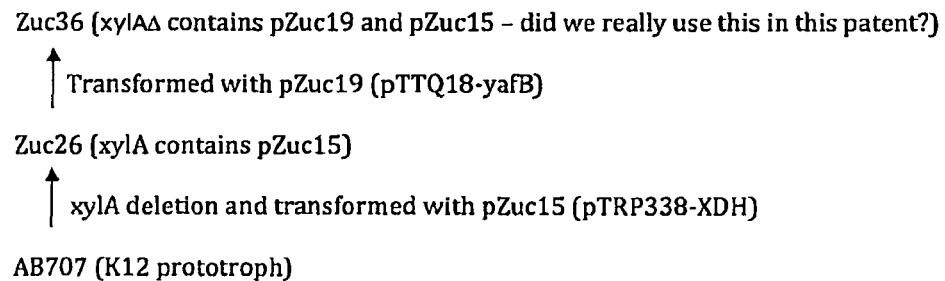
FIG. 30 (cont.)

AB707 is a K12 prototroph obtained from CGSC.

Zuc138 (*ptsG, xylBΔ, araBADΔ, lyxKΔ, glucose selected* containing pATX221)

↑ transformation with pATX221

Zuc134 (*ptsG, xylBΔ, araBADΔ, lyxKΔ, glucose selected*)

Zuc142 (*ptsG, xylBΔ, araBADΔ, lyxKΔ, glucose selected* containing pATX231)

↑ transformation with pATX231

Zuc134 (*ptsG, xylBΔ, araBADΔ, lyxKΔ, glucose selected*)

Zuc172 (F- ompT hsdSB(rB- mB-) gal dcm (DE3), with pTRP200-ncXRVMQCI)

↑ Transform with pTRP200-ncXRVMQCI (HZ mutant, plasmid created by zuChem, this is not in the plasmid list)

E. coli B derivative obtained from Novagen

Zuc136 (*ptsG, xylBΔ, araBADΔ, lyxKΔ, glucose selected* containing pATX210)

↑ transformation with pATX210

Zuc134 (*ptsG, xylBΔ, araBADΔ, lyxKΔ, glucose selected*)

Zuc166 (*ptsG, xylBΔ, araBADΔ, lyxKΔ, glucose selected* containing pTRP200-cgXR)

↑ transformation with pTRP200-cgXR

Zuc134 (*ptsG, xylBΔ, araBADΔ, lyxKΔ, glucose selected*)

FIG. 30 (cont.)

PRODUCTION OF XYLITOL FROM A MIXTURE OF HEMICELLULOSIC SUGARS

CROSS REFERENCE TO RELATED APPLICATIONS

The present application is a U.S. nationalization under 35 U.S.C. § 371 of International Application No. PCT/US2011/021277, filed Jan. 14, 2011, which claims priority to U.S. application No. 61/295,551, filed Jan. 15, 2010, application No. 61/328,609, filed Apr. 27, 2010, and application No. 61/391,951, filed Oct. 11, 2010. The disclosures set forth in the referenced applications are incorporated herein by reference in their entireties, including all information as originally submitted to the United States Patent and Trademark Office.

BACKGROUND

Materials and methods are described to produce xylitol from a mixture of hemicellulosic sugars by several routes. Examples include either as a direct co-product of a biorefinery or ethanol facility, or as a stand-alone product produced from an agricultural or forestry biomass feedstock including using, e.g. ethanol waste streams.

Xylitol has several favorable properties as a sugar substitute, such as low caloric content, anticariogenicity, good gastrointestinal tolerance, and near insulin-independent metabolism in humans. The traditional production of xylitol involves direct chemical hydrogenation of hemicellulosic hydrolysates over a Raney-Nickel catalyst followed by extensive purification from non-specific reduction products. In the chemical process, D-xylose is converted to xylitol by catalytic reduction. This method utilizes specialized and expensive equipment for the high pressure and temperature requirements as well as the use of a Raney-Nickel catalyst that can introduce trace nickel into the final product, which is undesirable. Additionally, the overall yield is only 50-60%. The final product must also be purified. This multi-step process is expensive and inefficient.

Hydrolysate from birch trees has historically been the only economic source of xylose used to make xylitol by chemical hydrogenation. Birch tree hydrolysate is a byproduct of the paper and pulping industry and it has only minor amounts of arabinose and other sugars. However availability severely limits this source of xylitol. Hydrolysis of other xylan-rich materials, such as trees, straws, corncobs, oat hulls under alkaline conditions also yields hemicellulose hydrolysate, however these hydrolysates contain too many sugars other than xylose, especially L-arabinose. These competing sugars create a number of by-products during the hydrogenation process that are difficult and costly to remove.

Biocatalytic routes to xylitol production using fungal or yeast xylose reductase (XR) have also been explored. Unfortunately, the nonspecific nature of direct hydrogenation is only partially addressed in the biocatalytic route. The natural promiscuity of XRs toward other sugars, particularly L-arabinose, another major component of hemicelluloses, necessitates the prior purification of D-xylose to minimize formation of L-arabinitol. Because D-xylose and L-arabinose are epimers, their separation is nontrivial, and is one of the leading obstacles to the more economical production of xylitol.

Because there is a significant amount of arabinose in the hydrolysates, a significant amount of arabinitol (arabitol) is produced because the xylose reductase enzyme that converts xylose to xylitol also converts arabinose to arabinitol. A significant challenge was to develop either a process that produces negligible amounts of arabinitol or alternatively converts the arabinose into additional xylitol.

While some basic research has been performed by others in the field, development of an effective bioprocess for the production of xylitol has been elusive. Many of these systems suffered from problems such as poor microbial strain performance, low volumetric productivity, and too broad of a substrate range. Moreover, kinetics and overall performance of the enzymes reported to date have not been engineered (via methods such as directed evolution) to maximize efficiency. More efficient enzyme activity would result in improved throughput and shorter reaction times, both of which are crucial to a commercially viable process.

Most of the research performed has also been carried out using a highly purified and concentrated D-xylose substrate. This substrate has no significant amounts of other pentoses such as arabinose or other hexoses such as D-glucose. While some reasonable yields with such a substrate have been reported, developing a bioprocess with pure D-xylose is impractical due to the cost of this substrate and the fact that it can be hydrogenated at similar costs and better space-time yields.

None of the approaches described in this section have been commercially effective for a number of reasons. First, xylose uptake is often naturally inhibited by the presence of glucose that is used as a preferred carbon source for many organisms. Second, none of the enzymes involved have been optimized to the point of being cost effective. Finally, xylose in its pure form is expensive and any requirement for a bioprocess to use pure xylose results in direct competition with inexpensive chemical hydrogenation. Additionally, all of the systems developed would produce arabinitol as a significant contaminating byproduct since the xylitol dehydrogenase used has similar activity with both xylose and arabinose.

Xylitol could potentially be a byproduct of ethanol production. When products such as ethanol or other chemicals are produced from corn by current processes, only starch is generally utilized. Thus, during ethanol production, significant by-products rich in pentose and other sugars are made. For example, when ethanol is produced from a dry-mill operation (about 55% of the facilities today) distiller's dry grains (DDG) and other byproducts are produced. In the wet-mill operation (the remaining 45% of current facilities) corn fiber rich in hemicellulose is produced. These products are usually sold as inexpensive animal feed or otherwise disposed of, but both the corn fiber and distiller's dry grains could potentially be converted to other value-added products, such as xylitol which could help improve the economics of ethanol production.

SUMMARY OF THE DISCLOSURE

Methods and compositions are disclosed to produce xylitol—some that are useful on an industrial scale, and all having advantages. Methods include a new process that would allow xylitol to be produced from a variety of agricultural and forestry derived hemicellulose feedstocks such as hardwoods, softwoods, bagasse, wheat straw, corn and corn fiber, sources such as those that are leftover from U.S. ethanol production, bioenergy production, or other biochemical production. Fermentation organisms were designed to alleviate some of the previous problems, notably by minimizing arabinitol.

A variety of fermentation systems disclosed herein are able to convert a hemicellulose mixture (arabinose, xylose, and a variety of C6 sugars) to a low-arabinotol product.

Systems to produce xylitol include:
(A) conversion of xylose to xylitol by a xylose reductase;
(B) conversion of L-arabinose to xylitol, reduce xylose;
(C) reduce D-xylose and metabolize arabinose.

Aspects of the invention also include:
(A) preparation and improvement of industrial hemicellulose samples;
(B) analysis of fermentation inhibition by different industrial hemicellulose samples; and
(C) novel xylose reductase genes.

Aspects of this disclosure include an *E. coli* strain that efficiently produces xylitol from D-xylose, wherein xylitol is produced at a purity of approximately 90-100% from an equivalent mixture of D-xylose, L-arabinose, and D-glucose. The method to reduce D-xylose to xylitol uses an engineered *E. coli* strain, wherein there is a minimal production of L-arabinitol byproduct.

The biocatalytic reduction of D-xylose to xylitol requires separation of the substrate from L-arabinose, another major component of hemicellulosic hydrolysate. This step is necessitated by the innate promiscuity of xylose reductases, which can efficiently reduce L-arabinose to L-arabinitol, an unwanted byproduct. Unfortunately, due to the epimeric nature of D-xylose and L-arabinose, separation can be difficult, leading to high production costs. To overcome this issue, an *E. coli* strain is disclosed that efficiently produces xylitol from D-xylose with minimal production of L-arabinitol byproduct. By combining this strain with a previously engineered xylose reductase mutant, (SEQ ID NO: 19 and 20) L-arabinitol formation is eliminated and xylitol is produced to near 100% purity from an equiweight mixture of D-xylose, L-arabinose, and D-glucose.

BRIEF DESCRIPTION OF THE DRAWINGS

FIG. 1. Potential pathways for converting xylose or arabinose to xylitol. (A) Pathways A—Conversion of xylose to xylitol via xylose reductase; (B) Pathway B—conversion of xylose to xylitol via a D-xylulose intermediate; (C) Pathway C; conversion of arabinose to xylitol via epimerase.

FIG. 5: Two stage production of xylitol in biomass hydrolysate using first the L-arabinose to xylitol (epimerase) Pathway C followed by the xylose to xylitol (xylose reductase) Pathway A: (A) 2 stage, (B) 2 stage higher sugars.

FIG. 16. Gene sequence of xylose reductase from *Chaetomium globosum* (SEQ ID NOS 1-2, respectively, in order of appearance).

FIG. 18. NcXRwt sequence (SEQ ID NOS 3-4, respectively, in order of appearance).

FIG. 19. pACYC-ncxr sequence (SEQ ID NO: 5).

FIG. 20. pXXR sequence (SEQ ID NO: 6).

FIG. 21. pTrcXR sequence (SEQ ID NO: 7).

FIG. 22. pAraXR sequence (SEQ ID NO: 8).

FIG. 23. NcXR mutant S sequence (SEQ ID NOS 9-10, respectively, in order of appearance).

FIG. 24. NcXR mutant Q sequence (SEQ ID NOS 11-12, respectively, in order of appearance).

FIG. 25. NcXR mutant QC sequence (SEQ ID NOS 13-14, respectively, in order of appearance).

FIG. 26. NcXR mutant MQC sequence (SEQ ID NOS 15-16, respectively, in order of appearance).

FIG. 27. NcXR mutant MQCI sequence (SEQ ID NOS 17-18, respectively, in order of appearance).

FIG. 28. NcXR mutant VMQCI sequence (SEQ ID NOS 19-20, respectively, in order of appearance).

FIG. 29. pACYCAra XylE sequence (SEQ ID NO: 21).

DETAILED DESCRIPTION

I. Materials and methods are described to produce xylitol by several routes for example either as a direct co-product of a biorefinery or ethanol facility, or produced as a stand-alone product using, e.g. ethanol waste streams.

A. Conversion of Xylose to Xylitol Via Xylose Reductase.

1. Use D-Xylose Reductase on Arabinose-Depleted Feedstock; in an Arabinose Utilizing Organisms; Xylose Reductases Will Reduce Arabinose:

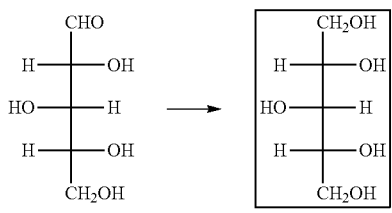 [SMILES: O=CC(O)C(O)C(O)CO ; OCC(O)C(O)C(O)CO]

Two organisms designated ZUC140 and ZUC166 can accomplish this. Xylose can be converted to xylitol at a high efficiency, but also produces arabitol from arabinose (tested at 50:50 ratio).

One way to convert xylose to xylitol is directly through the use of a xylose reductase as depicted in FIG. 1A (Pathway A). Several xylose reductase genes had previously been cloned into *E. coli* expression vectors, expressed, and tested for ability to convert xylose into xylitol. Most genes are expressed and very active in constitutive expression systems within strain ZUC134. *E. coli* strain Zuc134 was created from K12 prototroph AB707 through a combination of PCR based genetic deletion and selection for improved growth on glucose. First ptsG was removed, followed by xylB, then araBAD, and finally lyxK in successive order. The final strain was then selected on M9+glucose liquid medium several times for improved growth, a single colony was isolated, cultured, and stored at −80° C.

Figure 2:
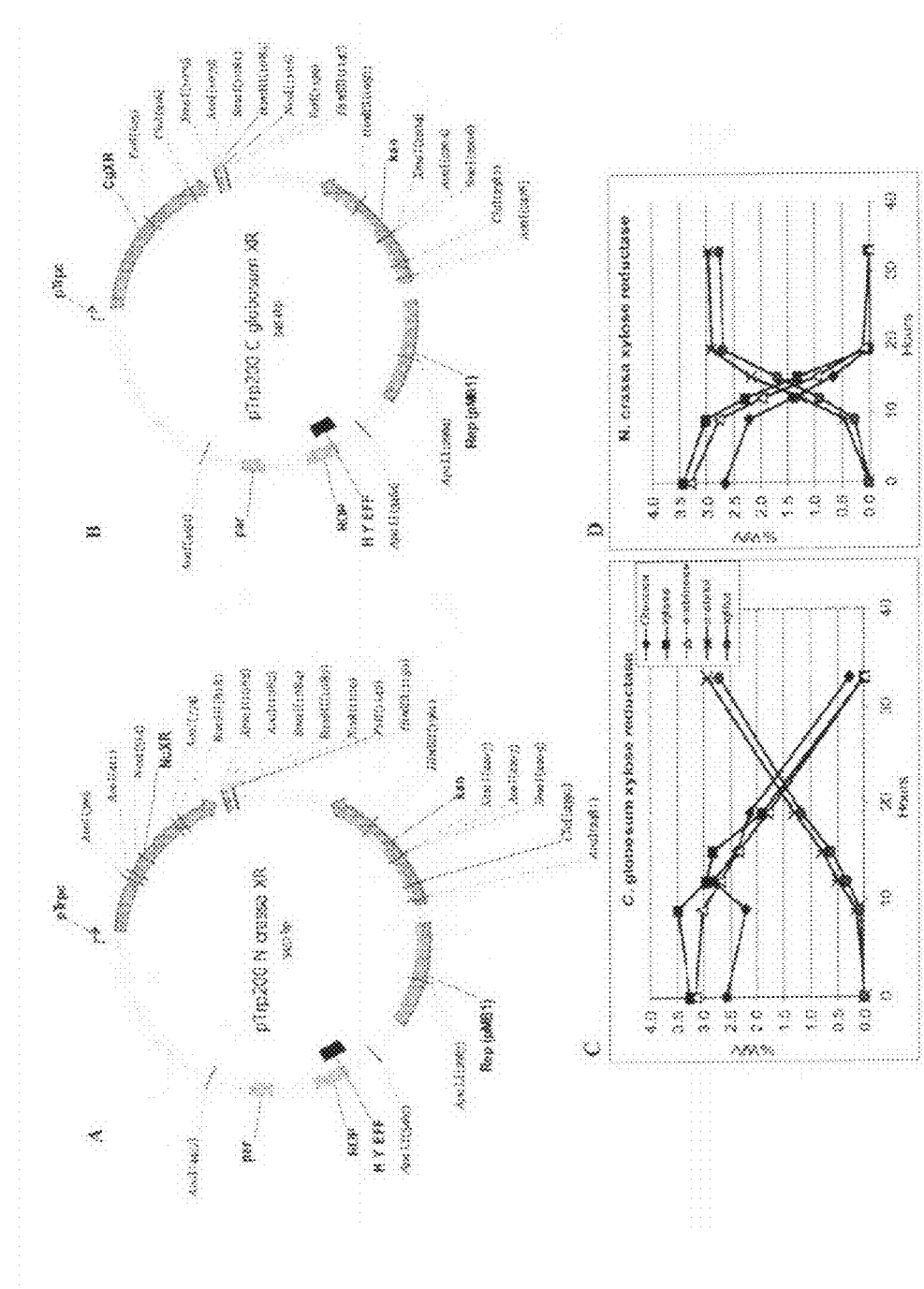
FIG. 2: Conversion of xylose to xylitol via xylose reductase: (A) *C. globosum* (SEQ ID NO: 2); (B) *N. crasser*. (SEQ ID NO: 19 and 20); (C) and (D) bioconversion with the XR from (A) and (B).

The best results achieved were with the xylose reductases from *Neurospora crassa* (McXR) and *Chaetomium globosum* (CgXR) [FIG. 2(D), (C)]. CgXR was synthetically constructed for *E. coli* expression [FIG. 2(A)], whereas NcXR was isolated from mRNA of *N. crassa* [FIG. 2B]. Both genes were placed in the expression vector pTRP200 under the pTRP promoter allowing constitutive expression. The resulting strains ZUC140 (ZUC134 NcXR) and ZUC166 (ZUC134 CgXR) are very powerful reducing biocatalysts.

The ability to convert a "synthetic hemicellulose" mixture that contained both xylose and arabinose together as a starting material was investigated. Although hemicelluloses vary in concentration of these sugars, a 50:50 mixture was used in these experiments, unless otherwise indicated. This can be supplemented by an additional C6 sugar such as glucose for growth of the strains.

One liter bioconversions were performed to test these systems with a synthetic hemicellulose substrate containing a 50:50 mixture of xylose and arabinose (30 g/L each). In these experiments ZUC140 was capable of reducing 30 g D-xylose to xylitol in just 20 hrs. ZUC166 was capable of the same reduction in approximately 30 hrs. Both of these systems, however, concurrently reduce 30 g L-arabinose to L-arabitol over the same time period. A problem is that L-arabitol is an undesirable side product. Method: 2 L BiostatB (Sartorius). Medium: 10 g/L tryptone, 5 g/L yeast extract, 5 g/L sodium chloride; 2.6 g/L dibasic potassium phosphate Sterilized in 800 mL. Sugars sterilized separately and added in 150 mL prior to inoculation to indicated starting concentrations. [glucose was also added, same concentration, not shown]. Inoculated with 50 mL seed, overnight shake flask in LB medium. pH autocontrolled at pH 7.0 with ammonium hydroxide, Temp 30° C., agitation 800 rpm, 1 vvm air (1 Lpm). Products were tested by HPLC.

2. Conversion of C-5 Mixed Sugars to Xylitol Via a N-Xylulose Intermediate (XI/XDH).

Isomerize D-xylose to D-xylulose; reduce D-xylulose to xylitol (arabinose is unaffected by either enzyme):

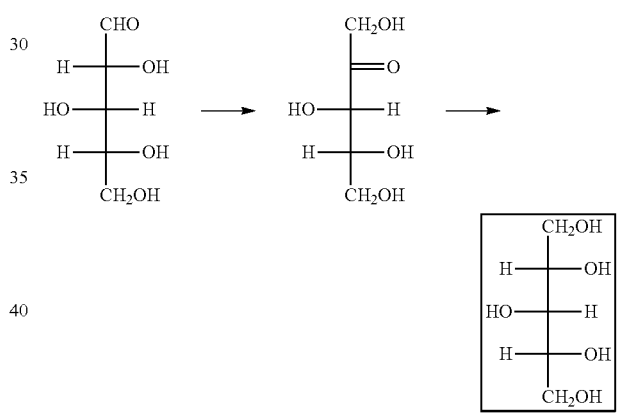

Another method to convert xylose to xylitol has the advantage of not converting L-arabinose to arabitol, because both enzymes (XI and XDH) do not have any activity with L-arabinose as depicted in FIG. 1B (Pathway B). Plasmid pZUC036 (see U.S. 2006/0110809 incorporated herein by reference) contained a XI cloned from *E. coli* and a XDH cloned from *Trichoderma reesei* (*Hypocrea jecorina*) under the control of the pTRP constitutive promoter.

Figure 3:
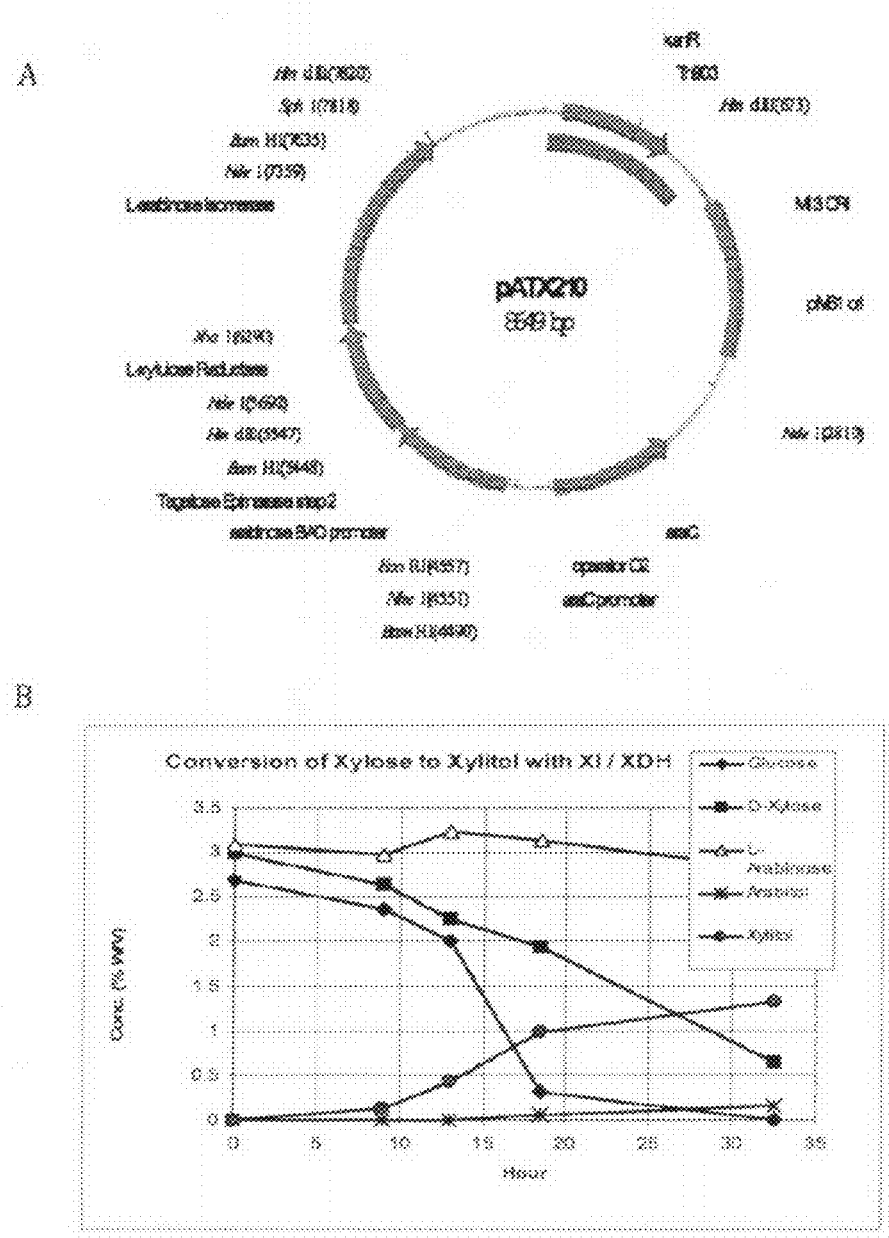
FIG. 3: Conversion of C-5 mixed sugars to xylitol; via a D-xylulose intermediate (XI/XDH): (A) pATX210, (B) L-arabinose to xylitol, (C) pATX215
Figure 3C:
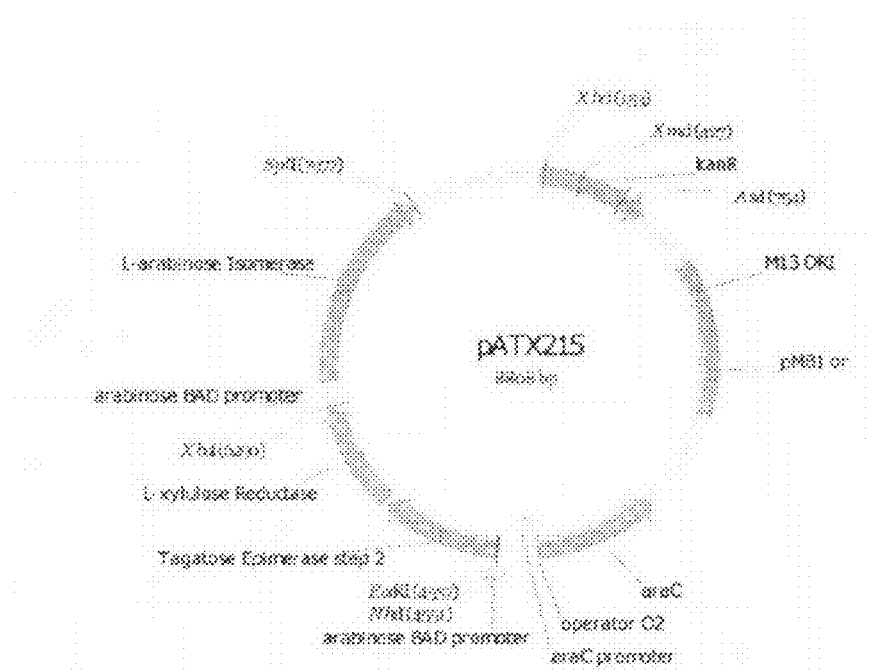

This plasmid was tested in *E. coli* ZUC134 (see U.S. 2006/0110809 incorporated herein by reference) for conversion of a synthetic hemicellulose mixture of D-xylose and L-arabinose to xylitol. Using this system, 27 g/L xylitol was produced from 50 g/l, xylose without the production of any significant amount of arabitol. Higher concentrations of D-xylose did not result in more xylitol, and further study pinpointed the problem. Xylitol is inhibitory to XI activity, therefore a selection method was developed for creating xylitol resistant XI mutants. After several rounds of mutagenesis and selection, a more resistant XI was created and cloned into the expression vector to create pZUC052 (see U.S. 2006/110809 incorporated herein by reference). This mutant was capable of converting 150 g/L D-xylose to 74 g/L xylitol. However, with lower concentrations of D-xylose such as 30 g/L, conversion still was never more than 50% (FIG. 3). L-arabitol production from 30 g/L arabinose was insignificant.

B. Convert L-Arabinose to Xylitol, Reduce Xylose

Isomerize L-arabanose to L-ribulose; isomerize ribulose to L-xylulose; reduce L-xylulose to xylitol:

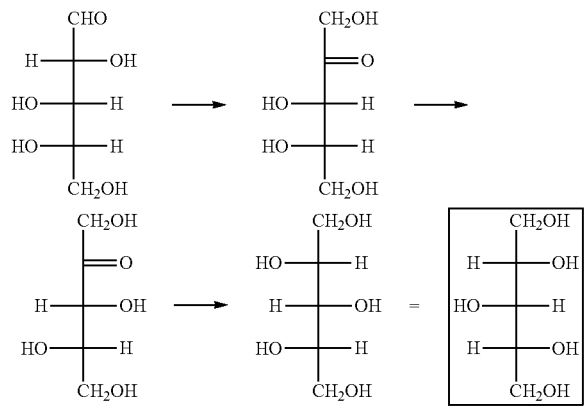

1. Conversion of C-5 Mixed Sugars to Xylitol Via Epimerase Pathway.

Figure 4:
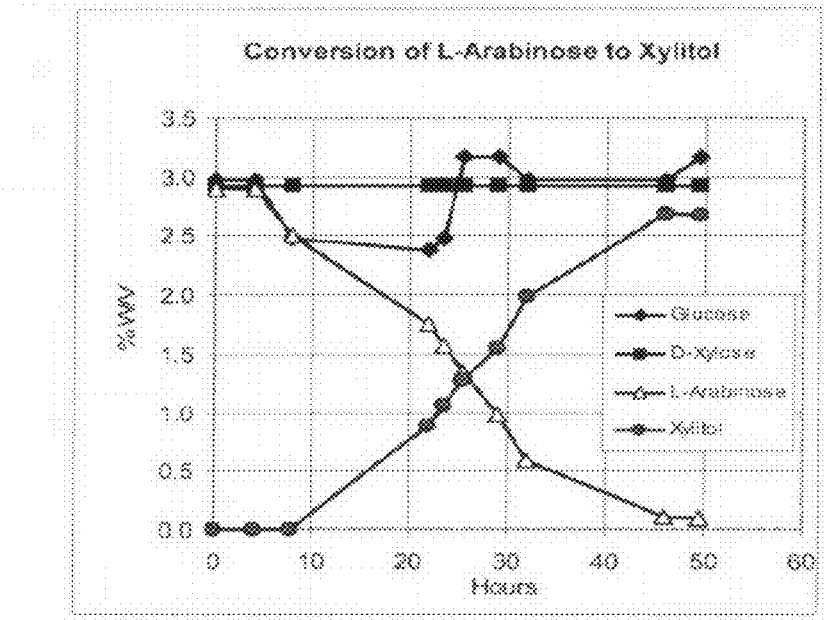
FIG. 4: Conversion of L-arabinose in to xylitol by the epimerase of Pathway C.

FIG. 1C (Pathway C) depicts a pathway for converting L-arabinose to xylitol via an epimerase. Plasmid pATX210 (FIG. 3A) [U.S. patent application Ser. No. 11/827,506], Sakakibara et al. Methods for microbial production of xylitol from arabinose) contains an optimal combination of LAI from *E. coli* (araA) LXR from *Ambrosiozyma monospora* and DTE from *Rhizobium radiobacter* although alternative LAI, LXR and DTE genes could also be used. Plasmid pATX210 is a derivative of plasmid pBAD18kan which contains an arabinose inducible promoter and kanamycin resistance marker. This plasmid was modified to contain a three gene cassette containing tagatose epimerase, xylulose reductase, and L-arabinose isomerase in that order moving away from the promoter. To test for the ability to convert a mixed sugar stream containing D-xylose, L-arabinose and other sugars, pATX210 was used to transform ZUC134, resulting in strain ZUC136. As shown in FIG. 3B this strain has reproducibly been able to convert ~90% of L-arabinose into xylitol (30 g/L to 27 g/L), while not consuming or modifying D-xylose (FIG. 4) in 48 hours.

2. Conversion of C-5 Sugar Mixtures to Xylitol—Two Stage Bioconversion (Path A and Path C Sequentially).

Another method of converting all of the xylose and arabinose to xylitol is to carry out a two-step sequential bioconversion using two different strains. For example, using strain ZUC136 (with the LAI/DTE/LXR pathway) to convert all of the L-arabinose to xylitol, optionally followed by a pasteurization or purification process to remove the original strain, followed by the use of ZUC140 (which contains the XR pathway) to convert the D-xylose in the resulting mixture to xylitol. If effective, the process will proceed without significant amounts of unwanted byproducts such as unreacted sugars or contaminating polyols being produced.

FIG. 5A shows the results of this strategy. The two-stage 1 L bioconversion started with a 50:50 synthetic hemicellulose (containing 33 g L-arabinose and 34.5 g D-xylose). The first stage bioconversion with ZUC136 lasted 50 hrs, and the second stage bioconversion with ZUC140 lasted 30 hrs. At the end of the bioconversion there was less than 8 g of combined other detectable sugars and polyols and the reaction produced approximately 65 g xylitol.

The process can also be run at higher concentrations of xylose and arabinose. As shown in FIG. 5B, Stage 1 proceeds until there are only small amounts of arabinose remaining unreacted. Stage 2 proceeds to completion converting all the xylose to xylitol. In this case a 2:1 synthetic hemicellulose feedstock was used with approximately 60 g D-xylose and 26 g L-arabinose. This process successfully produced 63 g xylitol at a concentration of 75 g/L.

During the two-stage bioconversion experiments, surprisingly the second stage, conversion of the xylose to xylitol was not only very rapid but did not generate a significant amount of arabitol even though there was some unreacted arabinose remaining in the broth. This was counter to expectations because most xylose reductase enzymes are known to convert both xylose to xylitol, and arabinose to arabitol. This was significant because the presence of excess amounts of arabitol in the final mixture would make final purification of xylitol overly expensive. Because of both the speed of the reaction, and the nature of the xylose reductase being used, the enzyme is more specific to xylose than other xylose reductases. The reaction proceeds without production of much arabitol when the reaction is slowed down, as it is in the second stage of the 2-stage conversion.

3. Conversion of C-5 Mixture to Xylitol Using a Single Strain with the Xylose Reductase and Epimerase Pathways Combined.

Figure 6:
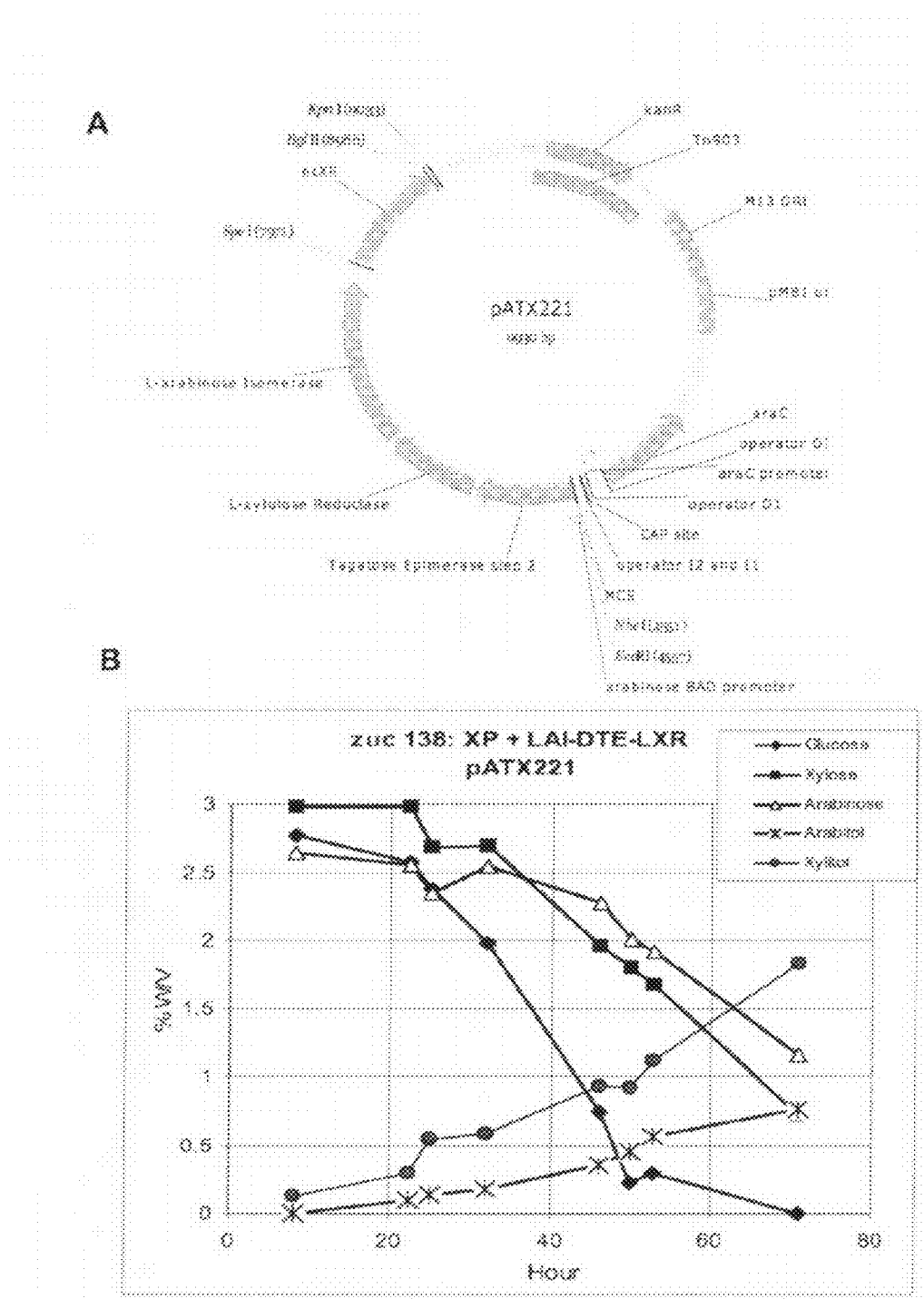
FIG. 6: Conversion of a C-5 mixture to xylitol and arabinitol with ZUC138 (A) containing a plasmid with combined genes for Pathway A and Pathway C (pATX221); and (B) bioconversion to xylitol and arabitol.

A way to convert both arabinose and xylose to xylitol is to put two separate pathways into a single organism. One combination of pathways in a single strain is the combination of Pathway A (XR) for converting D-xylose to xylitol, and Path C (LAI, DTE, LXR) for converting L-arabinose to xylitol. The primary issue is the production of L-arabitol from the activity of XR in the presence of L-arabinose. Combination of these pathways was achieved with the creation of pATX221 (created by insertion of the pTRP promoted ncXR into pATX2210 as depicted in FIG. 6(A)) which was subsequently transformed into ZUC134 to create ZUC138. The resulting strain grew and produced xylitol although slowly. In a 70 hr bioconversion this strain produced 20 g/L xylitol and 7 g/L arabitol from 30 g/L D-xylose and 26 g/L L-arabinose (FIG. 6(B)). To reduce the production of L-arabitol, a more D-xylose specific XR can be utilized.

4. Conversion of C-5 Mixture to Xylitol Using a Single Strain with the XI/XDH and Epimerase Pathways Combined.

Figure 7:
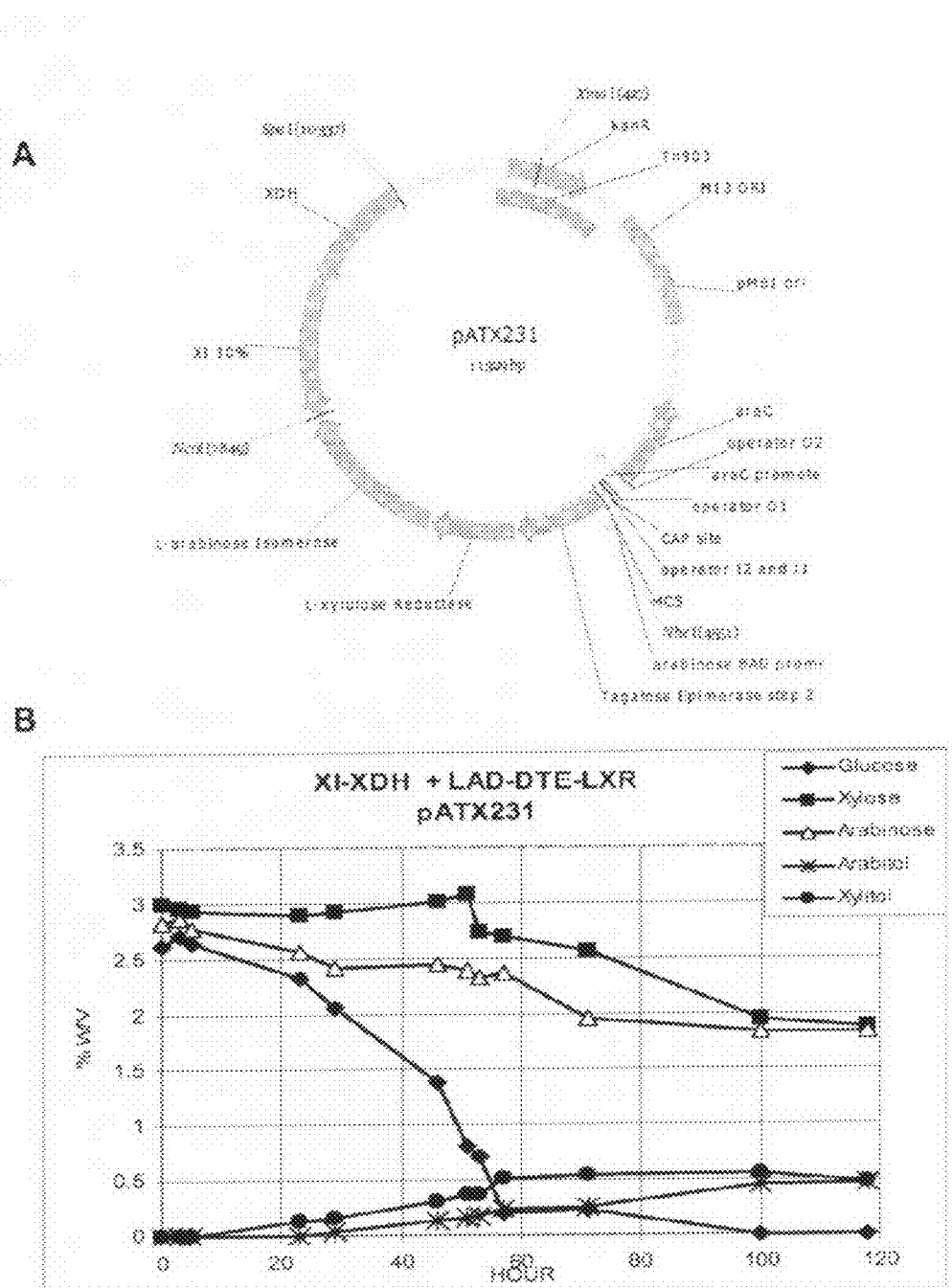
FIG. 7: Conversion of a C-5 mixture to xylitol with ZUC142 (A) containing a plasmid with combined genes for Pathway B and Pathway C (pATX231); and (B) bioconversion to xylitol and arabitol.

Another combination of pathways is to use Pathway B (XI,XDH) for D-xylose conversion and pathway C (LAI, DTE, LXR) for L-arabinose conversion. Plasmid pATX231 and pATX231b were constructed with these combined pathways. These vectors were created by insertion of XDH and mutant XI into pATX210 as shown below in either the same orientation as the arabinose operon or in the reverse orientation. As seen in FIG. 7(A) the resulting recombinant strains produced xylitol although grew slowly and produced L-arabitol during bioconversion despite neither of the individual pathways producing L-arabitol on their own (FIG. 7(B)).

C. Reduce D-xylose, Metabolize Arabinose

1. Conversion of C-5 Mixture to Xylitol Using Xylose Reductase in a Host that Metabolizes Arabinose.

Results of 2-stage bioconversion suggested the possibility that a system that produced xylitol with very little arabitol production could be generated by using a feedstock with a higher ratio of xylose:arabinose, although one that is still typical of many agricultural biomass products, and optimizing certain conditions. In this approach, the arabinose is metabolized as primary carbon source for the bioconversion.

To assess this method, the XR gene was placed in a host with wild type arabinose metabolism. *E. coli* strain ZUC170 was created from *E. coli* B of the genotype F-ompT hsdSB (rB-mB-) gal dcm by transformation with the plasmid based vector pTRP-200 carrying NcXR and selection of the plasmid borne kanamycin resistance marker.

Figure 8:
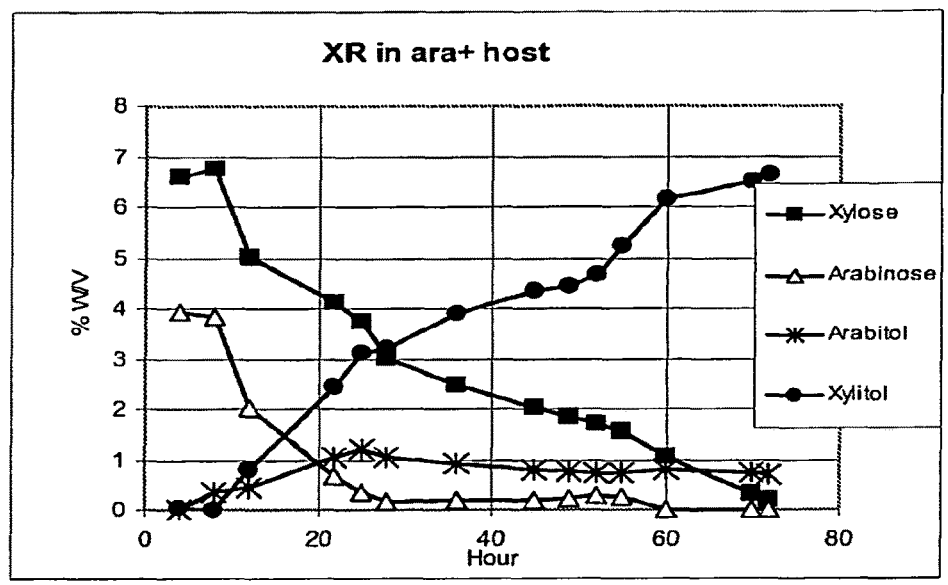
FIG. 8: Production of xylitol from biomass hydrolyzate in a single stage bioconversion using an Ara+ Strain.

This strain was then tested with a synthetic hemicellulose containing a mixture of 6.8% xylose and 4% arabinose, a typical ratio for corn fiber hydrolysates. In a 72-hour bioconversion the yield of xylitol from xylose was excellent, more than 90%, and yielded 66 g/L, while less than 17.5% of arabinose was converted to arabitol at <7 g/L. Thus the final ratio of xylitol to arablitol was more than 8:1. Only a small amount of glucose was added, about 53 hours, which appeared to stimulate conversion. (FIG. 8)

A similar result was obtained using a strain, created in the same way as ZUC170, but with a more xylose specific xylose reductase created (VMQCI). With this strain (ZUC172) in the same xylose:arabinose mixture, more than 90% of xylose was converted to xylitol while 19.5% of arabinose was converted to arabitol at 6.9 g/L and a final ratio of more than 8:1.

This approach is especially attractive for hydrolysates with lower arabinose concentrations, such as many agricultural biomass sources (corn fiber, corn cob, etc), woody biomass and any biomass that contains a xylose:arabinose ratio of approximately 3:1 or better. Using this route high concentrations of xylose from many of substrates are expected.

2. Production of Xylitol from a Hemicellulose Hydrolysate.

Figure 9:
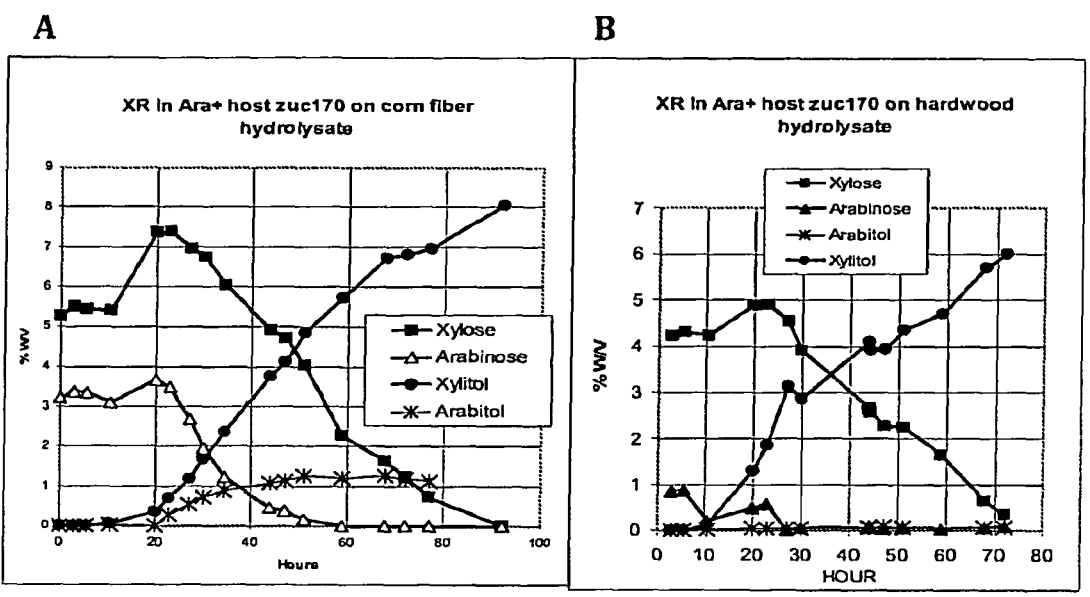
FIG. 9: Efficient conversion of biomass hydrolysate to xylitol with low production of arabitol: (A) corn fiber, (B) hardwood.

Production of xylitol in synthetic hemicellulose does not guarantee the process will work in a more complex and less pure biomass hydrolysate. To test utility of the system the ZUC170 strain fermented on different biomass hydrolysates. FIG. 9 shows results with a hydrolysate from corn fiber and woody fiber sources. Complete conversion was achieved in less than 80 hours to yield xylitol in concentrations between 60-80 g/L. In both cases the hydrolysates had been treated with overliming.

The corn fiber hydrolysate was fermented with a 1:1.5 dilution and grew and converted well. When arabinose was depleted, some glucose was added to maintain reducing power for xylose conversion. A final level of 80 g/L xylitol was achieved with near 100% conversion from xylose. (FIG. 9A)

Other hydrolysates are also suitable. For example, using the same volumes and organism, the hardwood hydrolysate that has a higher xylose to arabinose ratio (11.3% Xylose and 2.2% arabinose) can be used. In this case arabinose was consumed much sooner as there was less of it and thus less arabitol was formed (0.8 g/L vs. 60 g/L xylitol). This bioconversion finished in about 75 hours, and had a shorter lag. In this particular experiment, there was an over-addition of glucose at 44 hours which may have led to a slower bioconversion. Under these conditions very little arabitol was produced in both cases—even in the corn fiber hydrolysate which had significantly more arabinose to start with. (FIG. 9B).

Other hemicellulose hydrolysates such as those from corn fiber, corn stover, corn cob, bagasse, stillage, wheat straw, hardwood, softwood and other biomass sources are suitable.

3. Reduction of Lag Phase

One characteristic of these bioconversion is a lag phase of 12-15 hours at the beginning before xylitol production starts. Several approaches were tried to reduce this time. One approach was to use the broth from a well-grown fermenter at the peak of production, to inoculate a new fermenter.

Broth from fermenter 1 at 32 hours was used to inoculate fermenter 2 with the same medium composition. The second fermenter started producing xylitol without a lag and shows that with the proper inoculum, the bioconversion time can be reduced by about 12-15 hours. Another approach to increasing the rate, especially early in the bioconversion, would be to use a mutant that grows more rapidly in hydrolysate.

A nutrient solution consisting of 5 g tryptone 2.5 g yeast extract, and 1 g dipotassium phosphate was sterilized and added to a sterile fermenter. Corn fiber hydrolysate was detoxified by adding calcium hydroxide to pH 10.5, filtering over Whatman #1 paper, then neutralizing the filtrate with sulfuric acid and filtering again. A portion of this preparation, containing 13.2 g D-xylose, 4.8 g L-arabinose and 5.0 g D-glucose in 120 mL, was added without sterilization, before inoculation. The fermenter was inoculated with 25 ml of an overnight starter culture of ZUC170 grown in LB at 30° C. and run under the following conditions:

| | |
|---|---|
| Temperature | 30° C. |
| pH | 7.0 (NH$_4$OH control) |
| Air | 0.5 LPM |
| Agitation | 800 RPM |
| Volume after inoculation | 315 ml |

Figure 15:
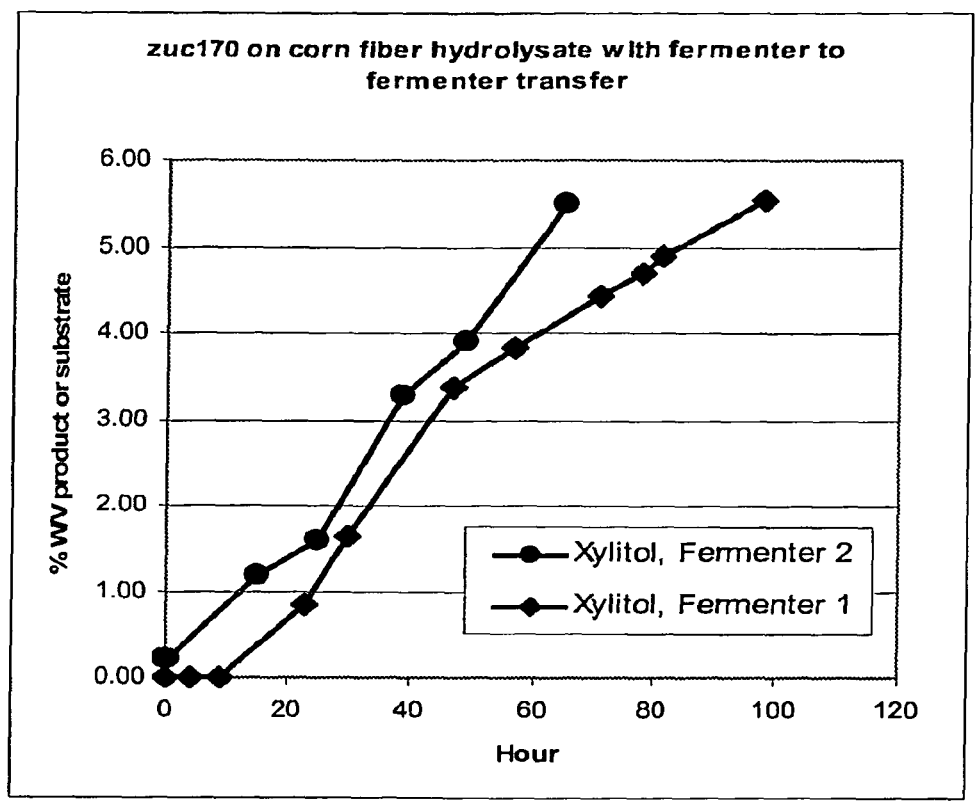
FIG. 15. Action of ZUC170 on corn fiber hydrolysate with fermenter to fermenter transfer.
Figure 17:
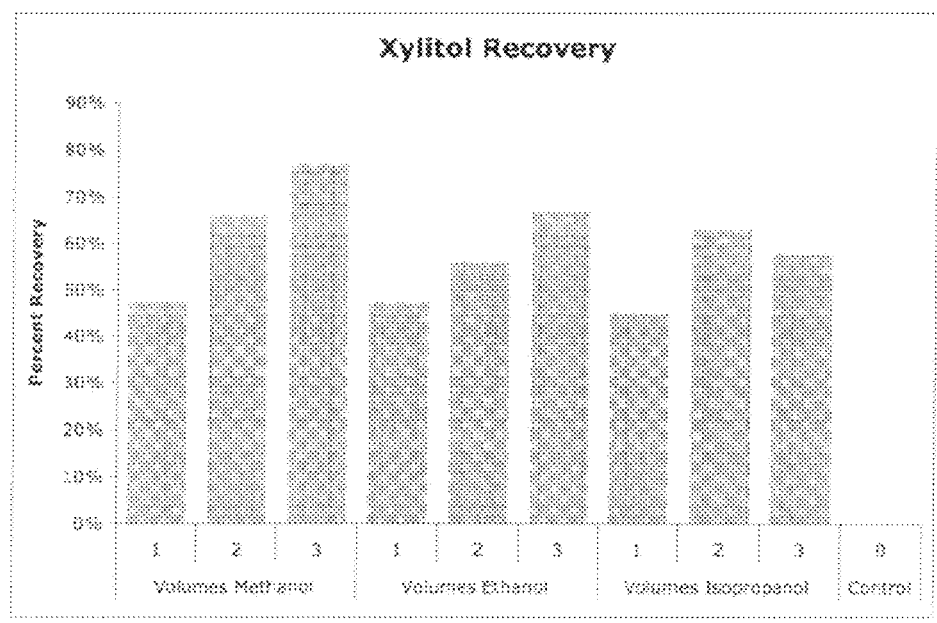
FIG. 17. Xylitol recovery.
Figure 30:
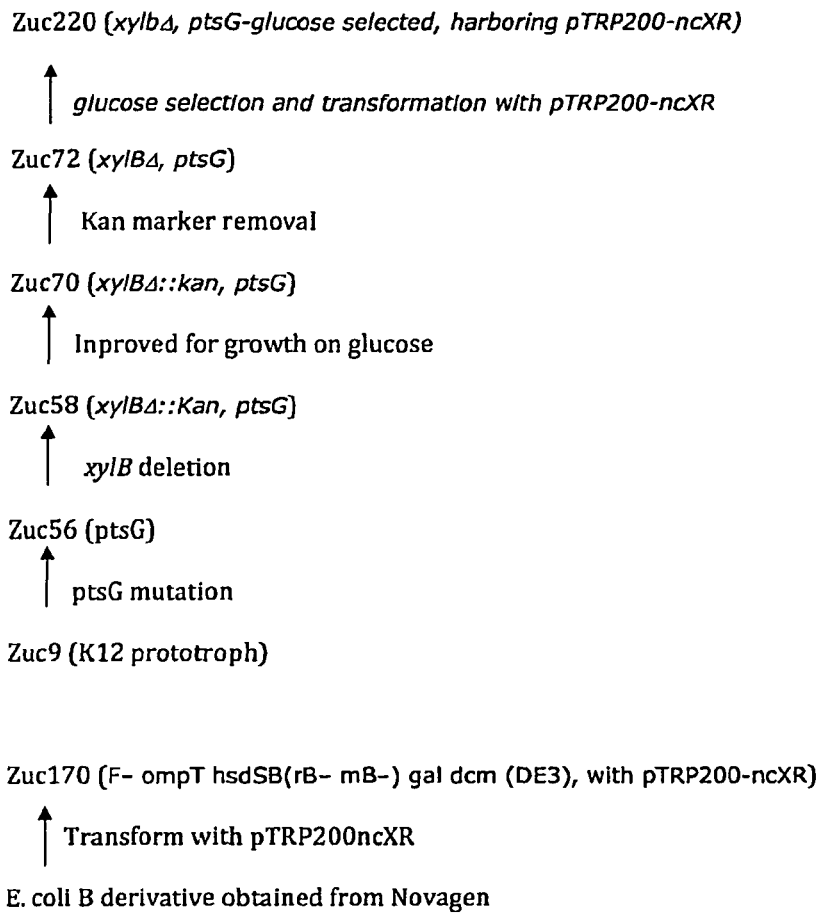
FIG. 30. Strain derivations.
Figure 31:
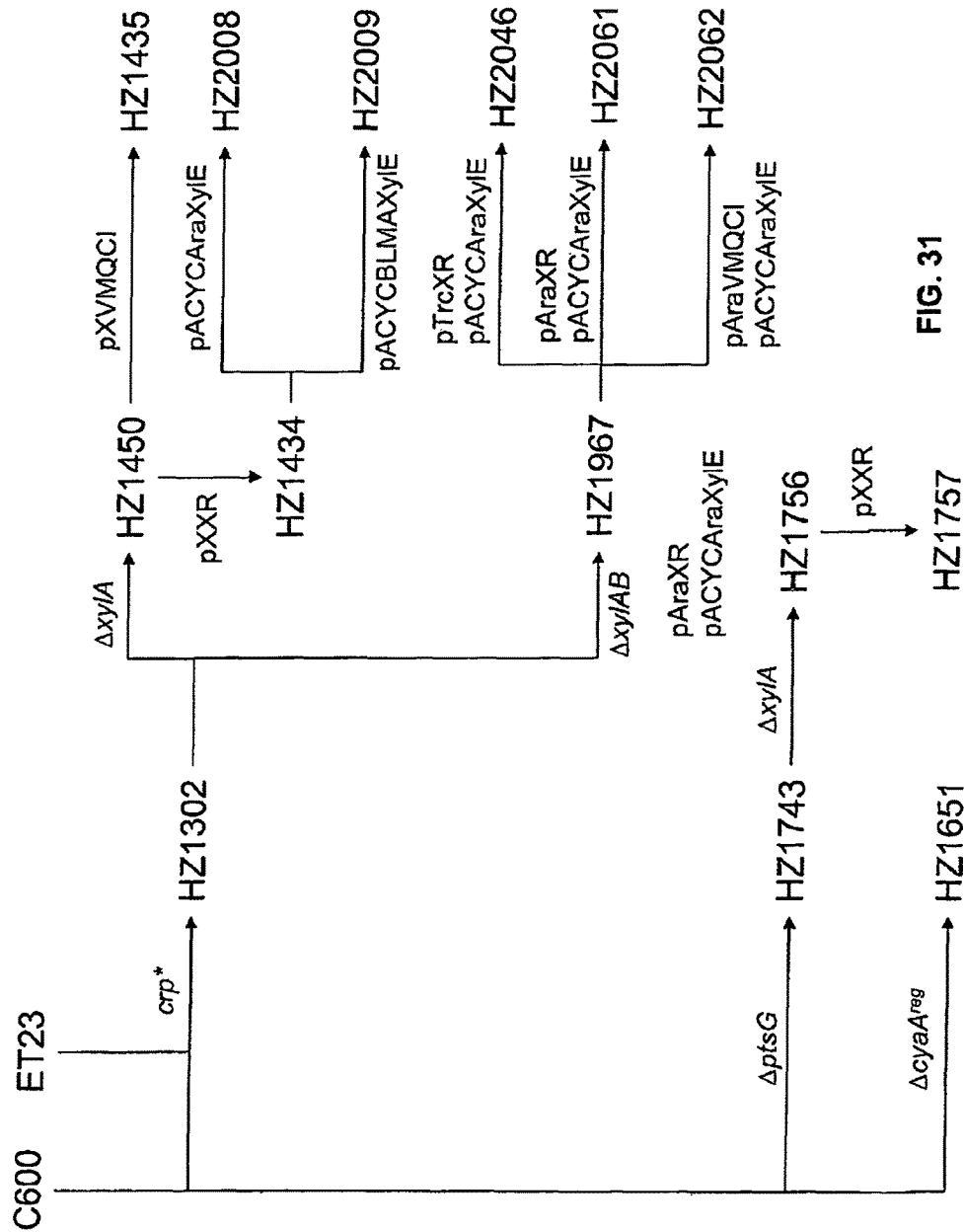
FIG. 31. Diagram of development of HZ strains (see Table 1).

Additional detoxified hydrolysate containing 37.4 g D-xylose, 14.3 g L-arabinose and 13.6 g D-glucose in 340 mL was fed from 16-71 hours. Also, additional D-glucose, 124 g in 200 mL, was added from 24-98 hours. Growth and xylitol production initially lagged with no xylitol produced in the first 15 hours (FIG. 15, Fermenter 1). Then xylitol production began and continued until 46 g xylitol was produced in 98 hours in a final volume of 0.83 L. The volumetric productivity of xylitol was 0.56 g/L-h and the yield on glucose was 0.33 g/g.

To demonstrate that the productivity of the culture is not lost during the fermentation and to show the value of a larger inoculum adapted to growth in hydrolysate, a second fermentation (FIG. 15, Fermenter 2) was started using broth from this fermentation as inoculum. The inoculum for the second fermentation was 60 mL taken from the first fermenter 32 hours after inoculation. The second fermenter was run under the same conditions as the first. It produced the same amount of xylitol as first fermenter, but in 65 hours versus 98 hours. This was due to a reduced lag period and an increased rate.

4. Converting Xylose to Xylitol and Metabolizing; Reduce D-Xylose by Novel Microorganisms to Produce Xylitol A xylose reductase (XR) was previously isolated from the filamentous fungus *Neurospora crassa*. The enzyme has an innate 2.4-fold preference for D-xylose over L-arabinose. Resting cell studies in recombinant *E. coli* expressing this enzyme demonstrated that such a small difference in selectivity was sufficient to improve the ratio of xylitol-to-arabinitol produced. To increase the selectivity of the process toward xylitol, the XR for decreased L-arabinose reductase activity was engineered, and via several rounds of directed evolution, a mutant designated VMQCI was isolated that had a 50-fold lower catalytic efficiency toward L-arabinose. This mutant retained <2% of its original L-arabinose reductase activity. Resting cell studies with this mutant revealed that although the amount of L-arabinitol was significantly decreased, it was not completely eliminated. In order to further increase the selectivity of this biocatalytic process, an orthogonal strategy was implemented to reduce final L-arabinitol titer. For this purpose a metabolically engineered *E. coli* strain was created that is highly efficient at utilizing L-arabinose as a carbon source, and able to sequester it away from XR, decreasing L-arabinitol production.

By combining the engineered protein with a metabolic engineering strategy—a combination that is contemplated creates biocatalysts with novel properties and syngerism.

Xylitol can be made from a better than 1:1 ratio of xylose to arabinose. Fermenting microorganisms were sought to facilitate xylitol production. Of particular concern is the need to reduce arabinitol to a negligible amount, or to convert arabinose to xylitol. Some microorganisms have been reported to achieve these goals but have limitations. One of the major obstacles to creating a strain that is highly efficient at utilizing L-arabinose as a carbon source, is that the regulation of various catabolic pathways of *E. coli* in the presence of multiple sugars is not well understood. This is particularly important for selective production of xylitol from hemicellulosic hydrolysate since corn fiber consists of D-xylose, L-arabinose, and D-glucose. While diauxic growth patterns due to glucose repression in *E. coli* is well studied, little is known about the relative preference between pentoses, and even less in the presence of glucose. In addition, a system used to overexpress XR is IPTG (isopropyl-β-D-thiogalctopyranoside)-dependent, which is reliant on the lactose system, introducing a fourth regulatory system. Considering that the transport of all three non-glucose sugars is dependent on CRP (cyclic adenosine monophosphate receptor protein), significant cross-talk between them is to be expected. Glucose de-repression for simultaneous uptake of two sugars has been documented previously, albeit primarily for ethanol production, which was carried out under oxygen-limited conditions. The pleiotropic effects on other regulatory systems of such de-repressed mutants are poorly characterized.

To engineer *E. coli* for efficient L-arabinose catabolism in the presence of glucose and D-xylose, three different de-repression strategies were used: a glucose phosphotransferase mutant, a regulation deficient adenylate cyclase mutant, and a CRP mutant (Goerke and Stulke, 2008). The crp* mutant can be superior among the three under certain conditions. This mutant was previously described to be helpful in co-utilization of D-xylose and glucose for the production of xylitol using an IPTG induction system. In this strain, the effects of overexpressing a xylose transporter (XylE) were tested as well as the relative productivity of placing XR under the control of D-xylose-, IPTG-, and L-arabinose-inducible systems. Under certain conditions, L-arabinose was preferred over glucose, whereas under other growth conditions glucose was the preferred carbon source. Finally, in a bioreactor setting, the engineered strain in conjunction with the mutant XR (VMQCI) was able to eliminate L-arabinitol production from an equiweight mixture of D-xylose, L-arabinose and glucose.

Under Some Conditions Using the 1:1 Mixture of Arabinose:Xylose the crp* Mutant is the Most Efficient at Co-Utilizing Three Sugars for Xylitol Production.

Three different catabolite de-repression strategies HZ1743, HZ1651 and HZ1302 (ΔptsG, ΔcyaAreg, and crp*, respectively were tested for co-utilization of glucose, D-xylose and L-arabinose. The phosphotransferase system (PTS) for simultaneous glucose uptake and phosphorylation has been shown to play a role in catabolite repression (Goerke and Stulke, 2008). Strains with inactivated permease, PtsG, were shown to relieve the repression and have been used for co-fermenting mixed sugars (Nichols et al., 2001). Adenylate cyclase (CyaA) is responsible for forming cAMP in response to low glucose concentrations. Its activity is regulated by interaction with the PTS protein Enzyme HAGlc. A strain with truncated CyaA was shown to be de-regulated and did not demonstrate diauxic behavior when grown in glucose and maltose mixtures (Crasnier et al., 1994). Several CRP (also known as CAP, catabolite activator protein) mutants have been isolated that show de-repressed behavior (Eppler and Boos, 1999; Karimova et al., 2004; Zhu and Lin, 1988). For the present disclosure, the CRP mutant that was shown to de-repress xylose metabolism under aerobic conditions for xylitol production, was used (Cirino et al., 2006; Eppler and Boos, 1999).

Deletions were created by replacing the undesired locus with PCR amplified cat (CmR) mediated by λ red recombinase proteins (Datsenko and Wanner, 2000), either directly in the parent strain, or in MG1655 and then transduced into the appropriate recipient Miller, 1992). The CRP mutant was created by transduction of donor allele from ET23 into C600 (Eppler and Boos, 1999; Miller, 1992).

Figure 10:
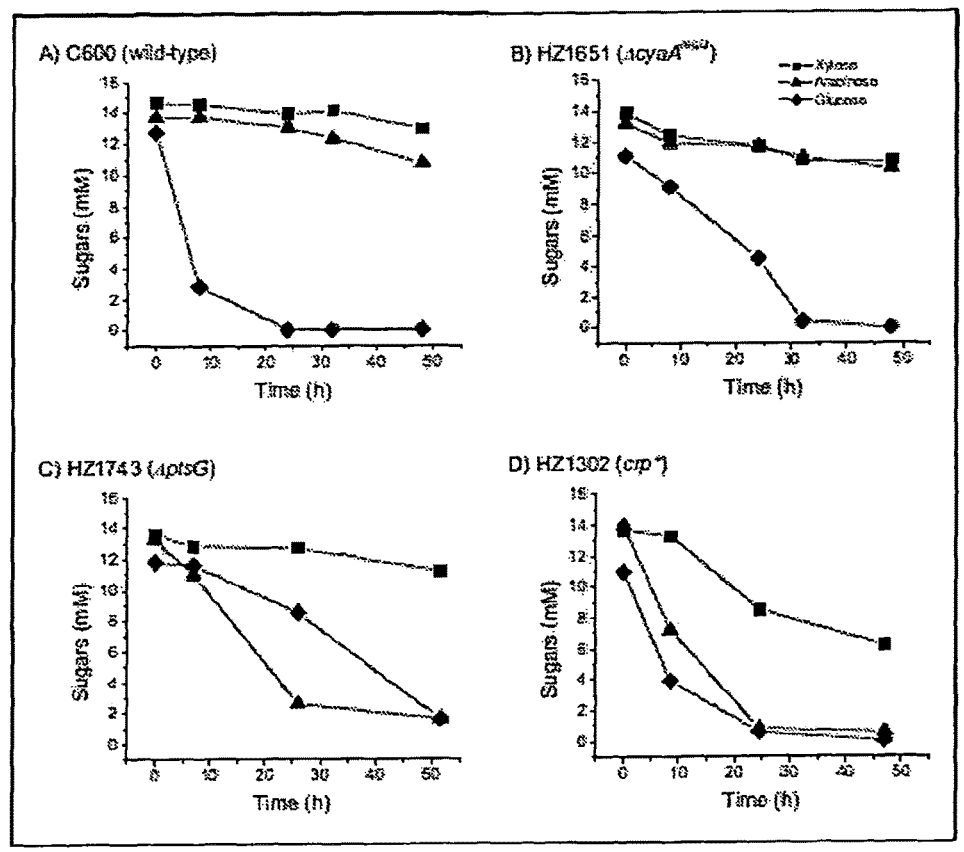
FIG. 10. Growth of various strains in D-glucose, D-xylose, and L-arabinose to test for catabolite repression at 30° C. (A) Wild-type *E. coli* K-12 C600 shows strong diauxie, with quick utilization of D-glucose first. (B) Deletion of the regulatory domain of adenylate cyclase (HZ1651, $\Delta cyaA^{regul}$) resulted in slightly less pronounced diauxie, although pentose assimilation is still slower than D-glucose. (C) D-Glucose permease knockout (HZ1743, $\Delta ptsG$) strain showed efficient L-arabinose and D-glucose utilization, although D-xylose was relatively slower. (D) The mutant CRP (HZ1302, crp*) showed the most efficient co-utilization of all three sugars. All experiments were also performed at 37° C. to ascertain D-glucose de-repressed phenotype.
Figure 11:
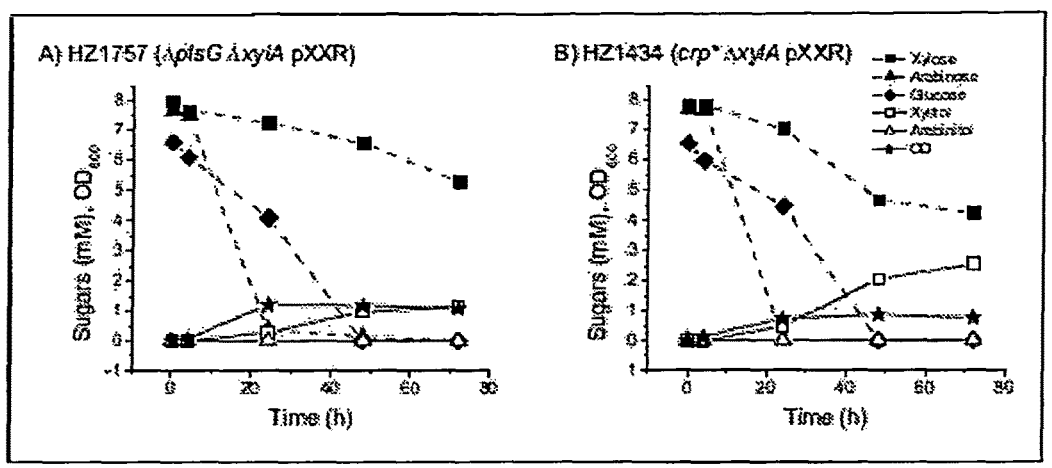
FIG. 11. Xylitol production in shake flasks comparing (A) HZ1757 ($\Delta ptsG$ $\Delta xylA$ pXXR) and (B) HZ1434 (crp* $\Delta xylA$ pXXR SEQ ID NO: 6) diauxie relief strategies. Although both strains demonstrate simultaneous glucose and L-arabinose assimilation, stronger induction of the xylose pathway results in higher xylitol production using XR under XylA promoter in HZ1434. Neither of the two strains produces significant amounts of L-arabinitol. Data are an average of two independent experiments and error is less than 15% in all cases. Experiments were also performed with mutant VMQCI, (SEQ ID NO: 19 and 20) and similar results were obtained.

These three recombinant strains plus the wild type strain were grown in minimal medium with ~2 g/L each of glucose, D-xylose and L-arabinose under oxygen-limited conditions. Supernatants were analyzed at various time points to ascertain their sugar utilization patterns (FIG. 10). The wild-type C600 (FIG. 10A) demonstrated strong diauxie, with almost no uptake of D-xylose or L-arabinose until complete depletion of glucose. The strain with truncated CyaA (HZ1651) (FIG. 10B) showed slightly decreased glucose assimilation, although pentose utilization was not significantly improved. The PtsG knockout (HZ1743) (FIG. 10C) demonstrated delayed response to glucose, but was able to uptake L-arabinose and glucose simultaneously, albeit with differing rates. Finally, the crp* mutant (HZ1302) (FIG. 10D) showed efficient simultaneous assimilation of all three sugars, although, as in all strains, xylose uptake was the slowest. Based on these data, HZ1651 was deemed unsuitable for xylitol production. After deletion of XylA in HZ1743 and HZ1302 to prevent xylose catabolism, pXXR (wtXR under XylA promoter) was transformed into both strains to give HZ1757 (FIG. 11A) and HZ1434 (FIG. 11B), respectively, and tested for xylitol productivity. Although both strains demonstrated efficient utilization of glucose and L-arabinose as carbon sources, the stronger induction from xylose promoters in HZ1434 is evident from higher xylose conversion to xylitol. Based on these experiments, the crp* mutant strain was used for further engineering work Crabtree Effect is Prevalent at High Sugar Concentrations in the Crp* Strain Glycolysis rate at high sugar concentrations often exceeds respiratory capacity, leading to build-up of intermediate metabolites. This "Crabtree effect" is well-known for many organisms including *S. cerevisiae* and *E. coli*, which are known to build up ethanol and acetate, respectively. In *E. coli* acetate build-up decreases growth rate as well as recombinant protein production. Previous work in a similar crp* strain showed that at 18 g/L glucose concentration, acetate production is significant, accumulating to 70 mM.

Figure 12:
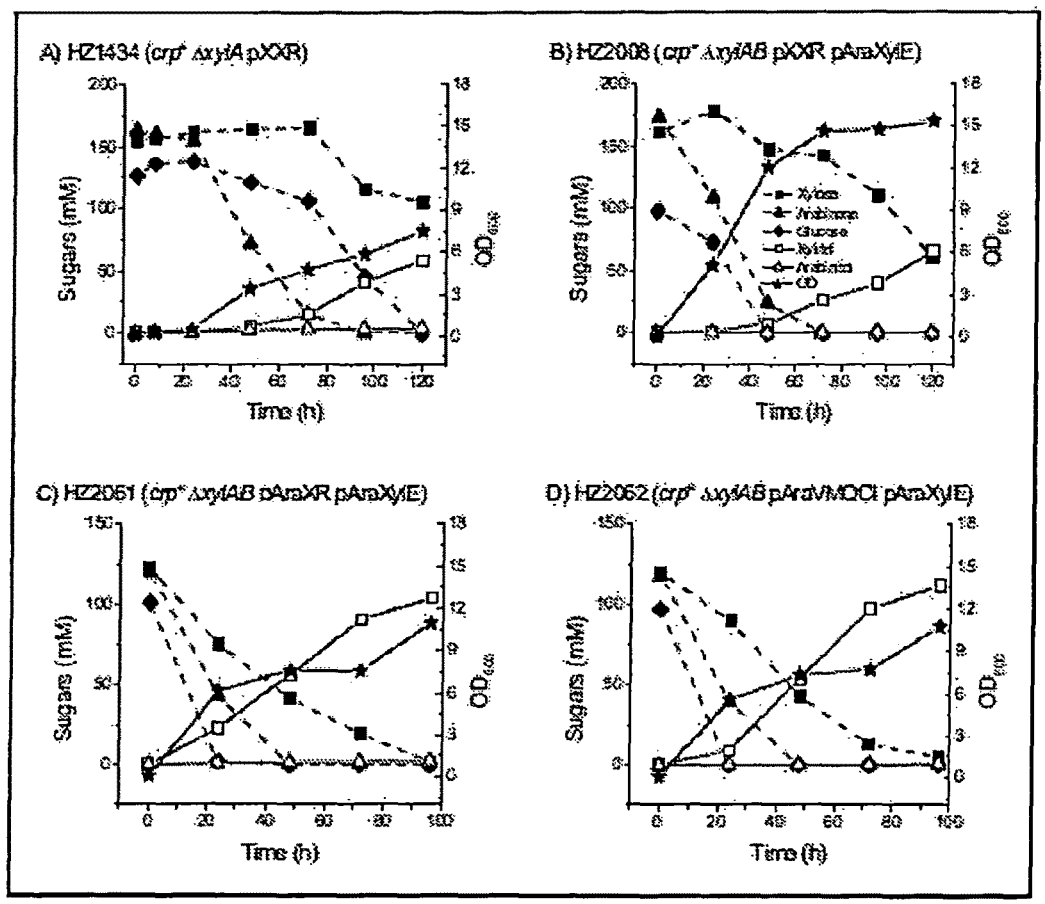
FIG. 12. Strategies implemented to improve xylitol productivity. (A) pH-stat bioreactor allows cells to completely and efficiently catabolize L-arabinose and glucose simultaneously. XR expression is under control of the XylA promoter (HZ1434). (B) Concurrent expression of xylose-proton symporter (XylE) using AraBAD promoter decreases lag phase, but also decreases L-arabinose assimilation rate relative to glucose (HZ2008). Xylitol productivity does not increase significantly, however. (C) Expression of XR using AraBAD promoter instead of XylA promoter promotes near-stoichiometric conversion of D-xylose to xylitol (HZ2061). (D) Expression of the mutant XR, VMQCI, eliminates L-arabinitol production, although initial xylitol productivity also drops slightly (HZ2062). Data are an average of two independent experiments and error is less than 15% in all cases.
Figure 13:
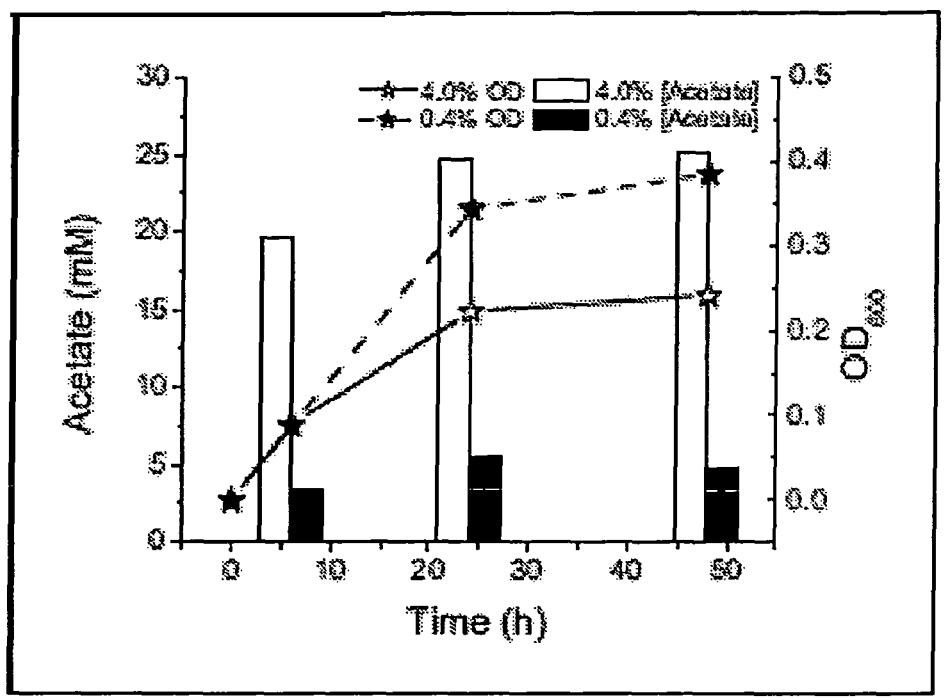
FIG. 13. Acetate production by HZ1434 during growth in 4% and 0.4% usable sugars (glucose+L-arabinose). Cells grown in high concentrations of sugars succumb to Crabtree effect and produce large amounts of acetate (~25 mM), which inhibits cell growth, resulting in decreased final cell density. Data points are shown at 0, 6, 24, 48 h, and are an average of two independent experiments and error is less than 15% in all cases.

When HZ1434 was grown in 40 g/L total usable sugar (glucose+L-arabinose) in minimal M9 medium, pH dropped to ~5 within 24 hours, completely inhibiting growth due to high level acetate production (FIG. 12). Addition of 50 mM MOPS (4-morpholinopropanesulfonic acid) to the medium could not buffer the pH at 7.0, as had been done previously at 18 g/L glucose. Addition of a complex nitrogen source has been shown to reduce acetate production in batch cultures (Panda et al., 2000). However, addition of 10 g/L tryptone did not prevent acid accumulation. Although genetic methods exist to decrease acetate production pleiotropic effects could lead to additional complications. Therefore, a pH-stat bioreactor was used subsequently.

Expression from Arabinose Promoter Decreases Crabtree Effect and Lag Phase

In the pH-stat bioreactor with 60 g/L total sugars (equiweight D-xylose, L-arabinose, and glucose), there was a ~24 h lag phase. In addition, xylitol production was minimal until near-complete depletion of L-arabinose in the medium (FIG. 12A). Poor induction of the xylose pathway compared to the arabinose operon (FIG. 10D) was likely the primary reason for low productivity. Since overexpression of xylose-proton symporter (XylE) was shown to transport D-xylose efficiently in glucose-xylose mixtures (Khankal et al., 2008), it may help increase xylitol productivity. Expression using a constitutive promoter, BLMAp (Kim et al., 2003) using pACYCBLMAXylE in HZ2009 (Table 1), did not improve xylitol conversion (data not shown). On the other hand, expression of XylE under the AraBAD promoter from a multicopy plasmid (pACYCAraXylE) (SEQ ID NO: 21) had the unexpected side-effect of simultaneously decreasing both the lag phase of HZ2008 and the total amount of alkali required to maintain pH at 7.0 (FIG. 12B). Unfortunately, the xylitol productivity was nearly unaltered. Another side-effect of this is the change of the relative rates of glucose and L-arabinose consumption. Prior to XylE overexpression (HZ1434), L-arabinose was assimilated faster than glucose (FIG. 11B, 12A), whereas after its overexpression (HZ2008), glucose was the preferred carbon source (FIG. 12B). It is a possible that promoter dilution may play a role in decreasing expression from the chromosomal araBAD operon, although previous reports indicate that this phenomenon is not significant in bacteria. Alternately, the presence of XylE in the cell membrane either replacing AraF and AraGFH transporters, or in addition to them, could be retarding the rate of L-arabinose uptake. This could also explain the lower requirement for alkali in the bioreactor, since the respiration rate would be more capable of keeping up with the slower glycolysis of L-arabinose.

Since overexpression of XylE did not improve the final xylitol titer, the poor productivity was likely due to low expression of XR under the control of XylA promoter, despite its extremely high activity. So, XR was placed under either the IPTG-inducible Trc promoter (pTrcXR) or the AraBAD promoter (pAraXR). Induction from a lac-based promoter in crp* strain in glucose-xylose mixtures was previously shown to produce high levels of recombinant protein, even at 100 µM concentration (Cirino et al., 2006). However, expression of XR from the Trc promoter induced with 100 µM IPTG led to even poorer conversion than that obtained using the XylA promoter (HZ2046, data not shown). Under the AraBAD promoter (HZ2061), xylitol production reached near stoichiometric levels, with low levels of L-arabinitol production as well (2-6 mM, FIG. 12C). The VMQCI mutant produced xylitol at a slightly slower rate than wtXR (HZ2062), as would be expected from the lower overall activity of the mutant (FIG. 12D), but it produced undetectable levels of L-arabinitol over the 4 day period (limit of detection <1 mM).

Catabolic Pathways: Activation and Competition

Catabolic pathways for sugars other than glucose are normally repressed in its presence. Four different strategies for de-repression were tested and the crp* mutant was the most efficient at simultaneously activating the D-xylose and L-arabinose metabolic pathways (FIG. 10). However, the arabinose pathway was more strongly activated, as evident from quicker uptake and assimilation compared to D-xylose. Using XR as a reporter under the control of arabinose (AraBAD), xylose (XylA), or lactose (Trc) promoter systems, AraBAD was the most strongly expressed among all three. Although the lac-based system was shown to be fully activatable with 100 µM IPTG in crp* strains in the presence of glucose and D-xylose (Cirino et al., 2006), in the presence of three sugars, this promoter was weakly induced. This is true even in light of the fact that IPTG is the only non-transformable inducer tested. In a non-crp* strain, there is strong activation of D-xylose, L-arabinose, and lactose operons simultaneously in the absence of glucose. Lee and coworkers (2007) have shown that presence of IPTG represses AraBAD promoter activation.

In contrast to these observations, in the crp* strain created here, the exact opposite was found—AraBAD repressed activation from IPTG-dependent promoters. Investigations into the mechanism of competition and cross-talk between the regulation of three non-glucose operons in wild-type and crp* strains in the presence or absence of glucose would help explain the behavior seen here. The roles of sugar-specific transporters and transcription activators/repressors, in particular, would reveal the mechanism of these interactions. The combination of protein engineering and metabolic engineering led to synergistic increase in desired biocatalytic properties. In this particular case, the synergy was manifested as increased selectivity such that that L-arabinitol production was minimal.

To realize this goal, a metabolically engineered E. coli strain was created that is highly efficient at utilizing L-arabinose as a carbon source, and able to sequester it away from XR, decreasing L-arabinitol production. One of the major obstacles to create such a strain was that the regulation of various catabolic pathways of E. coli in the presence of multiple sugars is not well understood. This is particularly important for selective production of xylitol from hemicellulosic hydrolysate because corn fiber consists of D-xylose, L-arabinose, and D-glucose. Although diauxic growth pattern due to glucose repression in E. coli is well studied, little is known about the relative preference between pentoses, and even less in the presence of glucose. In addition, a system described herein to overexpress XR is IPTG (isopropyl-β-Dthiogalctopyranoside)-dependent, which is reliant on the lactose system, thus introducing a fourth regulatory system. Considering that the metabolism of all three non-glucose sugars is dependent on activation by CRP (cyclic adenosine monophosphate receptor protein), significant cross-talk between them is to be expected. Glucose de-repression for simultaneous uptake of two sugars has been documented previously, albeit primarily for ethanol production, which was carried out under oxygen-limited conditions (Lindsay et al., 1995; Nichols et al., 2001). The pleiotropic effects on other regulatory systems of such de-repressed mutants are poorly characterized.

L-arabinitol production can be almost completely eliminated from an equiweight mixture of D-xylose, L-arabinose, and glucose—the three major sugars in hemicellulosic hydrolysate. Considering actual corn hemicellulose has D-xylose to L-arabinose in a ~5:3 ratio, the tested equiweight mixture is a worst-case scenario. This strategy used an engineered E. coli strain with glucose depressed growth and xylose transporter overexpression to quickly assimilate L-arabinose as a carbon source, sequestering it away from the substrate selective XR mutant VMQCI. Not only is L-arabinose prevented from being converted to L-arabinitol, it also provides reducing equivalents in the form of NADPH for xylitol production, and acts as an inducer for protein expression.

5. Improved Strain (ZU220) for Conversion of Hemicellulose to Xylitol

A new strain with significant improvement in yield of xylitol per gram of glucose and per gram of base was developed and named ZUC220. ZUC220 (xylBΔ, ptsGΔ-glucose selected pTRP200-ncXR) was created by PCR-based genetic deletion of xylB and ptsG from starting strain AB707 (K12 prototroph), followed by selection on glucose containing minimal medium for several generations, and then the resulting strain was transformed with pTRP200-ncXR (constitutive expression vector containing ncXR).

The volumetric productivity of ZUC220 is higher than ZUC170.

Use of ZUC220 on Synthetic Mixture of Sugars

| | |
|---|---|
| Tryptone | 14 g |
| Yeast extract | 7 g |
| Potassium phosphate, dibasic | 4.2 g |
| Sodium chloride | 7 g |
| Magnsesium sulfate | 2 g |
| Water | 750 mL |
| Antifoam Cognis Clerol FBA 3107 | 3 drops |

The vessels were sterilized with the above media in situ. D-xylose (30 g) and D-glucose (30 g) was sterilized in 100 ml water separately and added prior to inoculation of the vessel. The fermenters were inoculated with 50 ml of an overnight starter culture grown in LB at 30° C. and run under the following conditions:

| | |
|---|---|
| Temperature | 30° C. |
| pH | 7.0 (NH$_4$OH control) |
| Air | 1 LPM (1 VVM) |
| Agitation | 800 RPM |
| Volume after inoculation | 900 ml |

Figure 14:
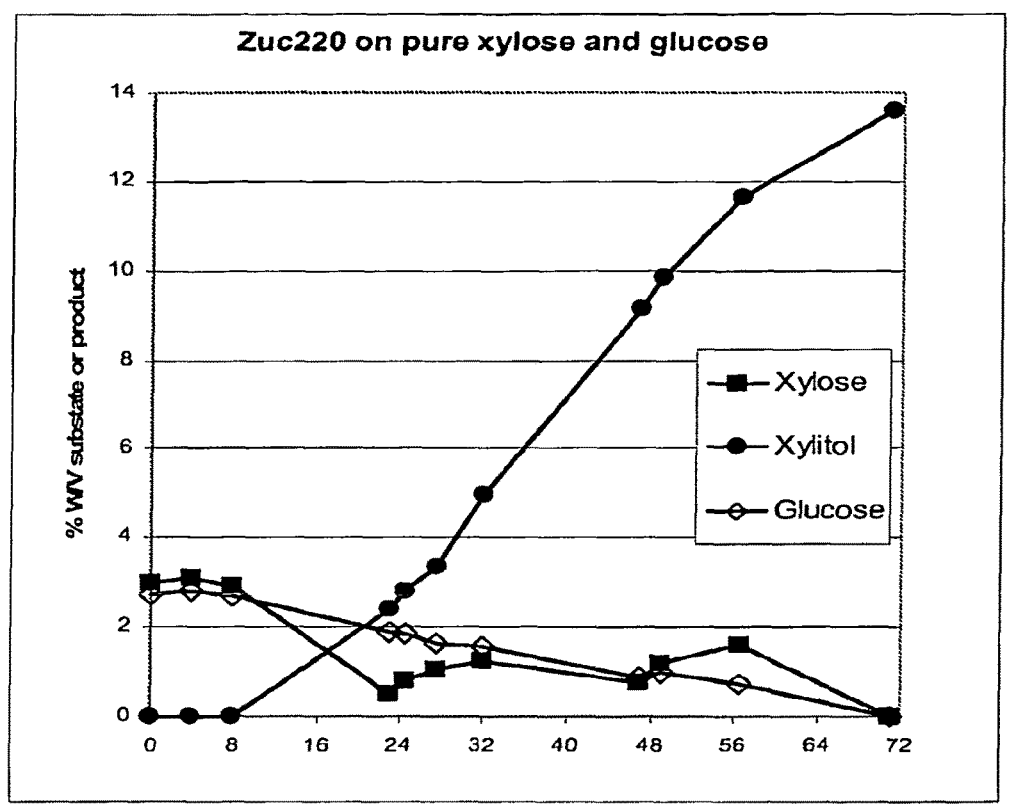
FIG. 14. ZUC220 with synthetic hydrolysate.

A feed of D-xylose (130 g) and D-glucose (40 g) was dissolved in 185 ml water, sterilized and used to feed the fermentation from 23-56 hours after inoculation. The result was 156 g xylitol produced in 71 hours in a final volume of 1.145 L (136 g/L concentration (FIG. 14A). The volumetric productivity was 1.92 g/L-h, nearly twice the rate previously obtained with ZUC170 (FIG. 8). The yields on glucose and base were 2.48 g xylitol per g glucose and 46 g xylitol per g NH$_4$OH.

The medium was sterilized and added to a sterile fermenter. Corn fiber hydrolysate was detoxified by adding calcium hydroxide to pH 10.5, filtering over Whatman #1 paper, then neutralizing the filtrate with sulfuric acid and filtering again. A portion of this preparation, containing 13.2 g D-xylose, 4.8 g L-arabinose and 5.0 g D-glucose in 120 mL, was added without sterilization, before inoculation. The fermenter was inoculated with 25 ml of an overnight starter culture of ZUC170 grown in LB at 30° C. and run under the following conditions:

| | |
|---|---|
| Temperature | 30° C. |
| pH | 7.0 (NH$_4$OH control) |

-continued

| | |
|---|---|
| Air | 0.5 LPM |
| Agitation | 800 RPM |
| Volume after inoculation | 315 ml |

Additional detoxified hydrolysate containing 37.4 g D-xylose, 14.3 g L-arabinose and 13.6 g D-glucose in 340 mL was fed from 16-71 hours. Also, additional D-glucose, 124 g in 200 mL, was added from 24-98 hours. Growth and xylitol production initially lagged with no xylitol produced in the first 15 hours (FIG. 14B, Fermenter 1). Then xylitol production began and continued until 46 g xylitol was produced in 98 hours in a final volume of 0.83 L. The volumetric productivity of xylitol was 0.56 g/L-h and the yield on glucose was 0.33 g/g.

To demonstrate that the productivity of the culture is not lost during the fermentation and to show the value of a larger inoculum adapted to growth in hydrolysate, a second fermentation (FIG. 14B) was started using broth from this fermentation as inoculum. The inoculum for the second fermentation was 60 mL taken from the first fermenter 32 hours after inoculation. The second fermenter was run under the same conditions as the first. It produced the same amount of xylitol as first fermenter, but in 65 hours versus 98 hours. This was due to a reduced lag period and an increased rate.

II. Crystallization

A. Xylitol with Cosolvents.

In order to test the effect of co-solvents on crystallization of xylitol, a 50% solution of xylitol was separated into 10 mL aliquots and various quantities of cosolvents (methanol, ethanol, and isopropanol) were added. The mixtures were allowed to crystallize overnight at −20° C. and inspected. Only a small (<10%) amount of crystallization was noted. A separate experiment was carried out using the same methodology, but with seeding using 1 mg of finely ground xylitol crystals. After overnight crystallization, significant xylitol crystallization was obtained. These crystals were removed by filtration, washed with a small amount of cosolvent, dried, and the mass was recorded. The various recoveries are displayed in FIG. 25. The best recovery was approximately 80% of the initial xylitol in solution in a single stage of crystallization using 3 volumes of methanol. A control containing no cosolvent did not result in any xylitol formation. These initial conditions are very promising and should afford the desired yield of recovery.

B. Methods.

Crystallization from bioconversion broths can be achieved in a number of ways. One way is to subject the bioconversion broth to charcoal treatment, followed by concentration of the xylitol-containing broth to a xylitol concentration of around 700 g/L. Treatment of concentrated bioconversion broth with cation exchange calcium affinity chromatography helps speed the crystallization. To date a single simple chromatography step helps remove salts and other byproducts and improves crystallization. As high as 80% recovery was achieved with the final material meeting the desired purity specifications. Recovery can include some or all of the following steps:

Cell removal. Microfiltration, centrifugation, or vacuum filtration is required (rotary drum filter).

Charcoal treatment. The cell-free broth is mixed with 5 g/L activated charcoal. Mixing is continued for 1 hour at 37° C., and then the charcoal is separated by filtration on a filter press. Alternatively, a charcoal column can be used.

Evaporation. The volume is reduced by removing 80% of the volume by evaporation under vacuum at 55-60° C. Target, 500-700 g/L xylitol. An efficient multistage evaporator is required.

Cation exchange. To remove salts and other byproducts.

Crystallization. The concentrate is cooled to induce crystallization. A crystallizer is required. Crystallization may be induced by addition of seed crystals or alcohol cosolvent such as methanol, ethanol, or isopropanol.

Crystal collection and washing. A basket centrifuge or Nutsche filter is required. The crystals are collected and washed free of impurities.

Drying. A fluid bed dryer can be used.

Recrystallization. If needed, the xylitol can be further purified by undergoing a recrystallization process.

Supplemental Materials and Methods

Materials

All media were purchased from Becton-Dickinson (BD, Sparks, Md.), chemicals from Sigma-Aldrich (St. Louis, Mo.), enzymes from New England Biolabs (NEB, Beverly, Mass.), and oligonucleotide primers from Integrated DNA Technologies (IDT, Coralville, Iowa). All DNA purification kits were obtained from Qiagen (Valencia, Calif.), except that the Wizard® Genomic DNA Purification Kit was procured from Promega (Madison, Wis.). Cells were maintained on Lysogeny Broth (LB) plates containing 1.5% agar and the appropriate antibiotic. Selection for plasmid maintenance was done with ampicillin (100 mg/L), chloramphenicol (25 mg/L), and kanamycin (50 mg/L). Chromosomal integrants were selected on chloramphenicol (6 mg/L) or tetracycline (10 mg/L) LB plates.

Plasmid Construction

All cloning work was performed in E. coli DH5α or WM1788 (pir+ for propagating R6K plasmids), and a list of constructs can be found in Table 1. All XR expression plasmids were derivates of pTrc99A. XR and mutants were previously cloned into pACYCDuet (Novagen), and were used as the template for PCR (Nair and Zhao, 2008). The XylA promoter was amplified from E. coli MG1655 genomic DNA, and spliced with XR using overlap extension PCR. The cassette was digested with NsiI and BglII and ligated into pTrc99A that had been digested with NsiI and BamHI. Ligation of compatible BglII-BamHI ends abolished both restriction sites. The AraBAD promoter was digested out of pRW2-ptdh (Johannes et al., 2005) using PstI and NdeI; PCR amplified XR was digested with NdeI and BglII, and pTrc99A with NsiI and BamHI. All three were ligated together in a single reaction, which abolished the compatible PstI-NsiI and BglII-BamHI sites. For IPTG inducible constructs, XR (EcoRI-BglII) was directly ligated into EcoRI-BamHI digested pTrc99A. Xylose transporter xylE was amplified from MG1655 genomic DNA and ligated directly into pTKXb-xdh-araB' (Kim et al., 2003; Nair and Zhao, 2008) digested with NdeI and XhoI. The promoter-gene cassette was then digested out with EcoRI and XhoI and ligated in pACYCDuet digested with the same endonucleases. This construct provided expression from the constitutive BLMA promoter. For expression under the AraBAD promoter, xylE was first cloned into pRW2-ptdh between the NdeI and PciI sites. The promoter-gene cassette was then digested out using PstI and PciI and ligated into pACYCDuet digested with PstI and NcoI. The ligation abolished the compatible NcoI-PciI sites.

Genetic Methods

All strains used for xylitol production were E. coli K-12 C600 and its derivates (Table 1), and all deletions were performed using the γ red system (Datsenko and Wanner, 2000). Briefly, PCR product containing the cat gene flanked by FRT (Flp recognition target) and 45-50 nt of sequence identical to the target locus was transformed into cells expressing γ red recombinase proteins (encoded on pKD46). Gene replacement was selected on chloramphenicol plates and verified by functional assay and PCR. The resistance marker was then removed by the expression of Flp recombinases from a then no-inducible promoter on a temperature sensitive plasmid (pCP20). Flp recombinase plasmid loss and cat loss occurred simultaneously and were verified by sensitivity to ampicillin and chloramphenicol. Deletion of ptsG and cyaA$^{regul}$ was performed directly in C600, whereas inactivation of the xylA and xylAB genes was performed in MG1655 and then moved by P1 transduction to the recipient strains (Miller, 1992). The crp* mutation was also generated by P1 transduction from ET23 and selecting for Tet® integrants (Eppler and Boos, 1999). Deletions were verified by PCR using cell lysate as the template and appropriate flanking primers. Verification of glucose de-repression was first done by blue/white screening on LB plates containing 10 g/L glucose. Strong induction of lacZ in the presence of glucose indicated the depressed phenotype. The CyaA mutant strain did not demonstrate significant LacZ activity. Finally, direct monitoring of sugar co-utilization in shake flasks was used to verify de-repression.

HPLC Analysis

Sugar concentrations were quantified using Shimadzu high performance liquid chromatography (HPLC) equipped with a low temperature evaporative light scattering detector (ELSD-LT) (Columbia, Md.). A Bio-Rad Aminex 250×4 mm HPX-87C (Bio-Rad, Hercules, Calif.) carbohydrate column was used to separate the sugars, as per manufacturer's recommendations. The column was run at 0.2 mL/min at 85° C. for 18 minutes with water as the mobile phase.

GC-MS Analysis

Acetate quantification was performed at the Roy J. Carver Metabolomics Center. n-Butanol (1 mL/L) was used as internal standard to quantify acetate in media. Samples (1 µl) were injected in split mode (5:1) to the GC/MS system consisting of an Agilent 7890 gas chromatography, an Agilent 5975 mass selective detector, and HP 7683B autosampler (Agilent Technologies, Palo Alto, Calif.). Acetate samples were analyzed on a 30 in ZB-Wax-Plus column with 0.32 min I.D. and 0.25 µm film thickness Phenomenex, Torrance, Calif.) with an injection port temperature of 250° C., the interface set to 250° C., and the ion source adjusted to 230° C. The helium carrier gas was set at a constant flow rate of 2.5 mL min$^{-1}$. The temperature program was 5 min isothermal heating at 90° C., followed by an oven temperature increase of 10° C. min$^{-1}$ to 210° C. for 2 min. The mass spectrometer was operated in positive electron impact mode (EI) at 69.9 eV ionization energy in m/z 50-550 scan range.

The spectra of all chromatogram peak was evaluated using the HP Chemstation program (Agilent Technologies, Palo Alto, Calif.). Identification was performed using the mass spectra obtained from the authentic standards and additionally confirmed with NIST08 and W8N08 libraries.

Shake Flask and Bioreactor Cultures

For shake flask cultures, overnight cultures were grown at 37° C. in M9 minimal medium supplemented with 2 mM MgSO$_4$, 0.1 mM CaCl$_2$, 20 mg/L leucine, 120 mg/L threonine, 10 mg/L thiamine-HCl, 2 g/L glucose and the appropriate antibiotic(s). 125 mL unbaffled bottles containing 25 mL of the same medium but containing 1-2 g/L of each sugar (glucose, D-xylose, and L-arabinose) were placed under vacuum, filled with nitrogen, and capped with airtight stoppers to maintain oxygen-limited conditions. 1 mL overnight cultures were inoculated into these bottles and maintained at 30° C. or 37° C. at 250 rpm. For bioreactor studies, 4 mL overnight cultures were grown at 37° C. either in LB or M9 medium supplemented with 2 mM $MgSO_4$, 0.1 mM $CaCl_2$, 20 g/L glucose, 10 g/L tryptone, and the appropriate antibiotic(s). Upon reaching saturation, these cultures were spun down and resuspended in 4 mL of the same medium and cultured for another 4 hours. These cultures were then inoculated into 400 mL bioreactors containing the same M9+tryptone medium with additional 20 g/L each of D-xylose and L-arabinose, as well as antifoam agents. Bioreactors were run at 30° C. with 400 rpm agitation and 0.8 L/min sparging with air. pH was maintained at 7.0±0.1 with 5 N NaOH and 2 N $H_2SO_4$.

Patrick C. Cirino (Pennsylvania State University, PA) provided the crp* parent strain ET23, William W. Metcalf (UIUC) provided the pir+ cloning strain WM1788, and John E. Cronan (UIUC) provided P1 vir phage used for transduction.

(a) sequential fermentation of both arabinose and xylose to xylitol—using two microbial strains. In this process a high arabinose:xylose concentration (>1:1) may be used;

(b) parallel fermentation of both arabinose and xylose to xylitol using a single microbial strain. Two different systems were developed;

(c) conversion of xylose to xylitol with consumption of arabinose using a moderate arabinose:xylitol ratio (>1:3) without a mutation designated CRP. Productivity is about 10× the CRP system. Examples also support that this is an unexpected result. A fermentation system that converts a mixed C5 sugar stream to low-arabitol product uses a CRP (cyclic adenosine monophosphate receptor protein) mutation useful with both the wild-type and mutant XR; and (d) demonstration of a fermentation system using both synthetic hemicellulose and a variety of industrial hemicellulose samples.

| ABBREV | Enzyme Name | Function |
| --- | --- | --- |
| XR (AR) | Xylose (or Aldose) Reductase | Converts xylose (and arabinose) to xylitol (and arabitol) |
| XI | Xylose isomerase | Isomerizes xylose into d-xylulose |
| XDH | Xylitol Dehydrogenase | Converts between d-xylulose and xylitol |
| LXR | l-xylulose reductase | Converts l-xylulose to xylitol |
| LAI | l-arabinose isomerase | Converts l-arabinose to l-ribulose |
| DTE | d-tagatose epimerase | Converts l-ribulose to l-xylulose |

The following biological strains were deposited with the Agricultural Research Service (ARS) Culture Collection (also known as the NRRL Collection), National Center for Agricultural Utilization, Research Agricultural Research Service, USDA, Peoria, Ill., U.S.A., in accordance with the Budapest Treaty:

| Data Strain ID | Deposit No. | Depository | Date of Deposit |
| --- | --- | --- | --- |
| ZUC220 | NRRL B-50526 | ARS (Peoria, IL) | 15 Jul. 2011 |
| ZUC136 | NRRL B-50527 | ARS (Peoria, IL) | 15 Jul. 2011 |
| HZ1434 | NRRL B-50528 | ARS (Peoria, IL) | 19 Jul. 2011 |
| HZ2061 | NRRL B-50529 | ARS (Peoria, IL) | 20 Jul. 2011 |
| HZ2062 | NRRL B-50530 | ARS (Peoria, IL) | 20 Jul. 2011 |

TABLE 1

Strains and plasmids.

| Name | Relevant characteristics | Source/Comments | SEQ |
| --- | --- | --- | --- |
| Plasmids | | | |
| pTrc99A | Amp, pBR322-derived plasmid | Amersham Pharmacia | |
| pACYCDuet | Cm, p15A-derived plasmid | Novagen | |
| pACYC-ncxr | template for XR | Nair and Zhao, 2008 | |
| pACYC-VMQCI | template for XR mutant VMQCI | Nair and Zhao, 2008 | |
| pTKXb-xdharaB' | Km, Source of BLMA promoter | Nair and Zhao, 2008 | |
| pRW2-ptdh | Km, Source of AraBAD promoter | Johannes et al., 2005 | |
| pXXR | pTrc99A with XR under XylA promoter | Present disclosure | (FIG. 20) |
| pXVMQCI | pTrc99A with VMQCI under XylA promoter | Present disclosure | (FIG. 28) |
| pAraXR | pTrc99A with XR under AraBAD promoter | Present disclosure | (FIG. 22) |
| pAraVMQCI | pTrc99A with VMQCI under AraBAD promoter | Present disclosure | |
| pTrcXR | pTrc99A with XR under Trc promoter | Present disclosure | (FIG. 21) |
| pTrcVMQCI | pTrc99A with VMQCI under Trc promoter | Present disclosure | |
| pACYCBLMAXylE | pACYCDuet with xylE under BLMA promoter | Present disclosure | |
| pACYCAraXylE | pACYCDuet with xylE under AraBAD promoter | Present disclosure | (FIG. 29) |
| pCP20 | | created by Paul Taylor | |
| pTRP338 | pTRP200 - pLG338 derivative | | |
| pTRP200 NcXR | Neurospora crassa xylose reductase. NcXR from 7381553. | Present disclosure | |
| pTRP200 CgXR | Chaetomium globosum xylose reductase | Present disclosure | |
| pZUC035 | T. resei (XDH) E. coli (XI) | Taylor patent | |
| pZUC036 | T. resei (XDH) E. coli (XI) | Taylor patent | |
| pZUC052 | T. resei (XDH) E. coli (XI - mutant) | Present disclosure | |
| pATX210 | RtdE (R. radiobacter)/alxR (A. monospora)/ araA (E. coli) | Sakaibara patent | |

TABLE 1-continued

Strains and plasmids.

| Name | Relevant characteristics | Source/Comments | SEQ |
|---|---|---|---|
| pATX215 | RtdE (*R. radiobacter*)/alxR (*A. monospora*)/ araA (*E. coli*). pATX210 derivative with additional arabinose BAD promote | Present disclosure | |
| pATX221 | RtdE (*R. radiobacter*)/alxR (*A. monospora*)/ araA (*E. coli*)/XR (*N. crassa*). combines XR with pATX210 ara pathway | Present disclosure | |
| pATX231 | RtdE (*R. radiobacter*)/alxR (*A. monospora*)/ araA (*E. coli*)/*T. resei* (XDH)/*E. coli* (XI). combines XI/XDH with pATX210 pathway (same orientation of genes) | Present disclosure | |
| pATX231B | RtdE (*R. radiobacter*)/alxR (*A. monospora*)/ araA (*E. coli*)/*T. resei* (XDH)/*E. coli* (XI). combines XI/XDH with pATX210 pathway (opposite orientation of XI XDH genes) | Present disclosure | |

Strains

| Name | Relevant characteristics | Source/Comments | SEQ |
|---|---|---|---|
| MG1655 | gDNA template for XylA promoter and xylE | ATCC 700926 | |
| C600 | F tonA21 thi-1 thr-1 leuB6 lacY1 glnV44 rfbC1 fhuA1 λ⁻ | CGSC, Yale University | |
| ET23 | source of crp*::Tn10 | Eppler and Boos, 1999 | |
| HZ1302 | C600 crp*::Tn10 | Present disclosure | |
| HZ1743 | C600 DptsG::FRT | Present disclosure | |
| HZ1651 | C600 DcyaA$^{regal}$::cat | Present disclosure | |
| HZ1450 | HZ1302 DxylA::FRT | Present disclosure | |
| HZ1967 | HZ1302 DxylAB::FRT | Present disclosure | |
| HZ1756 | HZ1743 DxylA::FRT | Present disclosure | |
| HZ1434 | HZ1450 with pXXR | Present disclosure | |
| HZ1435 | HZ1450 with pXVMQI | Present disclosure | |
| H21757 | HZ1756 with pXXR | Present disclosure | |
| HZ2008 | HZ1450 with pXXR & pACYCAraXylE | Present disclosure | |
| HZ2009 | HZ1450 with pXXR & pACYCBLMAXylE | Present disclosure | |
| HZ2046 | HZ1967 with pTrcXR & pACYCAraXylE | Present disclosure | |
| HZ2061 | HZ1967 with pAraXR & pACYCAraXylE | Present disclosure | |
| HZ2062 | HZ1967 with pAraVMQCI & pACYCAraXylE | Present disclosure | |
| DH5a | | | |
| AB707 | | | |
| ZUC036 | | | |
| ZUC134 | ptsG, xylBD, araBADD, lyxKD, glucose selected (parent IS AB707 K12 prototroph) | Present disclosure | |
| ZUC136 | ptsG, xylBD, araBADD, lyxKD, glucose selected contains pATX210 in ZUC134) | Present disclosure | |
| ZUC138 | | | |
| ZUC142 | | | |
| ZUC140 | ptsG, xylBD, araBADD, lyxKD, glucose selected contains pTRP200-ncXR m ZUC134 | Present disclosure | |
| ZUC166 | ptsG, xylBD, araBADD, lyxKD, glucose selected contains pTRP200-CgXR in ZUC134 | Present disclosure | |
| ZUC170 | F- ompT hsdSB(rB- mB-) gal dcm (DE3) contains pTRP200-NCXR (*E. coli* B - BL21 derivative) | Present disclosure | |
| ZUC172 | | | |
| ZUC220 | xylbD, ptsG-glucose selected (AB707 K12 prototroph derivative) | Present disclosure | |

TABLE 1

Strains and plasmids.

| Name | Relevant characteristics | Source/Comments | SEQ |
|---|---|---|---|
| | Plasmids | | |
| pTrc99A | Amp, pBR322-derived plasmid | Amersham Pharmacia | |
| pACYCDuet | Cm, p15A-derived plasmid | Novagen | |
| pACYC-ncxr | template for XR | Nair and Zhao, 2008 | (FIG. 18) |
| pACYC-VMQCI | template for XR mutant VMQCI | Nair and Zhao, 2008 | |
| pTKXb-xdharaB' | Km, Source of BLMA promoter | Nair and Zhao, 2008 | |
| pRW2-ptdh | Km, Source of AraBAD promoter | Johannes et al., 2005 | |
| pXXR | pTrc99A with XR under XylA promoter | Present disclosure | (FIG. 20) |
| pXVMQCI | pTrc99A with VMQCI under XylA promoter | Present disclosure | (FIG. 28) |

TABLE 1-continued

Strains and plasmids.

| Name | Relevant characteristics | Source/Comments | SEQ |
|---|---|---|---|
| pAraXR | pTrc99A with XR under AraBAD promoter | Present disclosure | (FIG. 22) |
| pAraVMQCI | pTrc99A with VMQCI under AraBAD promoter | Present disclosure | |
| pTrcXR | pTrc99A with XR under Trc promoter | Present disclosure | (FIG. 21) |
| pTrcVMQCI | pTrc99A with VMQCI under Trc promoter | Present disclosure | |
| pACYCBLMAXylE | pACYCDuet with xylE under BLMA promoter | Present disclosure | |
| pACYCAraXylE | pACYCDuet with xylE under AraBAD promoter | Present disclosure | (FIG. 29) |
| pCP20 | | created by Paul Taylor | |
| pTRP338 | pTRP200 - pLG338 derivative | | |
| pTRP200 NcXR | *Neurospora crassa* xylose reductase. NcXR from 7381553. | Present disclosure | |
| pTRP200 CgXR | *Chaetomium globosum* xylose reductase | Present disclosure | |
| pZUC035 | *T. resei* (XDH) *E. coli* (XI) | Taylor patent | |
| pZUC036 | *T. resei* (XDH) *E. coli* (XI) | Taylor patent | |
| pZUC052 | *T. resei* (XDH) *E. coli* (XI - mutant) | Present disclosure | |
| pATX210 | RtdE (*R. radiobacter*)/alxR (*A. monospora*)/araA (*E. coli*) | Sakaibara patent | |
| pATX215 | RtdE (*R. radiobacter*)/alxR (*A. monospora*)/araA (*E. coli*). pATX210 derivative with additional arabinose BAD promote | Present disclosure | |
| pATX221 | RtdE (*R. radiobacter*)/alxR (*A. monospora*)/araA (*E. coli*)/XR (*N. crassa*). combines XR with pATX210 ara pathway | Present disclosure | |
| pATX231 | RtdE (*R. radiobacter*)/alxR (*A. monospora*)/araA (*E. coli*)/*T. resei* (XDH)/*E. coli* (XI). combines XI/XDH with pATX210 pathway (same orientation of genes) | Present disclosure | |
| pATX231B | RtdE (*R. radiobacter*)/alxR (*A. monospora*)/araA (*E. coli*)/*T. resei* (XDH)/*E. coli* (XI). combines XI/XDH with pATX210 pathway (opposite orientation of XI XDH genes) | Present disclosure | |

Strains

| Name | Relevant characteristics | Source/Comments | SEQ |
|---|---|---|---|
| MG1655 | gDNA template for XylA promoter and xylE | ATCC 700926 | |
| C600 | F tonA21 thi-1 thr-1 leuB6 lacY1 glnV44 rfbC1 fhuA1 λ- | CGSC, Yale University | |
| ET23 | source of crp*: :Tn10 | Eppler and Boos, 1999 | |
| HZ1302 | C600 crp*: :Tn10 | Present disclosure | |
| HZ1743 | C600 DptsG: :FRT | Present disclosure | |
| HZ1651 | C600 DcyaA$^{regal}$: :cat | Present disclosure | |
| HZ1450 | HZ1302 DxylA: :FRT | Present disclosure | |
| HZ1967 | HZ1302 DxylAB: :FRT | Present disclosure | |
| HZ1756 | HZ1743 DxylA: :FRT | Present disclosure | |
| HZ1434 | HZ1450 with pXXR | Present disclosure | |
| HZ1435 | HZ1450 with pXVMQI | Present disclosure | |
| H21757 | HZ1756 with pXXR | Present disclosure | |
| HZ2008 | HZ1450 with pXXR & pACYCAraXylE | Present disclosure | |
| HZ2009 | HZ1450 with pXXR & pACYCBLMAXylE | Present disclosure | |
| HZ2046 | HZ1967 with pTrcXR & pACYCAraXylE | Present disclosure | |
| HZ2061 | HZ1967 with pAraXR & pACYCAraXylE | Present disclosure | |
| HZ2062 | HZ1967 with pAraVMQCI & pACYCAraXylE | Present disclosure | |
| DH5a | | | |
| AB707 | | | |
| ZUC036 | | | |
| ZUC134 | ptsG, xylBD, araBADD, lnxKD, glucose selected (parent IS AB707 K12 prototroph) | Present disclosure | |
| ZUC136 | ptsG, xylBD, araBADD, lyxKD, glucose selected contains pATX210 in ZUC134) | Present disclosure | |
| ZUC138 | | | |
| ZUC142 | | | |
| ZUC140 | ptsG, xylBD, araBADD, lyxKD, glucose selected contains pTRP200-ncXR m ZUC134 | Present disclosure | |
| ZUC166 | ptsG, xylBD, araBADD, lyxKD, glucose selected contains pTRP200-CgXR in ZUC134 | Present disclosure | |
| ZUC170 | F- ompT hsdSB(rB- mB-) gal dcm (DE3) contains pTRP200-NCXR (*E. coli* B - BL21 derivative) | Present disclosure | |
| ZUC172 | | | |
| ZUC220 | xylbD, ptsG-glucose selected (AB707 K12 prototroph derivative) | Present disclosure | |

PUBLICATIONS

The following documents are incorporated by reference to the extent they relate to or describe materials or methods disclosed herein. Specific locations in publications cited appear in the specification.

Akinterinwa, O., Cirino, P. C., 2009. Heterologous expression of D-xylulokinase from *Pichia stipitis* enables high levels of xylitol production by engineered *Escherichia coli* growing on xylose. Metab. Eng. 11, 48-55.

Cirino, P. C., et al., 2006. Engineering *Escherichia coli* for xylitol production from glucose-xylose mixtures. Biotech. Bioeng. 95, 1167-1176.

Datsenko, K. A., Wanner, B. L., 2000. One-step inactivation of chromosomal genes in *Escherichia coli* K-12 using PCR products. Proc. Natl. Acad. Sci. USA. 97, 6640-6645.

Eiteman, M. A., Altman, E., 2006. Overcoming acetate in *Escherichia coli* recombinant protein fermentations. Trends Biotechnol. 24, 530-536.

Eppler, T., Boos, W., 1999. Glycerol-3-phosphate-mediated repression of malT in *Escherichia coli* does not require metabolism, depends on enzyme IIA(Glc) and is mediated by cAMP levels. Mol. Microbiol. 33, 1221-1231.

Johannes, T. W., et al., 2005. Directed evolution of a thermostable phosphite dehydrogenase for NAD(P)H regeneration. Appl. Environ. Microb. 71, 5728-5734.

Karimova, G., et al., 2004. Relief of catabolite repression in a cAMP-independent catabolite gene activator mutant of *Escherichia coli*. Res. Microbiol. 155, 76-79.

Kim, Y. W., et al., 2003. Directed evolution of *Thermus maltogenic* amylase toward enhanced thermal resistance. Appl. Environ. Microb. 69, 4866-4874.

Lindsay, S. E., et al., 1995. Improved strains of recombinant *Escherichia coli* for ethanol production from sugar mixtures. Appl. Environ. Microb. 43, 70-5.

Miller, J. H., 1992. A short course in bacterial genetics: a laboratory manual and handbook for *Escherichia coli* and related bacteria. Cold Spring Harbor Laboratory Press, Plainview, N.Y.

Nair, N. U., Zhao, H., 2008. Evolution in reverse: engineering a D-xylose-specific xylose reductase. Chembiochem. 9, 1213-5.

Nichols, N. N., et al., 2001. Use of catabolite repression mutants for fermentation of sugar mixtures to ethanol. Appl. Microbiol. Biotechnol. 56, 120-5.

Zha, W. J., et al., 2008. Exploiting genetic diversity by directed evolution: molecular breeding of type III polyketide synthases improves productivity. Mol. Biosyst. 4, 246-248.

---

We claim:

1. A method to produce xylitol from a mixture of hemicellulosic sugars having a xylose:arabinose ratio of about 3:1 or better, the method comprising treating the mixture of hemicellulosic sugars with enzymes produced by genetically engineered microorganisms, wherein the genetically engineered microorganisms comprise microorganisms having a recombinant xylose reductase (XR) that is more active on xylose than arabinose, wherein the genetically engineered microorganisms comprise an inactivated ptsG gene and an inactivated xylB gene, wherein arabinose and xylose are consumed, and wherein the enzymes produce xylitol at an increased purity with little or no arabinitol present in a final mixture.

2. The method to produce xylitol of claim 1, wherein the recombinant xylose reductase is from Chaetomium globosum or Neurospora crassa.

3. The method to produce xylitol of claim 1, comprising reducing D-xylose and metabolizing arabinose.

4. The method of claim 1, wherein the recombinant xylose reductase has the amino acid sequence set forth in SEQ ID NO: 1, SEQ ID NO: 10, SEQ ID NO:12, SEQ ID NO:14, SEQ ID NO:16, SEQ ID NO:18, or SEQ ID NO:20.

5. The method of claim 1, wherein the mixture of hemicellulosic sugars is corn fiber hydrolysate, corn stover hydrolysate, bagasse hydrolysate, stillage hydrolysate, wheat straw hydrolysate, hardwood hydrolysate, softwood hydrolysate or other biomass sources.

6. The method of claim 1, wherein arabinitol is less than 10% of the final mixture.

7. The method of claim 1, wherein arabinitol is less than 5% of the final mixture.

8. The method of claim 1, wherein the genetically engineered microorganisms are selected from the group consisting of ZUC220, ZUC136, and combinations thereof.

9. The method of claim 1, wherein xylitol is recovered from the final mixture.

10. The method of claim 1, wherein the mixture of hemicellulosic sugars is also treated with calcium hydroxide.

11. A method to produce xylitol from a mixture of hemicellulosic sugars having a xylose:arabinose ratio of about 3:1 or better, the method comprising treating the mixture of hemicellulosic sugars with enzymes produced by one or more genetically engineered microorganisms selected from the group consisting of ZUC220, ZUC136, and combinations thereof, wherein the genetically engineered microorganisms comprise microorganisms having a recombinant xylose reductase (XR) that is more active on xylose than arabinose, wherein arabinose and xylose are consumed, wherein the enzymes produce xylitol at an increased purity with little or no arabinitol present in a final mixture.

12. The method of claim 1, wherein the mixture of hemicellulosic sugars comprise non-synthetic hemicellulose.

13. The method of claim 12, wherein the non-synthetic hemicellulose is derived from corn fiber, woody fiber, hardwood hydrolysate, corn stover, corn cob, bagasse, stillage, wheat straw, hardwood, or softwood.

14. The method of claim 1, wherein the xylitol is produced by fermentation and wherein little or no arabinitol is present in a final fermentation broth.

15. The method of claim 1, wherein the recombinant xylose reductase has the amino acid sequence set forth in SEQ ID NO:4.

16. The method of claim 1, wherein the genetically engineered microorganisms further comprise an inactivated lyxK gene.

17. The method of claim 1, wherein the genetically engineered microorganisms are selected on M9+glucose liquid medium several times for improved growth.

18. The method to produce xylitol of claim 1, wherein the recombinant xylose reductase is from *Chaetomium globosum*.

\* \* \* \* \*

SEQUENCE LISTING

```
<160> NUMBER OF SEQ ID NOS: 21

<210> SEQ ID NO 1
<211> LENGTH: 322
<212> TYPE: PRT
<213> ORGANISM: Chaetomium globosum

<400> SEQUENCE: 1

Met Ala Pro Val Ile Lys Leu Asn Ser Gly Tyr Asp Met Pro Gln Val
1               5                   10                  15

Gly Phe Gly Leu Trp Lys Val Asp Asn Ala Val Ala Ser Asp Val Val
                20                  25                  30

Tyr Asn Ala Ile Lys Ala Gly Tyr Arg Leu Phe Asp Gly Ala Cys Asp
            35                  40                  45

Tyr Gly Asn Glu Val Glu Cys Gly Gln Gly Val Ala Arg Ala Ile Ser
        50                  55                  60

Glu Gly Ile Val Lys Arg Glu Asp Leu Phe Ile Val Ser Lys Leu Trp
65                  70                  75                  80

Asn Thr Phe His Asp Ala Glu Arg Val Glu Pro Ile Val Lys Lys Gln
                85                  90                  95

Leu Ala Asp Trp Gly Ile Glu Tyr Phe Asp Leu Tyr Leu Ile His Phe
                100                 105                 110

Pro Val Ala Leu Glu Trp Val Asp Pro Ala Val Arg Tyr Pro Pro Gly
            115                 120                 125

Trp His Tyr Asp Gly Lys Glu Ile Arg Pro Ser Lys Ala Thr Ile
        130                 135                 140

Gln Glu Thr Trp Thr Ala Leu Glu Ser Leu Val Ser Lys Gly Leu Ser
145                 150                 155                 160

Lys Ser Ile Gly Ile Ser Asn Phe Gln Ala Gln Leu Ile Tyr Asp Leu
                165                 170                 175

Leu Arg Tyr Ala Lys Ile Arg Pro Ala Thr Leu Gln Val Glu His His
                180                 185                 190

Pro Tyr Leu Val Gln Gln Glu Leu Ile Asn Leu Ala Lys Arg Glu Gly
```

```
                195                 200                 205
Ile Ala Val Thr Ala Tyr Ser Ser Phe Gly Pro Ala Ser Phe Lys Glu
    210                 215                 220

Phe Asn Met Lys His Ala Asp Ala Leu Ala Pro Leu Ile Glu Asp Glu
225                 230                 235                 240

Thr Ile Lys Lys Ile Ala Ala Lys His Asn Arg Pro Ala Ser Gln Val
                245                 250                 255

Leu Leu Arg Trp Ala Thr Gln Arg Gly Leu Ala Ile Ile Pro Lys Ser
            260                 265                 270

Thr Arg Pro Gln Ile Met Ala Glu Asn Phe Gln Ser Ile Asp Phe Asp
        275                 280                 285

Leu Ser Glu Glu Asp Ile Ala Thr Ile Ser Ala Phe Asp Arg Gly Ile
    290                 295                 300

Arg Phe Asn Gln Pro Ser Asn Tyr Phe Pro Thr Glu Leu Leu Trp Ile
305                 310                 315                 320

Phe Gly

<210> SEQ ID NO 2
<211> LENGTH: 969
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 2
atggcgccgg tgattaaact gaacagcggc tatgatatgc cgcaggtggg ctttggcctg        60
tggaaagtgg ataacgcggt ggcgagcgat gtggtgtata cgcgattaa agcgggctat       120 cgtctgtttg atggcgcgtg cgattatggc aacgaagtgg aatgcggcca gggtgtggcg       180
cgtgccatca gcgaaggcat tgtgaaacgt gaggacctgt tcattgtgag caaactgtgg       240
aacacctttc atgatgcgga acgtgtggaa ccgattgtga aaaacagct ggccgattgg        300 ggcattgaat atttcgatct gtatctgatc cattttccgg tggcgctgga atgggttgat       360
ccggcggtgc gttatccgcc gggttggcat tatgatggca agaagaaat cgtccgagc        420 aaagcgacca ttcaggaaac ctggaccgcg ctggaaagcc tggtgagcaa aggcctgagc       480
aaaagcattg cattagcaa ctttcaggcg cagctgattt atgatctgct cgctatgcg         540 aaaattcgtc cggcgaccct gcaggtggaa catcatccgt atctggtgca gcaggaactg       600
attaacctgg ccaaacgtga aggcattgcg gtgaccgcgt atagcagctt ggtccggcc        660 agctttaaag aatttaacat gaaacatgcg gatgcgctgg ccccgctgat tgaagatgaa       720
accatcaaaa aaatcgcggc gaaacataac cgtccggcga gccaggttct gctgcgttgg       780
gcgacccagc gtggcctggc cattattccg aaaagcaccc gtccgcagat tatggcggaa       840
aactttcaga gcatcgattt tgatctgagc gaagaagata ttgcgaccat tagcgcgttt       900
gatcgtggca ttcgttttaa ccagccgagc aactattttc cgaccgaact gctgtggatt       960
tttggctaa                                                              969

<210> SEQ ID NO 3
<211> LENGTH: 969
<212> TYPE: DNA
<213> ORGANISM: Neurospora crassa

<400> SEQUENCE: 3
```

```
atggttcctg ctatcaagct caactccggc ttcgacatgc cccaggtcgg cttcggcctc    60
tggaaggtcg acggctccat cgcttccgat gtcgtctaca cgctatcaa ggcaggctac   120
cgcctcttcg atggtgcctg cgactacggc aacgaggttg agtgcggcca gggtgtagcc   180
cgcgccatca aggagggcat cgtcaagcgc gaggagctct ttatcgtctc caagctctgg   240
aacaccttcc acgacggcga ccgcgtcgag cccatcgtcc gcaagcagct tgccgactgg   300
ggtctcgagt acttcgatct ctacctgatc cacttccccg tcgccctcga gtacgtcgac   360
ccctcggtcc gttaccctcc cggctggcac tttgacggca gagcgagat ccgcccctcc   420
aaggccacca tccaagagac ctggacggca atggagtcgc tcgtcgagaa gggtctctcc   480
aagagcattg gcgtctccaa cttccaggcc agctcctgt acgacctcct ccgctacgcc   540
aaggtccgcc ccgccactct ccagatcgag caccacccct acctcgtcca gcagaacctc   600
ctcaaccttg ccaaggctga gggcatcgcc gtgaccgcct actcctcctt cggccctgct   660
tctttccgcg agttcaacat ggagcacgcc cagaagctcc agcctctcct cgaggacccc   720
accatcaagg ctattggtga caagtacaac aaggatcctg cccaggtcct cctccgttgg   780
gccacccagc gcggcctggc catcatcccc aagtctagcc gcgaggccac catgaagtcc   840
aacctcaact ctcttgattt cgatctctcc gaggaggaca tcaagaccat ctctggtttc   900
gaccgcggca tccgcttcaa ccagcccacc aactacttct ccgctgagaa cctctggatt   960
ttcggttag                                                           969
```

<210> SEQ ID NO 4
<211> LENGTH: 322
<212> TYPE: PRT
<213> ORGANISM: Neurospora crassa

<400> SEQUENCE: 4

```
Met Val Pro Ala Ile Lys Leu Asn Ser Gly Phe Asp Met Pro Gln Val
1               5                   10                  15

Gly Phe Gly Leu Trp Lys Val Asp Gly Ser Ile Ala Ser Asp Val Val
            20                  25                  30

Tyr Asn Ala Ile Lys Ala Gly Tyr Arg Leu Phe Asp Gly Ala Cys Asp
        35                  40                  45

Tyr Gly Asn Glu Val Glu Cys Gly Gln Gly Val Ala Arg Ala Ile Lys
    50                  55                  60

Glu Gly Ile Val Lys Arg Glu Glu Leu Phe Ile Val Ser Lys Leu Trp
65                  70                  75                  80

Asn Thr Phe His Asp Gly Asp Arg Val Glu Pro Ile Val Arg Lys Gln
                85                  90                  95

Leu Ala Asp Trp Gly Leu Glu Tyr Phe Asp Leu Tyr Leu Ile His Phe
            100                 105                 110

Pro Val Ala Leu Glu Tyr Val Asp Pro Ser Val Arg Tyr Pro Pro Gly
        115                 120                 125

Trp His Phe Asp Gly Lys Ser Glu Ile Arg Pro Ser Lys Ala Thr Ile
    130                 135                 140

Gln Glu Thr Trp Thr Ala Met Glu Ser Leu Val Glu Lys Gly Leu Ser
145                 150                 155                 160

Lys Ser Ile Gly Val Ser Asn Phe Gln Ala Gln Leu Leu Tyr Asp Leu
                165                 170                 175

Leu Arg Tyr Ala Lys Val Arg Pro Ala Thr Leu Gln Ile Glu His His
            180                 185                 190

Pro Tyr Leu Val Gln Gln Asn Leu Leu Asn Leu Ala Lys Ala Glu Gly
```

```
                    195                 200                 205
Ile Ala Val Thr Ala Tyr Ser Ser Phe Gly Pro Ala Ser Phe Arg Glu
                210                 215                 220
Phe Asn Met Glu His Ala Gln Lys Leu Gln Pro Leu Leu Glu Asp Pro
225                 230                 235                 240
Thr Ile Lys Ala Ile Gly Asp Lys Tyr Asn Lys Asp Pro Ala Gln Val
                245                 250                 255
Leu Leu Arg Trp Ala Thr Gln Arg Gly Leu Ala Ile Ile Pro Lys Ser
                260                 265                 270
Ser Arg Glu Ala Thr Met Lys Ser Asn Leu Asn Ser Leu Asp Phe Asp
                275                 280                 285
Leu Ser Glu Glu Asp Ile Lys Thr Ile Ser Gly Phe Asp Arg Gly Ile
                290                 295                 300
Arg Phe Asn Gln Pro Thr Asn Tyr Phe Ser Ala Glu Asn Leu Trp Ile
305                 310                 315                 320
Phe Gly
```

<210> SEQ ID NO 5
<211> LENGTH: 4791
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 5

```
ggggaattgt gagcggataa caattcccct gtagaaataa ttttgtttaa ctttaataag     60
gagatatacc atgggcagca gccatcacca tcatcaccac agccaggatc cgaattcgat    120
ggttcctgct atcaagctca actccggctt cgacatgccc aggtcggct tcggcctctg     180
gaaggtcgac ggctccatcg cttccgatgt cgtctacaac gctatcaagg caggctaccg    240
cctcttcgat ggtgcctgcg actacggcaa cgaggttgag tgcggccagg gtgtagcccg    300
cgccatcaag gagggcatcg tcaagcgcga ggagctcttt atcgtctcca agctctggaa    360
caccttccac gacggcgacc gcgtcgagcc catcgtccgc aagcagcttg ccgactgggg    420
tctcgagtac ttcgatctct acctgatcca cttccccgtc gccctcgagt acgtcgaccc    480
ctcggtccgt taccctcccg gctggcactt tgacggcaag agcgagatcc gccctccaa     540
ggccaccatc aagagacct ggacggccat ggagtcgctc gtcgagaagg gtctctccaa     600
gagcattggc gtctccaact tccaggccca gctcctgtac gacctcctcc gctacgccaa    660
ggtccgcccc gccactctcc agatcgagca ccaccctac ctcgtccagc agaacctcct     720
caaccttgcc aaggctgagg catcgccgt gaccgcctac tcctccttcg gccctgcttc     780
tttccgcgag ttcaacatgg agcacgccca agctccag cctctcctcg aggaccccac     840
catcaaggct attggtgaca gtacaacaa ggatcctgcc caggtcctcc tccgttgggc     900
cacccagcgc ggcctggcca tcatccccaa gtctagccgc gaggccacca tgaagtccaa    960
cctcaactct cttgatttcg atctctccga ggaggacatc aagaccatct ctggtttcga   1020
ccgcggcatc cgcttcaacc agcccaccaa ctacttctcc gctgagaacc tctggatttt   1080
cggttagaga tctcaattgg atatcggccg gccacgcgat cgctgacgtc ggtaccctcg   1140
agtctggtaa agaaaccgct gctgcgaaat tgaacgcca gcacatggac tcgtctacta   1200
gcgcagctta attaacctag gctgctgcca ccgctgagca ataactagca taacccttg    1260
```

```
gggcctctaa acgggtcttg aggggttttt tgctgaaacc tcaggcattt gagaagcaca   1320
cggtcacact gcttccggta gtcaataaac cggtaaacca gcaatagaca taagcggcta   1380
tttaacgacc ctgccctgaa ccgacgaccg ggtcgaattt gctttcgaat ttctgccatt   1440
catccgctta ttatcactta ttcaggcgta gcaccaggcg tttaagggca ccaataactg   1500
ccttaaaaaa attacgcccc gccctgccac tcatcgcagt actgttgtaa ttcattaagc   1560
attctgccga catggaagcc atcacagacg gcatgatgaa cctgaatcgc cagcggcatc   1620
agcaccttgt cgccttgcgt ataatatttg cccatagtga aaacgggggc gaagaagttg   1680
tccatattgg ccacgtttaa atcaaaactg gtgaaactca cccagggatt ggctgagacg   1740
aaaaacatat tctcaataaa ccctttaggg aataggcca ggttttcacc gtaacacgcc   1800
acatcttgcg aatatatgtg tagaaactgc cggaaatcgt cgtggtattc actccagagc   1860
gatgaaaacg tttcagtttg ctcatggaaa acggtgtaac aagggtgaac actatcccat   1920
atcaccagct caccgtcttt cattgccata cggaactccg gatgagcatt catcaggcgg   1980
gcaagaatgt gaataaaggc cggataaaac ttgtgcttat ttttctttac ggtctttaaa   2040
aaggccgtaa tatccagctg aacggtctgg ttataggtac attgagcaac tgactgaaat   2100
gcctcaaaat gttctttacg atgccattgg gatatatcaa cggtggtata tccagtgatt   2160 ttttctcca ttttagcttc cttagctcct gaaaatctcg ataactcaaa aaatacgccc   2220
ggtagtgatc ttatttcatt atggtgaaag ttggaacctc ttacgtgccg atcaacgtct   2280
cattttcgcc aaaagttggc ccagggcttc ccggtatcaa cagggacacc aggatttatt   2340
tattctgcga agtgatcttc cgtcacaggt atttattcgg cgcaaagtgc gtcgggtgat   2400
gctgccaact tactgattta gtgtatgatg gtgttttga ggtgctccag tggcttctgt   2460
ttctatcagc tgtccctcct gttcagctac tgacggggtg gtgcgtaacg gcaaaagcac   2520
cgccggacat cagcgctagc ggagtgtata ctggcttact atgttggcac tgatgagggt   2580
gtcagtgaag tgcttcatgt ggcaggagaa aaaaggctgc accggtgcgt cagcagaata   2640
tgtgatacag gatatattcc gcttcctcgc tcactgactc gctacgctcg gtcgttcgac   2700
tgcggcgagc ggaaatggct tacgaacggg gcggagattt cctggaagat gccaggaaga   2760
tacttaacag ggaagtgaga gggccgcggc aaagccgttt ttccataggc tccgcccccc   2820
tgacaagcat cacgaaatct gacgctcaaa tcagtggtgg cgaaacccga caggactata   2880
aagataccag gcgtttcccc tggcggctcc ctcgtgcgct ctcctgttcc tgcctttcgg   2940
tttaccggtg tcattccgct gttatggccg cgtttgtctc attccacgcc tgacactcag   3000
ttccgggtag gcagttcgct ccaagctgga ctgtatgcac gaaccccccg ttcagtccga   3060
ccgctgcgcc ttatccggta actatcgtct tgagtccaac ccggaaagac atgcaaaagc   3120
accactggca gcagccactg gtaattgatt tagaggagtt agtcttgaag tcatgcgccg   3180
gttaaggcta aactgaaagg acaagttttg gtgactgcgc tcctccaagc cagttacctc   3240
ggttcaaaga gttggtagct cagagaacct tcgaaaaacc gccctgcaag gcggtttttt   3300
cgttttcaga gcaagagatt acgcgcagac caaaacgatc tcaagaagat catcttatta   3360
atcgataaaa atatttctag atttcagtgc aatttatctc ttcaaatgta gcacctgaag   3420
tcagccccat acgatataag ttgtaattct catgttagtc atgccccgcg cccaccggaa   3480
ggagctgact gggttgaagg ctctcaaggg catcggtcga gatccccgtg cctaatgagt   3540
gagctaactt acattaattg cgttgcgctc actgcccgct ttccagtcgg gaaacctgtc   3600
gtgccagctg cattaatgaa tcggccaacg cgcggggaga ggcggtttgc gtattgggcg   3660
```

```
ccagggtggt ttttcttttc accagtgaga cgggcaacag ctgattgccc ttcaccgcct    3720
ggccctgaga gagttgcagc aagcggtcca cgctggtttg ccccagcagg cgaaaatcct    3780
gtttgatggt ggttaacggc gggatataac atgagctgtc ttcggtatcg tcgtatccca    3840
ctaccgagat gtccgcacca acgcgcagcc cggactcggt aatggcgcgc attgcgccca    3900
gcgccatctg atcgttggca accagcatcg cagtgggaac gatgccctca ttcagcattt    3960
gcatggtttt ttgaaaaccg gacatggcac tccagtcgcc ttcccgttcc gctatcggct    4020
gaatttgatt gcgagtgaga tatttatgcc agccagccag acgcagacgc gccgagacag    4080
aacttaatgg gcccgctaac agcgcgattt gctggtgacc caatgcgacc agatgctcca    4140
cgcccagtcg cgtaccgtct tcatgggaga aaataatact gttgatgggt gtctggtcag    4200
agacatcaag aaataacgcc ggaacattag tgcaggcagc ttccacagca atggcatcct    4260
ggtcatccag cggatagtta atgatcagcc cactgacgcg ttgcgcgaga agattgtgca    4320
ccgccgcttt acaggcttcg acgccgcttc gttctaccat cgacaccacc acgctggcac    4380
ccagttgatc ggcgcgagat ttaatcgccg cgacaatttg cgacggcgcg tgcagggcca    4440
gactggaggt ggcaacgcca atcagcaacg actgtttgcc cgccagttgt tgtgccacgc    4500
ggttgggaat gtaattcagc tccgccatcg ccgcttccac ttttttcccgc gttttcgcag    4560 aaacgtggct ggcctggttc accacgcggg aaacggtctg ataagagaca ccggcatact    4620
ctgcgacatc gtataacgtt actggtttca cattcaccac cctgaattga ctctcttccg    4680
ggcgctatca tgcctataccg cgaaaggttt tgcgccattc gatggtgtcc gggatctcga    4740
cgctctccct tatgcgactc ctgcattagg aaattaatac gactcactat a              4791

<210> SEQ ID NO 6
<211> LENGTH: 3780
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6
atgcatttcc attttatttt gcgagcgagc gcacacttgt gaattatctc aatagcagtg     60
tgaaataaca taattgagca actgaaaggg agtgcccaat attacgacat catccatcac    120
ccgcggcatt acctgattat ggttcctgct atcaagctca actccggctt cgacatgccc    180
caggtcggct tcggcctctg gaaggtcgac ggctccatcg cttccgatgt cgtctacaac    240
gctatcaagg caggctaccg cctcttcgat ggtgcctgcg actacggcaa cgaggttgag    300
tgcggccagg tgtagcccg cgccatcaag gagggcatcg tcaagcgcga ggagctcttt    360
atcgtctcca agctctggaa caccttccac gacggcgacc gcgtcgagcc catcgtccgc    420
aagcagcttg ccgactgggg tctcgagtac ttcgatctct acctgatcca cttccccgtc    480
gccctcgagt acgtcgaccc ctcggtccgt taccctcccg gctggcactt tgacggcaag    540
agcgagatcc gccccctcca aggccaccat caagagacct ggacggccat ggagtcgctc    600
gtcgagaagg tctctccaa gagcattggc gtctccaact tccaggccca gctcctgtac    660
gacctcctcc gctacgccaa ggtccgcccc gccactctcc agatcgagca ccacccctac    720
ctcgtccagc agaacctcct caaccttgcc aaggctgagg catcgccgt gaccgcctac    780 tcctccttcg gccctgcttc tttccgcgag ttcaacatgg agcacgccca gaagctccag    840
```

```
cctctcctcg aggacccac catcaaggct attggtgaca agtacaacaa ggatcctgcc    900
caggtcctcc tccgttgggc cacccagcgc ggcctggcca tcatcccaa gtctagccgc    960
gaggccacca tgaagtccaa cctcaactct cttgatttcg atctctccga ggaggacatc   1020
aagaccatct ctggtttcga ccgcggcatc cgcttcaacc agcccaccaa ctacttctcc   1080
gctgagaacc tctggatttt cggttagaga tcctctagag tcgacctgca ggcatgcaag   1140
cttggctgtt ttggcggatg agagaagatt ttcagcctga tacagattaa atcagaacgc   1200
agaagcggtc tgataaaaca gaatttgcct ggcggcagta gcgcggtggt cccacctgac   1260
cccatgccga actcagaagt gaaacgccgt agcgccgatg gtagtgtggg gtctccccat   1320
gcgagagtag ggaactgcca ggcatcaaat aaaacgaaag gctcagtcga agactgggc    1380
ctttcgtttt atctgttgtt tgtcggtgaa cgctctcctg agtaggacaa atccgccggg   1440
agcggatttg aacgttgcga agcaacggcc cggagggtgg cgggcaggac gcccgccata   1500
aactgccagg catcaaatta gcagaaggc catcctgacg gatggccttt ttgcgtttct    1560
acaaactctt tttgtttatt tttctaaata cattcaaata tgtatccgct catgagacaa   1620
taaccctgat aaatgcttca ataatattga aaaggaaga gtatgagtat tcaacatttc    1680
cgtgtcgccc ttattccctt ttttgcgca ttttgccttc ctgttttgc tcacccagaa     1740
acgctggtga agtaaaaga tgctgaagat cagttgggtg cacgagtggg ttacatcgaa    1800
ctggatctca acagcggtaa gatccttgag agttttcgcc ccgaagaacg ttttccaatg   1860
atgagcactt ttaaagttct gctatgtggc gcggtattat cccgtgttga cgccgggcaa   1920
gagcaactcg gtcgccgcat acactattct cagaatgact tggttgagta ctcaccagtc   1980
acagaaaagc atcttacgga tggcatgaca gtaagagaat tatgcagtgc tgccataacc   2040
atgagtgata acactgcggc caacttactt ctgacaacga tcggaggacc gaaggagcta   2100
accgcttttt tgcacaacat gggggatcat gtaactcgcc ttgatcgttg ggaaccggag   2160
ctgaatgaag ccataccaaa cgacgagcgt gacaccacga tgcctacagc aatggcaaca   2220
acgttgcgca aactattaac tggcgaacta cttactctag cttcccggca acaattaata   2280
gactggatgg aggcggataa agttgcagga ccacttctgc gctcggccct tccggctggc   2340
tggtttattg ctgataaatc tggagccggt gagcgtgggt ctcgcggtat cattgcagca   2400
ctggggccag atggtaagcc ctcccgtatc gtagttatct acacgacggg gagtcaggca   2460
actatggatg aacgaaatag acagatcgct gagataggtg cctcactgat taagcattgg   2520
taactgtcag accaagttta ctcatatata ctttagattg atttaaaact tcattttttaa  2580
tttaaaagga tctaggtgaa gatcctttt gataatctca tgaccaaaat cccttaacgt    2640
gagttttcgt tccactgagc gtcagacccc gtagaaaaga tcaaaggatc ttcttgagat   2700
ccttttttc tgcgcgtaat ctgctgcttg caaacaaaaa aaccaccgct accagcggtg    2760
gtttgtttgc cggatcaaga gctaccaact cttttccga aggtaactgg cttcagcaga    2820
gcgcagatac caaatactgt ccttctagtg tagccgtagt taggccacca cttcaagaac   2880
tctgtagcac cgcctacata cctcgctctg ctaatcctgt taccagtggc tgctgccagt   2940
ggcgataagt cgtgtcttac cgggttggac tcaagacgat agttaccgga taaggcgcag   3000
cggtcgggct gaacgggggg ttcgtgcaca cagcccagct tggagcgaac gacctacacc   3060
gaactgagat acctacagcg tgagctatga gaaagcgcca cgcttcccga agggagaaag   3120
gcggacaggt atccggtaag cggcaggtc ggaacaggag agcgcacgag ggagcttcca    3180
gggggaaacg cctggtatct ttatagtcct gtcgggtttc gccacctctg acttgagcgt   3240
```

```
cgatttttgt gatgctcgtc aggggggcgg agcctatgga aaaacgccag caacgcggcc    3300 ttttttacggt tcctggcctt ttgctggcct tttgctcaca tgttctttcc tgcgttatcc    3360
cctgattctg tggataaccg tattaccgcc tttgagtgag ctgataccgc tcgccgcagc    3420
cgaacgaccg agcgcagcga gtcagtgagc gaggaagcgg aagagcgcct gatgcggtat    3480
tttctcctta cgcatctgtg cggtatttca caccgcatat ggtgcactct cagtacaatc    3540
tgctctgatg ccgcatagtt aagccagtat acactccgct atcgctacgt gactgggtca    3600
tggctgcgcc ccgacacccg ccaacacccg ctgacgcgcc ctgacgggct tgtctgctcc    3660
cggcatccgc ttacagacaa gctgtgaccg tctccgggag ctgcatgtgt cagaggtttt    3720
caccgtcatc accgaaacgc gcgaggcagc agatcaattc gcgcgcgaag gcgaagcggc    3780
```

<210> SEQ ID NO 7
<211> LENGTH: 5142
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 7

```
gtttgacagc ttatcatcga ctgcacggtg caccaatgct tctggcgtca ggcagccatc      60
ggaagctgtg gtatggctgt gcaggtcgta atcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagaccatgg aattcgagct cggtaccatg gttcctgcta     300
tcaagctcaa ctccggcttc gacatgcccc aggtcggctt cggcctctgg aaggtcgacg     360
gctccatcgc ttccgatgtc gtctacaacg ctatcaaggc aggctaccgc ctcttcgatg     420
gtgcctgcga ctacggcaac gaggttgagt gcggccaggg tgtagcccgc gccatcaagg     480
agggcatcgt caagcgcgag gagctcttta tcgtctccaa gctctggaac accttccacg     540
acggcgaccg cgtcgagccc atcgtccgca agcagcttgc cgactgggt ctcgagtact     600 tcgatctcta cctgatccac ttccccgtcg ccctcgagta cgtcgacccc tcggtccgtt     660
accctcccgg ctggcacttt gacggcaaga gcgagatccg ccctccaag gccaccatcc     720 aagagacctg gacggccatg gagtcgctcg tcgagaaggg tctctccaag agcattggcg     780
tctccaactt ccaggcccag ctcctgtacg acctcctccg ctacgccaag gtccgccccg     840
ccactctcca gatcgagcac caccctacc tcgtccagca gaacctcctc aaccttgcca     900
aggctgaggg catcgccgtg accgcctact cctccttcgg ccctgcttct ttccgcgagt     960
tcaacatgga gcacgcccag aagctccagc ctctcctcga ggaccccacc atcaaggcta    1020
ttggtgacaa gtacaacaag gatcctgccc aggtcctcct ccgttgggcc acccagcgcg    1080
gcctggccat catccccaag tctagccgcg aggccaccat gaagtccaac ctcaactctc    1140
ttgatttcga tctctccgag gaggacatca gaccatctc tggtttcgac cgcggcatcc    1200
gcttcaacca gcccaccaac tacttctccg ctgagaacct ctggatttc ggttagagat    1260 cctctagagt cgacctgcag gcatgcaagc ttggctgttt tggcggatga gaagagattt    1320
tcagcctgat acagattaaa tcagaacgca gaagcggtct gataaaacag aatttgcctg    1380
gcggcagtag cgcggtggtc ccacctgacc ccatgccgaa ctcagaagtg aaacgccgta    1440
```

```
gcgccgatgg tagtgtgggg tctccccatg cgagagtagg gaactgccag gcatcaaata   1500
aaacgaaagg ctcagtcgaa agactgggcc tttcgtttta tctgttgttt gtcggtgaac   1560
gctctcctga gtaggacaaa tccgccggga gcggatttga acgttgcgaa gcaacggccc   1620
ggagggtggc gggcaggacg cccgccataa actgccaggc atcaaattaa gcagaaggcc   1680
atcctgacgg atggccttt tgcgttctta caaactcttt tgtttatt ttctaaatac   1740 attcaaatat gtatccgctc atgagacaat aaccctgata aatgcttcaa taatattgaa   1800
aaaggaagag tatgagtatt caacatttcc gtgtcgccct tattccctt tttgcggcat   1860 tttgccttcc tgtttttgct cacccagaaa cgctggtgaa agtaaaagat gctgaagatc   1920
agttgggtgc acgagtgggt tacatcgaac tggatctcaa cagcggtaag atccttgaga   1980
gttttcgccc cgaagaacgt tttccaatga tgagcacttt taaagttctg ctatgtggcg   2040
cggtattatc ccgtgttgac gccgggcaag agcaactcgg tcgccgcata cactattctc   2100
agaatgactt ggttgagtac tcaccagtca cagaaaagca tcttacggat ggcatgacag   2160
taagagaatt atgcagtgct gccataacca tgagtgataa cactgcggcc aacttacttc   2220
tgacaacgat cggaggaccg aaggagctaa ccgcttttt gcacaacatg gggatcatg   2280 taactcgcct tgatcgttgg gaaccggagc tgaatgaagc cataccaaac gacgagcgtg   2340
acaccacgat gcctacagca atggcaacaa cgttgcgcaa actattaact ggcgaactac   2400
ttactctagc ttcccggcaa caattaatag actggatgga ggcggataaa gttgcaggac   2460
cacttctgcg ctcggccctt ccggctggct ggtttattgc tgataaatct ggagccggtg   2520
agcgtgggtc tcgcggtatc attgcagcac tggggccaga tggtaagccc tcccgtatcg   2580
tagttatcta cacgacgggg agtcaggcaa ctatggatga acgaaataga cagatcgctg   2640
agataggtgc ctcactgatt aagcattggt aactgtcaga ccaagtttac tcatatatac   2700
tttagattga tttaaaactt catttttaat ttaaaaggat ctaggtgaag atcctttttg   2760
ataatctcat gaccaaaatc ccttaacgtg agttttcgtt ccactgagcg tcagaccccg   2820
tagaaaagat caaaggatct cttgagatc cttttttct gcgcgtaatc tgctgcttgc   2880
aaacaaaaaa accaccgcta ccagcggtgg tttgtttgcc ggatcaagag ctaccaactc   2940 ttttttccgaa ggtaactggc ttcagcagag cgcagatacc aaatactgtc cttctagtgt   3000
agccgtagtt aggccaccac ttcaagaact ctgtagcacc gcctacatac ctcgctctgc   3060
taatcctgtt accagtggct gctgccagtg gcgataagtc gtgtcttacc gggttggact   3120
caagacgata gttaccggat aaggcgcagc ggtcgggctg aacggggggt tcgtgcacac   3180
agcccagctt ggagcgaacg acctacaccg aactgagata cctacagcgt gagctatgag   3240
aaagcgccac gcttcccgaa gggagaaagg cggacaggta tccggtaagc ggcagggtcg   3300
gaacaggaga gcgcacgagg gagcttccag ggggaaacgc ctggtatctt tatagtcctg   3360
tcgggtttcg ccacctctga cttgagcgtc gatttttgtg atgctcgtca ggggggcgga   3420
gcctatggaa aaacgccagc aacgcggcct ttttacggtt cctggccttt tgctggcctt   3480
ttgctcacat gttctttcct gcgttatccc ctgattctgt ggataaccgt attaccgcct   3540
ttgagtgagc tgataccgct cgccgcagcc gaacgaccga gcgcagcgag tcagtgagcg   3600
aggaagcgga agagcgcctg atgcggtatt ttctccttac gcatctgtgc ggtatttcac   3660
accgcatatg gtgcactctc agtacaatct gctctgatgc cgcatagtta agccagtata   3720
cactccgcta tcgctacgtg actgggtcat ggctgcgccc cgacacccgc caacacccgc   3780
tgacgcgccc tgacgggctt gtctgctccc ggcatccgct tacagacaag ctgtgaccgt   3840
```

```
ctccgggagc tgcatgtgtc agaggttttc accgtcatca ccgaaacgcg cgaggcagca    3900
gatcaattcg cgcgcgaagg cgaagcggca tgcatttacg ttgacaccat cgaatggtgc    3960
aaaacctttc gcggtatggc atgatagcgc ccggaagaga gtcaattcag ggtggtgaat    4020
gtgaaaccag taacgttata cgatgtcgca gagtatgccg gtgtctctta tcagaccgtt    4080
tcccgcgtgg tgaaccaggc cagccacgtt tctgcgaaaa cgcgggaaaa agtggaagcg    4140
gcgatggcgg agctgaatta cattcccaac cgcgtggcac aacaactggc gggcaaacag    4200
tcgttgctga ttggcgttgc cacctccagt ctggccctgc acgcgccgtc gcaaattgtc    4260
gcggcgatta atctcgcgc cgatcaactg ggtgccagcg tggtggtgtc gatggtagaa    4320
cgaagcggcg tcgaagcctg taaagcggcg gtgcacaatc ttctcgcgca acgcgtcagt    4380
gggctgatca ttaactatcc gctggatgac caggatgcca ttgctgtgga agctgcctgc    4440
actaatgttc cggcgttatt tcttgatgtc tctgaccaga cacccatcaa cagtattatt    4500
ttctcccatg aagacggtac gcgactgggc gtggagcatc tggtcgcatt gggtcaccag    4560
caaatcgcgc tgttagcggg cccattaagt tctgtctcgg cgcgtctgcg tctggctggc    4620
tggcataaat atctcactcg caatcaaatt cagccgatag cggaacggga aggcgactgg    4680
agtgccatgt ccggttttca acaaaccatg caaatgctga atgagggcat cgttcccact    4740
gcgatgctgg ttgccaacga tcagatggcg ctgggcgcaa tgcgcgccat taccgagtcc    4800
gggctgcgcg ttggtgcgga tatctcggta gtgggatacg acgataccga agacagctca    4860
tgttatatcc cgccgtcaac caccatcaaa caggattttc gcctgctggg gcaaaccagc    4920
gtggaccgct tgctgcaact ctctcagggc caggcggtga agggcaatca gctgttgccc    4980
gtctcactgg tgaaaagaaa aaccaccctg gcgcccaata cgcaaaccgc ctctccccgc    5040
gcgttggccg attcattaat gcagctggca cgacaggttt cccgactgga aagcgggcag    5100
tgagcgcaac gcaattaatg tgagttagcg cgaattgatc tg                      5142
```

<210> SEQ ID NO 8
<211> LENGTH: 3962
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 8

```
catatggttc ctgctatcaa gctcaactcc ggcttcgaca tgccccaggt cggcttcggc      60
ctctggaagg tcgacggctc catcgcttcc gatgtcgtct acaacgctat caaggcaggc     120
taccgcctct tcgatggtgc ctgcgactac ggcaacgagg ttgagtgcgg ccagggtgta     180
gcccgcgcca tcaaggaggg catcgtcaag cgcgaggagc tctttatcgt ctccaagctc     240
tggaacacct tccacgacgg cgaccgcgtc gagcccatcg tccgcaagca gcttgccgac     300
tggggtctcg agtacttcga tctctacctg atccacttcc ccgtcgccct cgagtacgtc     360 gaccctcgg tccgttaccc tcccggctgg cactttgacg caagagcga gatccgcccc      420 tccaaggcca ccatccaaga gacctggacg gccatggagt cgctcgtcga aagggtctc     480 tccaagagca ttggcgtctc caacttccag gcccagctcc tgtacgacct cctccgctac     540
gccaaggtcc gccccgccac tctccagatc gagcaccacc cctacctcgt ccagcagaac     600
ctcctcaacc ttgccaaggc tgagggcatc gccgtgaccg cctactcctc cttcggccct     660
```

```
gcttctttcc gcgagttcaa catggagcac gcccagaagc tccagcctct cctcgaggac    720
cccaccatca aggctattgg tgacaagtac aacaaggatc ctgcccaggt cctcctccgt    780
tgggccaccc agcgcggcct ggccatcatc cccaagtcta gccgcgaggc caccatgaag    840
tccaacctca actctcttga tttcgatctc tccgaggagg acatcaagac catctctggt    900
ttcgaccgcg gcatccgctt caaccagccc accaactact tctccgctga aacctctgg     960 attttcggtt agagatcctc tagagtcgac ctgcaggcat gcaagcttgg ctgttttggc   1020
ggatgagaga agattttcag cctgatacag attaaatcag aacgcagaag cggtctgata   1080
aaacagaatt tgcctggcgg cagtagcgcg gtggtcccac ctgaccccat gccgaactca   1140
gaagtgaaac gccgtagcgc cgatggtagt gtggggtctc cccatgcgag agtagggaac   1200
tgccaggcat caaataaaac gaaaggctca gtcgaaagac tgggcctttc gttttatctg   1260
ttgtttgtcg gtgaacgctc tcctgagtag acaaatccgc cgggagcgg atttgaacgt    1320 tgcgaagcaa cggcccggag ggtggcgggc aggacgcccg ccataaactg ccaggcatca   1380
aattaagcag aaggccatcc tgacggatgg ccttttttgcg tttctacaaa ctcttttttgt 1440 ttatttttct aaatacattc aaatatgtat ccgctcatga gacaataacc ctgataaatg   1500
cttcaataat attgaaaaag gaagagtatg agtattcaac atttccgtgt cgcccttatt   1560
cccttttttg cggcattttg ccttcctgtt tttgctcacc cagaaacgct ggtgaaagta   1620
aaagatgctg aagatcagtt gggtgcacga gtgggttaca tcgaactgga tctcaacagc   1680
ggtaagatcc ttgagagttt tcgccccgaa gaacgttttc caatgatgag cacttttaaa   1740
gttctgctat gtggcgcggt attatcccgt gttgacgccg gcaagagcaa actcggtcgc   1800
cgcatacact attctcagaa tgacttggtt gagtactcac cagtcacaga aaagcatctt   1860
acggatggca tgacagtaag agaattatgc agtgctgcca taaccatgag tgataacact   1920
gcggccaact tacttctgac aacgatcgga ggaccgaagg agctaaccgc ttttttgcac   1980
aacatggggg atcatgtaac tcgccttgat cgttgggaac cggagctgaa tgaagccata   2040
ccaaacgacg agcgtgacac cacgatgcct acagcaatgg caacaacgtt gcgcaaacta   2100
ttaactggcg aactacttac tctagcttcc cggcaacaat taatagactg gatggaggcg   2160
gataaagttg caggaccact tctgcgctcg gcccttccgg ctggctggtt tattgctgat   2220
aaatctggag ccggtgagcg tgggtctcgc ggtatcattg cagcactggg gccagatggt   2280
aagccctccc gtatcgtagt tatctacacg acggggagtc aggcaactat ggatgaacga   2340
aatagacaga tcgctgagat aggtgcctca ctgattaagc attggtaact gtcagaccaa   2400
gtttactcat atatacttta gattgattta aaacttcatt tttaatttaa aaggatctag   2460
gtgaagatcc ttttttgataa tctcatgacc aaaatccctt aacgtgagtt tcgttccac    2520 tgagcgtcag accccgtaga aaagatcaaa ggatcttctt gagatccttt ttttctgcgc   2580
gtaatctgct gcttgcaaac aaaaaaacca ccgctaccag cggtggtttg tttgccggat   2640
caagagctac caactctttt tccgaaggta actggcttca gcagagcgca gataccaaat   2700
actgtccttc tagtgtagcc gtagttaggc caccacttca agaactctgt agcaccgcct   2760
acatacctcg ctctgctaat cctgttacca gtggctgctg ccagtggcga taagtcgtgt   2820
cttaccgggt tggactcaag acgatagtta ccggataagg cgcagcggtc gggctgaacg   2880
gggggttcgt gcacacagcc cagcttggag cgaacgacct acaccgaact gagataccta   2940
cagcgtgagc tatgagaaag cgccacgctt cccgaaggga gaaaggcgga caggtatccg   3000
gtaagcggca gggtcggaac aggagagcgc acgagggagc ttccagggg aaacgcctgg    3060
```

```
tatctttata gtcctgtcgg gtttcgccac ctctgacttg agcgtcgatt tttgtgatgc    3120
tcgtcagggg ggcggagcct atggaaaaac gccagcaacg cggccttttt acggttcctg    3180
gccttttgct ggccttttgc tcacatgttc tttcctgcgt tatcccctga ttctgtggat    3240
aaccgtatta ccgcctttga gtgagctgat accgctcgcc gcagccgaac gaccgagcgc    3300
agcgagtcag tgagcgagga agcggaagag cgcctgatgc ggtattttct ccttacgcat    3360
ctgtgcggta tttcacaccg catatggtgc actctcagta caatctgctc tgatgccgca    3420
tagttaagcc agtatacact ccgctatcgc tacgtgactg ggtcatggct gcgccccgac    3480
acccgccaac cccgctgacg cgccctgacg ggcttgtct gctcccggca tccgcttaca    3540
gacaagctgt gaccgtctcc gggagctgca tgtgtcagag gttttcaccg tcatcaccga    3600
aacgcgcgag gcagcagatc aattcgcgcg cgaaggcgaa gcggcatgca gcgccattca    3660
gagaagaaac caattgtcca tattgcatca gacattgccg tcactgcgtc ttttactggc    3720
tcttctcgct aaccaaaccg gtaaccccgc ttattaaaag cattctgtaa caaagcggga    3780
ccaaggccat gacaaaaacg cgtagcaaaa gtgtctataa tcacggcaga aaagtccaca    3840
ttgattattt gcacggcgtc acactttgct atgccatagc attttatcc ataagattag    3900 cggatcctac ctgacgcttt ttatcgcaac tctctactgt ttctccatac ccgttttttt    3960
gg                                                                     3962

<210> SEQ ID NO 9
<211> LENGTH: 969
<212> TYPE: DNA
<213> ORGANISM: Neurospora crassa

<400> SEQUENCE: 9
atggttcctg ctatcaagct caactccggc ttcgacatgc cccaggtcgg cttcggcctc     60
tggaaggtcg acggctccat cgcttccgat gtcgtctaca cgctatcaa ggcaggctac    120 cgcctcttcg atggtgcctg cgactacggc aacgaggttg agtgcggcca gggtgtagcc    180
cgcgccatca aggagggcat cgtcaagcgc gaggagctct ttatcgtctc caagctctgg    240
aacaccttcc acgacggcga ccgcgtcgag cccatcgtcc gcaagcagct tgccgactgg    300
ggtctcgagt acttcgatct ctacctgatc cactcgcccg tcgccctcga gtacgtcgac    360
ccctcggtcc gttaccctcc cggctggcac tttgacggca gagcgagat ccgcccctcc    420 aaggccacca tccaagagac ctggacggcc atggagtcgc tcgtcgagaa gggtctctcc    480
aagagcattg gcgtctccaa cttccaggcc agctcctgt acgacctcct ccgctacgcc    540
aaggtccgcc ccgccactct ccagatcgag caccacccct acctcgtcca gcagaacctc    600
ctcaaccttg ccaaggctga gggcatcgcc gtgaccgcct actcctcctt cggccctgct    660
tctttccgcg agttcaacat ggagcacgcc cagaagctcc agcctctcct cgaggacccc    720
accatcaagg ctattggtga caagtacaac aaggatcctg cccaggtcct cctccgttgg    780
gccacccagc gcggcctggc catcatcccc aagtctagcc gcgaggccac catgaagtcc    840
aacctcaact ctcttgattt cgatctctcc gaggaggaca tcaagaccat ctctggtttc    900
gaccgcggca tccgcttcaa ccagcccacc aactacttct ccgctgagaa cctctggatt    960
ttcggttag                                                            969

<210> SEQ ID NO 10
<211> LENGTH: 322
<212> TYPE: PRT
```

<213> ORGANISM: Neurospora crassa

<400> SEQUENCE: 10

| Met | Val | Pro | Ala | Ile | Lys | Leu | Asn | Ser | Gly | Phe | Asp | Met | Pro | Gln | Val |
|---|---|---|---|---|---|---|---|---|---|---|---|---|---|---|---|
| 1 | | | | 5 | | | | | 10 | | | | | 15 | |

| Gly | Phe | Gly | Leu | Trp | Lys | Val | Asp | Gly | Ser | Ile | Ala | Ser | Asp | Val | Val |
|---|---|---|---|---|---|---|---|---|---|---|---|---|---|---|---|
| | | | | 20 | | | | | 25 | | | | | 30 | |

| Tyr | Asn | Ala | Ile | Lys | Ala | Gly | Tyr | Arg | Leu | Phe | Asp | Gly | Ala | Cys | Asp |
|---|---|---|---|---|---|---|---|---|---|---|---|---|---|---|---|
| | | | | 35 | | | | | 40 | | | | 45 | | |

| Tyr | Gly | Asn | Glu | Val | Glu | Cys | Gly | Gln | Gly | Val | Ala | Arg | Ala | Ile | Lys |
|---|---|---|---|---|---|---|---|---|---|---|---|---|---|---|---|
| | 50 | | | | | 55 | | | | | 60 | | | | |

| Glu | Gly | Ile | Val | Lys | Arg | Glu | Glu | Leu | Phe | Ile | Val | Ser | Lys | Leu | Trp |
|---|---|---|---|---|---|---|---|---|---|---|---|---|---|---|---|
| 65 | | | | | 70 | | | | | 75 | | | | | 80 |

| Asn | Thr | Phe | His | Asp | Gly | Asp | Arg | Val | Glu | Pro | Ile | Val | Arg | Lys | Gln |
|---|---|---|---|---|---|---|---|---|---|---|---|---|---|---|---|
| | | | | 85 | | | | | 90 | | | | | 95 | |

| Leu | Ala | Asp | Trp | Gly | Leu | Glu | Tyr | Phe | Asp | Leu | Tyr | Leu | Ile | His | Ser |
|---|---|---|---|---|---|---|---|---|---|---|---|---|---|---|---|
| | | | | 100 | | | | | 105 | | | | 110 | | |

| Pro | Val | Ala | Leu | Glu | Tyr | Val | Asp | Pro | Ser | Val | Arg | Tyr | Pro | Pro | Gly |
|---|---|---|---|---|---|---|---|---|---|---|---|---|---|---|---|
| | | | 115 | | | | | 120 | | | | | 125 | | |

| Trp | His | Phe | Asp | Gly | Lys | Ser | Glu | Ile | Arg | Pro | Ser | Lys | Ala | Thr | Ile |
|---|---|---|---|---|---|---|---|---|---|---|---|---|---|---|---|
| | | 130 | | | | | 135 | | | | | 140 | | | |

| Gln | Glu | Thr | Trp | Thr | Ala | Met | Glu | Ser | Leu | Val | Glu | Lys | Gly | Leu | Ser |
|---|---|---|---|---|---|---|---|---|---|---|---|---|---|---|---|
| 145 | | | | | 150 | | | | | 155 | | | | | 160 |

| Lys | Ser | Ile | Gly | Val | Ser | Asn | Phe | Gln | Ala | Gln | Leu | Leu | Tyr | Asp | Leu |
|---|---|---|---|---|---|---|---|---|---|---|---|---|---|---|---|
| | | | | 165 | | | | | 170 | | | | | 175 | |

| Leu | Arg | Tyr | Ala | Lys | Val | Arg | Pro | Ala | Thr | Leu | Gln | Ile | Glu | His | His |
|---|---|---|---|---|---|---|---|---|---|---|---|---|---|---|---|
| | | | 180 | | | | | 185 | | | | | 190 | | |

| Pro | Tyr | Leu | Val | Gln | Gln | Asn | Leu | Leu | Asn | Leu | Ala | Lys | Ala | Glu | Gly |
|---|---|---|---|---|---|---|---|---|---|---|---|---|---|---|---|
| | | | 195 | | | | | 200 | | | | | 205 | | |

| Ile | Ala | Val | Thr | Ala | Tyr | Ser | Ser | Phe | Gly | Pro | Ala | Ser | Phe | Arg | Glu |
|---|---|---|---|---|---|---|---|---|---|---|---|---|---|---|---|
| | | 210 | | | | | 215 | | | | | 220 | | | |

| Phe | Asn | Met | Glu | His | Ala | Gln | Lys | Leu | Gln | Pro | Leu | Leu | Glu | Asp | Pro |
|---|---|---|---|---|---|---|---|---|---|---|---|---|---|---|---|
| 225 | | | | | 230 | | | | | 235 | | | | | 240 |

| Thr | Ile | Lys | Ala | Ile | Gly | Asp | Lys | Tyr | Asn | Lys | Asp | Pro | Ala | Gln | Val |
|---|---|---|---|---|---|---|---|---|---|---|---|---|---|---|---|
| | | | | 245 | | | | | 250 | | | | | 255 | |

| Leu | Leu | Arg | Trp | Ala | Thr | Gln | Arg | Gly | Leu | Ala | Ile | Ile | Pro | Lys | Ser |
|---|---|---|---|---|---|---|---|---|---|---|---|---|---|---|---|
| | | | 260 | | | | | 265 | | | | | 270 | | |

| Ser | Arg | Glu | Ala | Thr | Met | Lys | Ser | Asn | Leu | Asn | Ser | Leu | Asp | Phe | Asp |
|---|---|---|---|---|---|---|---|---|---|---|---|---|---|---|---|
| | | 275 | | | | | 280 | | | | | 285 | | | |

| Leu | Ser | Glu | Glu | Asp | Ile | Lys | Thr | Ile | Ser | Gly | Phe | Asp | Arg | Gly | Ile |
|---|---|---|---|---|---|---|---|---|---|---|---|---|---|---|---|
| | 290 | | | | | 295 | | | | | 300 | | | | |

| Arg | Phe | Asn | Gln | Pro | Thr | Asn | Tyr | Phe | Ser | Ala | Glu | Asn | Leu | Trp | Ile |
|---|---|---|---|---|---|---|---|---|---|---|---|---|---|---|---|
| 305 | | | | | 310 | | | | | 315 | | | | | 320 |

Phe Gly

<210> SEQ ID NO 11
<211> LENGTH: 969
<212> TYPE: DNA
<213> ORGANISM: Neurospora crassa

<400> SEQUENCE: 11

```
atggttcctg ctatcaagct caactccggc ttcgacatgc cccaggtcgg cttcggcctc      60
tggaaggtcg acggctccat cgcttccgat gtcgtctaca acgctatcaa ggcaggctac     120
cgcctcttcg atggtgcctg cgactacggc aacgaggttg agtgcggcca gggtgtagcc     180
```

```
cgcgccatca aggagggcat cgtcaagcgc gaggagctct ttatcgtctc caagctctgg    240
aacaccttcc acgacggcga ccgcgtcgag cccatcgtcc gcaagcagct tgccgactgg    300
ggtctcgagt acttcgatct ctaccagatc cacttccccg tcgccctcga gtacgtcgac    360
ccctcggtcc gttaccctcc cggctggcac tttgacggca agagcgagat ccgcccctcc    420
aaggccacca tccaagagac ctggacggcc atggagtcgc tcgtcgagaa gggtctctcc    480
aagagcattg gcgtctccaa cttccaggcc agctcctgt acgacctcct ccgctacgcc     540
aaggtccgcc ccgccactct ccagatcgag caccacccct acctcgtcca gcagaacctc    600
ctcaaccttg ccaaggctga gggcatcgcc gtgaccgcct actcctcctt cggccctgct    660
tctttccgcg agttcaacat ggagcacgcc cagaagctcc agcctctcct cgaggacccc    720
accatcaagg ctattggtga caagtacaac aaggatcctg cccaggtcct cctccgttgg    780
gccacccagc gcggcctggc catcatcccc aagtctagcc gcgaggccac catgaagtcc    840
aacctcaact ctcttgattt cgatctctcc gaggaggaca tcaagaccat ctctggtttc    900
gaccgcggca tccgcttcaa ccagcccacc aactacttct ccgctgagaa cctctggatt    960
ttcggttag                                                            969
```

<210> SEQ ID NO 12
<211> LENGTH: 322
<212> TYPE: PRT
<213> ORGANISM: Neurospora crassa

<400> SEQUENCE: 12

```
Met Val Pro Ala Ile Lys Leu Asn Ser Gly Phe Asp Met Pro Gln Val
 1               5                  10                  15

Gly Phe Gly Leu Trp Lys Val Asp Gly Ser Ile Ala Ser Asp Val Val
                20                  25                  30

Tyr Asn Ala Ile Lys Ala Gly Tyr Arg Leu Phe Asp Gly Ala Cys Asp
            35                  40                  45

Tyr Gly Asn Glu Val Glu Cys Gly Gln Gly Val Ala Arg Ala Ile Lys
        50                  55                  60

Glu Gly Ile Val Lys Arg Glu Glu Leu Phe Ile Val Ser Lys Leu Trp
65                  70                  75                  80

Asn Thr Phe His Asp Gly Asp Arg Val Glu Pro Ile Val Arg Lys Gln
                85                  90                  95

Leu Ala Asp Trp Gly Leu Glu Tyr Phe Asp Leu Tyr Gln Ile His Phe
            100                 105                 110

Pro Val Ala Leu Glu Tyr Val Asp Pro Ser Val Arg Tyr Pro Pro Gly
        115                 120                 125

Trp His Phe Asp Gly Lys Ser Glu Ile Arg Pro Ser Lys Ala Thr Ile
    130                 135                 140

Gln Glu Thr Trp Thr Ala Met Glu Ser Leu Val Glu Lys Gly Leu Ser
145                 150                 155                 160

Lys Ser Ile Gly Val Ser Asn Phe Gln Ala Gln Leu Leu Tyr Asp Leu
                165                 170                 175

Leu Arg Tyr Ala Lys Val Arg Pro Ala Thr Leu Gln Ile Glu His His
            180                 185                 190

Pro Tyr Leu Val Gln Gln Asn Leu Leu Asn Leu Ala Lys Ala Glu Gly
        195                 200                 205

Ile Ala Val Thr Ala Tyr Ser Ser Phe Gly Pro Ala Ser Phe Arg Glu
    210                 215                 220
```

```
Phe Asn Met Glu His Ala Gln Lys Leu Gln Pro Leu Leu Glu Asp Pro
225                 230                 235                 240

Thr Ile Lys Ala Ile Gly Asp Lys Tyr Asn Lys Asp Pro Ala Gln Val
            245                 250                 255

Leu Leu Arg Trp Ala Thr Gln Arg Gly Leu Ala Ile Ile Pro Lys Ser
        260                 265                 270

Ser Arg Glu Ala Thr Met Lys Ser Asn Leu Asn Ser Leu Asp Phe Asp
    275                 280                 285

Leu Ser Glu Glu Asp Ile Lys Thr Ile Ser Gly Phe Asp Arg Gly Ile
290                 295                 300

Arg Phe Asn Gln Pro Thr Asn Tyr Phe Ser Ala Glu Asn Leu Trp Ile
305                 310                 315                 320

Phe Gly

<210> SEQ ID NO 13
<211> LENGTH: 969
<212> TYPE: DNA
<213> ORGANISM: Neurospora crassa

<400> SEQUENCE: 13
atggttcctg ctatcaagct caactccggc ttcgacatgc cccaggtcgg cttcggcctc      60
tggaaggtcg acggctccat cgcttccgat gtcgtctaca cgctatcaa ggcaggctac     120
cgcctcttcg atggtgcctg cgactacggc aacgaggttg agtgcggcca gggtgtagcc     180
cgcgccatca aggagggcat cgtcaagcgc gaggagctct ttatcgtctc caagctctgg     240
aacaccttcc acgacggcga ccgcgtcgag cccatcgtcc gcaagcagct tgccgactgg     300
ggtctcgagt acttcgatct ctaccagtgc cacttccccg tcgccctcga gtacgtcgac     360
ccctcggtcc gttaccctcc cggctggcac tttgacggca agagcgagat ccgccccctcc    420
aaggccacca tccaagagac ctggacggcc atggagtcgc tcgtcgagaa gggtctctcc     480
aagagcattg cgtctccaa cttccaggcc agctcctgt acgacctcct ccgctacgcc       540
aaggtccgcc ccgccactct ccagatcgag caccacccct acctcgtcca gcagaaccctc    600
ctcaaccttg ccaaggctga gggcatcgcc gtgaccgcct actcctcctt cggccctgct     660
tctttccgcg agttcaacat ggagcacgcc cagaagctcc agcctctcct cgaggacccc     720
accatcaagg ctattggtga caagtacaac aaggatcctg cccaggtcct cctccgttgg     780
gccacccagc gcggcctggc catcatcccc aagtctagcc gcgaggccac catgaagtcc     840
aacctcaact ctcttgattt cgatctctcc gaggaggaca tcaagaccat ctctggtttc     900
gaccgcggca tccgcttcaa ccagcccacc aactacttct ccgctgagaa cctctggatt     960
ttcggttag                                                             969

<210> SEQ ID NO 14
<211> LENGTH: 322
<212> TYPE: PRT
<213> ORGANISM: Neurospora crassa

<400> SEQUENCE: 14

Met Val Pro Ala Ile Lys Leu Asn Ser Gly Phe Asp Met Pro Gln Val
1               5                   10                  15

Gly Phe Gly Leu Trp Lys Val Asp Gly Ser Ile Ala Ser Asp Val Val
            20                  25                  30

Tyr Asn Ala Ile Lys Ala Gly Tyr Arg Leu Phe Asp Gly Ala Cys Asp
        35                  40                  45
```

Tyr Gly Asn Glu Val Glu Cys Gly Gln Gly Val Ala Arg Ala Ile Lys
 50                  55                  60

Glu Gly Ile Val Lys Arg Glu Leu Phe Ile Val Ser Lys Leu Trp
 65                  70                  75                  80

Asn Thr Phe His Asp Gly Asp Arg Val Glu Pro Ile Val Arg Lys Gln
                 85                  90                  95

Leu Ala Asp Trp Gly Leu Glu Tyr Phe Asp Leu Tyr Gln Cys His Phe
                100                 105                 110

Pro Val Ala Leu Glu Tyr Val Asp Pro Ser Val Arg Tyr Pro Pro Gly
                115                 120                 125

Trp His Phe Asp Gly Lys Ser Glu Ile Arg Pro Ser Lys Ala Thr Ile
130                 135                 140

Gln Glu Thr Trp Thr Ala Met Glu Ser Leu Val Glu Lys Gly Leu Ser
145                 150                 155                 160

Lys Ser Ile Gly Val Ser Asn Phe Gln Ala Gln Leu Leu Tyr Asp Leu
                165                 170                 175

Leu Arg Tyr Ala Lys Val Arg Pro Ala Thr Leu Gln Ile Glu His His
                180                 185                 190

Pro Tyr Leu Val Gln Gln Asn Leu Leu Asn Leu Ala Lys Ala Glu Gly
                195                 200                 205

Ile Ala Val Thr Ala Tyr Ser Ser Phe Gly Pro Ala Ser Phe Arg Glu
210                 215                 220

Phe Asn Met Glu His Ala Gln Lys Leu Gln Pro Leu Leu Glu Asp Pro
225                 230                 235                 240

Thr Ile Lys Ala Ile Gly Asp Lys Tyr Asn Lys Asp Pro Ala Gln Val
                245                 250                 255

Leu Leu Arg Trp Ala Thr Gln Arg Gly Leu Ala Ile Ile Pro Lys Ser
                260                 265                 270

Ser Arg Glu Ala Thr Met Lys Ser Asn Leu Asn Ser Leu Asp Phe Asp
                275                 280                 285

Leu Ser Glu Glu Asp Ile Lys Thr Ile Ser Gly Phe Asp Arg Gly Ile
                290                 295                 300

Arg Phe Asn Gln Pro Thr Asn Tyr Phe Ser Ala Glu Asn Leu Trp Ile
305                 310                 315                 320

Phe Gly

<210> SEQ ID NO 15
<211> LENGTH: 969
<212> TYPE: DNA
<213> ORGANISM: Neurospora crassa

<400> SEQUENCE: 15

```
atggttcctg ctatcaagct caactccggc ttcgacatgc cccaggtcgg cttcggcctc     60
tggaaggtcg acggctccat cgcttccgat gtcgtctaca cgctatcaa ggcaggctac    120 cgcctcttcg atggtgcctg cgactacggc aacgaggttg agtgcggcca gggtgtagcc    180
cgcgccatca aggagggcat cgtcaagcgc gaggagctct ttatcgtctc caagctctgg    240
aacaccttcc acgacggcga ccgcgtcgag cccatcgtcc gcaagcagct tgccgactgg    300
ggtctcgagt acttcgatat gtaccagtgc cacttccccg tcgccctcga gtacgtcgac    360
ccctcggtcc gttaccctcc cggctggcac tttgacggca gagcgagat ccgcccctcc    420 aaggccacca tccaagagac ctggacggca atggagtcgc tcgtcgagaa gggtctctcc    480
aagagcattg gcgtctccaa cttccaggcc cagctcctgt acgacctcct ccgctacgcc    540
```

-continued

```
aaggtccgcc ccgccactct ccagatcgag caccacccct acctcgtcca gcagaacctc    600
ctcaaccttg ccaaggctga gggcatcgcc gtgaccgcct actcctcctt cggccctgct    660
tctttccgcg agttcaacat ggagcacgcc cagaagctcc agcctctcct cgaggacccc    720
accatcaagg ctattggtga caagtacaac aaggatcctg cccaggtcct cctccgttgg    780
gccacccagc gcggcctggc catcatcccc aagtctagcc gcgaggccac catgaagtcc    840
aacctcaact tcttgatttt cgatctctcc gaggaggaca tcaagaccat ctctggtttc    900
gaccgcggca tccgcttcaa ccagcccacc aactacttct ccgctgagaa cctctggatt    960
ttcggttag                                                           969
```

<210> SEQ ID NO 16
<211> LENGTH: 322
<212> TYPE: PRT
<213> ORGANISM: Neurospora crassa

<400> SEQUENCE: 16

```
Met Val Pro Ala Ile Lys Leu Asn Ser Gly Phe Asp Met Pro Gln Val
1               5                   10                  15

Gly Phe Gly Leu Trp Lys Val Asp Gly Ser Ile Ala Ser Asp Val Val
            20                  25                  30

Tyr Asn Ala Ile Lys Ala Gly Tyr Arg Leu Phe Asp Gly Ala Cys Asp
        35                  40                  45

Tyr Gly Asn Glu Val Glu Cys Gly Gln Gly Val Ala Arg Ala Ile Lys
    50                  55                  60

Glu Gly Ile Val Lys Arg Glu Glu Leu Phe Ile Val Ser Lys Leu Trp
65                  70                  75                  80

Asn Thr Phe His Asp Gly Asp Arg Val Glu Pro Ile Val Arg Lys Gln
                85                  90                  95

Leu Ala Asp Trp Gly Leu Glu Tyr Phe Asp Met Tyr Gln Cys His Phe
            100                 105                 110

Pro Val Ala Leu Glu Tyr Val Asp Pro Ser Val Arg Tyr Pro Pro Gly
        115                 120                 125

Trp His Phe Asp Gly Lys Ser Glu Ile Arg Pro Ser Lys Ala Thr Ile
    130                 135                 140

Gln Glu Thr Trp Thr Ala Met Glu Ser Leu Val Glu Lys Gly Leu Ser
145                 150                 155                 160

Lys Ser Ile Gly Val Ser Asn Phe Gln Ala Gln Leu Leu Tyr Asp Leu
                165                 170                 175

Leu Arg Tyr Ala Lys Val Arg Pro Ala Thr Leu Gln Ile Glu His His
            180                 185                 190

Pro Tyr Leu Val Gln Gln Asn Leu Leu Asn Leu Ala Lys Ala Glu Gly
        195                 200                 205

Ile Ala Val Thr Ala Tyr Ser Ser Phe Gly Pro Ala Ser Phe Arg Glu
    210                 215                 220

Phe Asn Met Glu His Ala Gln Lys Leu Gln Pro Leu Leu Glu Asp Pro
225                 230                 235                 240

Thr Ile Lys Ala Ile Gly Asp Lys Tyr Asn Lys Asp Pro Ala Gln Val
                245                 250                 255

Leu Leu Arg Trp Ala Thr Gln Arg Gly Leu Ala Ile Ile Pro Lys Ser
            260                 265                 270

Ser Arg Glu Ala Thr Met Lys Ser Asn Leu Asn Ser Leu Asp Phe Asp
        275                 280                 285

Leu Ser Glu Glu Asp Ile Lys Thr Ile Ser Gly Phe Asp Arg Gly Ile
```

```
                290                 295                 300
Arg Phe Asn Gln Pro Thr Asn Tyr Phe Ser Ala Glu Asn Leu Trp Ile
305                 310                 315                 320

Phe Gly
```

<210> SEQ ID NO 17
<211> LENGTH: 969
<212> TYPE: DNA
<213> ORGANISM: Neurospora crassa

<400> SEQUENCE: 17

```
atggttcctg ctatcaagct caactccggc ttcgacatgc cccaggtcgg cttcggcctc      60
tggaaggtcg acggctccat cgcttccgat gtcgtctaca acgctatcaa ggcaggctac     120
cgcctcttcg atggtgcctg cgactacggc aacgaggttg agtgcggcca gggtgtagcc     180
cgcgccatca aggagggcat cgtcaagcgc gaggagctct ttatcgtctc caagctctgg     240
aacaccttcc acgacggcga ccgcgtcgag cccatcgtcc gcaagcagct tgccgactgg     300
ggtctcgagt acttcgatat gtaccagtgc cacttcccca tcgccctcga gtacgtcgac     360
ccctcggtcc gttaccctcc cggctggcac tttgacggca agagcgagat ccgcccctcc     420
aaggccacca tccaagagac ctggacggcc atggagtcgc tcgtcgagaa gggtctctcc     480
aagagcattg gcgtctccaa cttccaggcc agctcctgt acgacctcct ccgctacgcc      540
aaggtccgcc ccgccactct ccagatcgag caccacccct acctcgtcca gcagaacctc     600
ctcaaccttg ccaaggctga ggcatcgcc gtgaccgcct actcctcctt cggccctgct      660
tctttccgcg agttcaacat ggagcacgcc agaagctcc agcctctcct cgaggacccc      720
accatcaagg ctattggtga caagtacaac aaggatcctg cccaggtcct cctccgttgg     780
gccacccagc gcggcctggc catcatcccc aagtctagcc gcgaggccac catgaagtcc     840
aacctcaact ctcttgattt cgatctctcc gaggaggaca tcaagaccat ctctggtttc     900
gaccgcggca tccgcttcaa ccagcccacc aactacttct ccgctgagaa cctctggatt     960
ttcggttag                                                             969
```

<210> SEQ ID NO 18
<211> LENGTH: 322
<212> TYPE: PRT
<213> ORGANISM: Neurospora crassa

<400> SEQUENCE: 18

```
Met Val Pro Ala Ile Lys Leu Asn Ser Gly Phe Asp Met Pro Gln Val
1               5                   10                  15

Gly Phe Gly Leu Trp Lys Val Asp Gly Ser Ile Ala Ser Asp Val Val
                20                  25                  30

Tyr Asn Ala Ile Lys Ala Gly Tyr Arg Leu Phe Asp Gly Ala Cys Asp
            35                  40                  45

Tyr Gly Asn Glu Val Glu Cys Gly Gln Gly Val Ala Arg Ala Ile Lys
        50                  55                  60

Glu Gly Ile Val Lys Arg Glu Glu Leu Phe Ile Val Ser Lys Leu Trp
65                  70                  75                  80

Asn Thr Phe His Asp Gly Asp Arg Val Glu Pro Ile Val Arg Lys Gln
                85                  90                  95

Leu Ala Asp Trp Gly Leu Glu Tyr Phe Asp Met Tyr Gln Cys His Phe
            100                 105                 110

Pro Ile Ala Leu Glu Tyr Val Asp Pro Ser Val Arg Tyr Pro Pro Gly
```

```
            115                 120                 125
Trp His Phe Asp Gly Lys Ser Glu Ile Arg Pro Ser Lys Ala Thr Ile
    130                 135                 140

Gln Glu Thr Trp Thr Ala Met Glu Ser Leu Val Glu Lys Gly Leu Ser
145                 150                 155                 160

Lys Ser Ile Gly Val Ser Asn Phe Gln Ala Gln Leu Leu Tyr Asp Leu
                165                 170                 175

Leu Arg Tyr Ala Lys Val Arg Pro Ala Thr Leu Gln Ile Glu His His
            180                 185                 190

Pro Tyr Leu Val Gln Gln Asn Leu Leu Asn Leu Ala Lys Ala Glu Gly
        195                 200                 205

Ile Ala Val Thr Ala Tyr Ser Ser Phe Gly Pro Ala Ser Phe Arg Glu
    210                 215                 220

Phe Asn Met Glu His Ala Gln Lys Leu Gln Pro Leu Leu Glu Asp Pro
225                 230                 235                 240

Thr Ile Lys Ala Ile Gly Asp Lys Tyr Asn Lys Asp Pro Ala Gln Val
                245                 250                 255

Leu Leu Arg Trp Ala Thr Gln Arg Gly Leu Ala Ile Ile Pro Lys Ser
            260                 265                 270

Ser Arg Glu Ala Thr Met Lys Ser Asn Leu Asn Ser Leu Asp Phe Asp
        275                 280                 285

Leu Ser Glu Glu Asp Ile Lys Thr Ile Ser Gly Phe Asp Arg Gly Ile
    290                 295                 300

Arg Phe Asn Gln Pro Thr Asn Tyr Phe Ser Ala Glu Asn Leu Trp Ile
305                 310                 315                 320

Phe Gly
```

<210> SEQ ID NO 19
<211> LENGTH: 969
<212> TYPE: DNA
<213> ORGANISM: Neurospora crassa

<400> SEQUENCE: 19

```
atggttcctg ctatcaagct caactccggc ttcgacatgc cccaggtcgg cttcggcctc    60
tggaaggtcg acggctccat cgcttccgat gtcgtctaca cgctatcaa ggcaggctac   120
cgcctcttcg atggtgcctg cgactacggc aacgaggttg agtgcggcca gggtgtagcc   180
cgcgccatca aggagggcat cgtcaagcgc gaggagctct ttatcgtctc caagctctgg   240
aacaccttcc acgacggcga ccgcgtcgag cccatcgtcc gcaagcagct tgccgactgg   300
ggtgtggagt acttcgatat gtaccagtgc cacttcccca tcgccctcga gtacgtcgac   360
ccctcggtcc gttaccctcc cggctggcac tttgacggca agagcgagat ccgcccctcc   420
aaggccacca tccaagagac ctggacggcc atggagtcgc tcgtcgagaa gggtctctcc   480
aagagcattg gcgtctccaa cttccaggcc cagctcctgt acgacctcct ccgctacgcc   540
aaggtccgcc ccgccactct ccagatcgag caccacccct acctcgtcca gcagaacctc   600
ctcaaccttg ccaaggctga gggcatcgcc gtgaccgcct actcctcctt cggccctgct   660
tctttccgcg agttcaacat ggagcacgcc cagaagctcc agcctctcct cgaggacccc   720
accatcaagg ctattggtga caagtacaac aaggatcctg cccaggtcct cctccgttgg   780
gccacccagc gcggcctggc catcatcccc aagtctagcc gcgaggccac catgaagtcc   840
aacctcaact ctcttgattt cgatctctcc gaggaggaca tcaagaccat ctctggtttc   900
gaccgcggca tccgcttcaa ccagcccacc aactacttct ccgccgagaa cctctggatt   960
``` ttcggttag                                                                                              969

<210> SEQ ID NO 20
<211> LENGTH: 322
<212> TYPE: PRT
<213> ORGANISM: Neurospora crassa

<400> SEQUENCE: 20

Met Val Pro Ala Ile Lys Leu Asn Ser Gly Phe Asp Met Pro Gln Val
1               5                   10                  15

Gly Phe Gly Leu Trp Lys Val Asp Gly Ser Ile Ala Ser Asp Val Val
            20                  25                  30

Tyr Asn Ala Ile Lys Ala Gly Tyr Arg Leu Phe Asp Gly Ala Cys Asp
        35                  40                  45

Tyr Gly Asn Glu Val Glu Cys Gly Gln Gly Val Ala Arg Ala Ile Lys
    50                  55                  60

Glu Gly Ile Val Lys Arg Glu Glu Leu Phe Ile Val Ser Lys Leu Trp
65                  70                  75                  80

Asn Thr Phe His Asp Gly Asp Arg Val Glu Pro Ile Val Arg Lys Gln
                85                  90                  95

Leu Ala Asp Trp Gly Val Glu Tyr Phe Asp Met Tyr Gln Cys His Phe
            100                 105                 110

Pro Ile Ala Leu Glu Tyr Val Asp Pro Ser Val Arg Tyr Pro Pro Gly
        115                 120                 125

Trp His Phe Asp Gly Lys Ser Glu Ile Arg Pro Ser Lys Ala Thr Ile
    130                 135                 140

Gln Glu Thr Trp Thr Ala Met Glu Ser Leu Val Glu Lys Gly Leu Ser
145                 150                 155                 160

Lys Ser Ile Gly Val Ser Asn Phe Gln Ala Gln Leu Leu Tyr Asp Leu
                165                 170                 175

Leu Arg Tyr Ala Lys Val Arg Pro Ala Thr Leu Gln Ile Glu His His
            180                 185                 190

Pro Tyr Leu Val Gln Gln Asn Leu Leu Asn Leu Ala Lys Ala Glu Gly
        195                 200                 205

Ile Ala Val Thr Ala Tyr Ser Ser Phe Gly Pro Ala Ser Phe Arg Glu
    210                 215                 220

Phe Asn Met Glu His Ala Gln Lys Leu Gln Pro Leu Leu Glu Asp Pro
225                 230                 235                 240

Thr Ile Lys Ala Ile Gly Asp Lys Tyr Asn Lys Asp Pro Ala Gln Val
                245                 250                 255

Leu Leu Arg Trp Ala Thr Gln Arg Gly Leu Ala Ile Ile Pro Lys Ser
            260                 265                 270

Ser Arg Glu Ala Thr Met Lys Ser Asn Leu Asn Ser Leu Asp Phe Asp
        275                 280                 285

Leu Ser Glu Glu Asp Ile Lys Thr Ile Ser Gly Phe Asp Arg Gly Ile
    290                 295                 300

Arg Phe Asn Gln Pro Thr Asn Tyr Phe Ser Ala Glu Asn Leu Trp Ile
305                 310                 315                 320

Phe Gly

<210> SEQ ID NO 21
<211> LENGTH: 5842
<212> TYPE: DNA
<213> ORGANISM: Artificial Sequence
<220> FEATURE:

<221> NAME/KEY: source
<223> OTHER INFORMATION: /note="Description of Artificial Sequence: Synthetic polynucleotide"

<400> SEQUENCE: 21

```
ggggaattgt gagcggataa caattcccct gtagaaataa ttttgtttaa ctttaataag      60
gagatatacc atgtctgtta ctggtgatca ccctgtggct gtgtaattcg aaacggctga     120
agcgggagta aaaagtcagc acgccgaaat ggcgcggcgt gctggacagg aagattacag     180
cgtagcagtt tgttgtgttt tcttcgtttc cggttcccag agcgcttcca gctcctcaag     240
ggttttacct ttggtttccg ggacaaattt ccacataaac agtgctgcca gaacgcccat     300
acaaccgtaa atccagtagg agaaaccgtt gtggaaatgg gccaccagcc aggagttttt     360
gtccatcatc gggaaggtcc aggagacgaa gtagttcgcc agccactggg ccgccaccgc     420
gattgccagc gctttaccac gaatagcatt cgggaagatt ccgacagca gtacccagca     480
taccggaccc caggacatgg caaggcggc aacatagaac agcatcgaca gtagcgccac     540
aatacccggt gcctgagtgt aaaacgcggt accgaggcta acataccga ttgccattcc     600
gagtgcgccg ataatttgca gtggcttacg accaaattta tccaccgtca taattgccag     660
aacggtgaag gtgaggttga taactccgac aataatggtc tgcaacagcg cgatatccgt     720
gctggccccc agcgttttga acacttccgg cgcgtagtac agcaccacat tgatgccgac     780
aaattgctgg aagatggaga gcattacgcc gattacaatc acgcccacgc aaacatcag     840
cagacgacca ccggttttgc ggccatgatc cagggagtgt ttaatttcct gtactgcctg     900
agttgcaagc gtgttgccca taattttgcg caggatacct tccgcctgtt cttgcttgcc     960
gcgcgacatc agccagcgag actttctgg cacggtatac agcagcatta agaacagcag    1020
tgcagggata cattccgagg caaacatata acgccagccg tcagtattca gccagctggc    1080
atcaccggaa cggcaataa aatagtttac gcagtaaact aaaagttgcc gaaaataat    1140
cgcaaactgg ttaaaagaga ccagtttccc gcgaatatga gctggagcca gttccgcaat    1200
atacattggc gagagcattg aggctaaacc aacgccaata ccgccaataa tgcgataaat    1260
aacaaattcc gggacataac ctgccagata acaggcaca gtgttgtccg ggtttataga    1320
ggtaaaacca agttctggcc aggcagaacc tacaccagaa ataaaaaaca ggacagcagc    1380
aatcttaagt gaatcacgac gaccgaagcg gttactgcaa taaccaccga gggcaccgcc    1440
gatgatgcaa ccaatcagag cgctggccac gcaaaacct aacagggagt tggcagcgga    1500
ttcacttaag ttttgtggag caacaaagac ggtattgagt gactcaacag taccggaaat    1560
aacggcggtg tcgtagccaa ataataaacc acctaatgta gcgactaagg taatcgaaaa    1620
tatataactg gaattatact gggtattcat atgccaaaaa aacgggtatg gagaaacagt    1680
agagagttgc gataaaaagc gtcaggtagg atccgctaat cttatggata aaaatgctat    1740
ggcatagcaa agtgtgacgc cgtgcaaata atcaatgtgg acttttctgc cgtgattata    1800
gacactttg ctacgcgttt ttgtcatggc cttggtcccg ctttgttaca gaatgctttt    1860
aataagcggg gttaccggtt tggttagcga gaagagccag taaaagacgc agtgacggca    1920
atgtctgatg caatatggac aattggtttc ttctctgaat ggcgctgcag gtcgacaagc    1980
ttgcggccgc ataatgctta agtcgaacag aaagtaatcg tattgtacac ggccgcataa    2040
tcgaaattaa tacgactcac tatagggaa ttgtgagcgg ataacaattc cccatcttag    2100
tatattagtt aagtataaga aggagatata catatgcag atctcaattg gatatcggcc    2160
ggccacgcga tcgctgacgt cggtaccctc gagtctggta agaaaccgc tgctgcgaaa    2220
```

| | |
|---|---|
| tttgaacgcc agcacatgga ctcgtctact agcgcagctt aattaaccta ggctgctgcc | 2280 |
| accgctgagc aataactagc ataacccctt ggggcctcta acgggtctt gagggttt | 2340 |
| ttgctgaaac ctcaggcatt tgagaagcac acggtcacac tgcttccggt agtcaataaa | 2400 |
| ccggtaaacc agcaatagac ataagcggct atttaacgac cctgccctga accgacgacc | 2460 |
| gggtcgaatt tgctttcgaa tttctgccat tcatccgctt attatcactt attcaggcgt | 2520 |
| agcaccaggc gtttaagggc accaataact gccttaaaaa aattacgccc cgccctgcca | 2580 |
| ctcatcgcag tactgttgta attcattaag cattctgccg acatggaagc catcacagac | 2640 |
| ggcatgatga acctgaatcg ccagcggcat cagcaccttg tcgccttgcg tataatattt | 2700 |
| gcccatagtg aaaacggggg cgaagaagtt gtccatattg gccacgttta aatcaaaact | 2760 |
| ggtgaaactc acccagggat tggctgagac gaaaaacata ttctcaataa acccttagg | 2820 |
| gaaataggcc aggttttcac cgtaacacgc cacatcttgc gaatatatgt gtagaaactg | 2880 |
| ccggaaatcg tcgtggtatt cactccagag cgatgaaaac gtttcagttt gctcatggaa | 2940 |
| aacggtgtaa caagggtgaa cactatccca tatcaccagc tcaccgtctt tcattgccat | 3000 |
| acggaactcc ggatgagcat tcatcaggcg ggcaagaatg tgaataaagg ccggataaaa | 3060 |
| cttgtgctta ttttctttta cggtctttaa aaaggccgta atatccagct gaacggtctg | 3120 |
| gttataggta cattgagcaa ctgactgaaa tgcctcaaaa tgttctttac gatgccattg | 3180 |
| ggatatatca acggtggtat atccagtgat ttttttctcc attttagctt ccttagctcc | 3240 |
| tgaaaatctc gataactcaa aaaatacgcc cggtagtgat cttatttcat tatggtgaaa | 3300 |
| gttggaacct cttacgtgcc gatcaacgtc tcattttcgc caaaagttgg cccagggctt | 3360 |
| cccggtatca acaggggacac caggatttat ttattctgcg aagtgatctt ccgtcacagg | 3420 |
| tatttattcg gcgcaaagtg cgtcgggtga tgctgccaac ttactgattt agtgtatgat | 3480 |
| ggtgttttg aggtgctcca gtggcttctg tttctatcag ctgtccctcc tgttcagcta | 3540 |
| ctgacggggt ggtgcgtaac ggcaaaagca ccgccggaca tcagcgctag cggagtgtat | 3600 |
| actggcttac tatgttggca ctgatgaggg tgtcagtgaa gtgcttcatg tggcaggaga | 3660 |
| aaaaaggctg caccggtgcg tcagcagaat atgtgataca ggatatattc cgcttcctcg | 3720 |
| ctcactgact cgctacgctc ggtcgttcga ctgcggcgag cggaaatggc ttacgaacgg | 3780 |
| gcggagatt tcctggaaga tgccaggaag atacttaaca gggaagtgag agggccgcgg | 3840 |
| caaagccgtt tttccatagg ctccgccccc ctgacaagca tcacgaaatc tgacgctcaa | 3900 |
| atcagtggtg gcgaaacccg acaggactat aaagatacca ggcgtttccc ctggcggctc | 3960 |
| cctcgtgcgc tctcctgttc ctgcctttcg gtttaccggt gtcattccgc tgttatggcc | 4020 |
| gcgtttgtct cattccacgc ctgacactca gttccgggta ggcagttcgc tccaagctgg | 4080 |
| actgtatgca cgaaccccc gttcagtccg accgctgcgc cttatccggt aactatcgtc | 4140 |
| ttgagtccaa cccggaaaga catgcaaaag caccactggc agcagccact ggtaattgat | 4200 |
| ttagaggagt tagtcttgaa gtcatgcgcc ggttaaggct aaactgaaag gacaagtttt | 4260 |
| ggtgactgcg ctcctccaag ccagttacct cggttcaaag agttggtagc tcagagaacc | 4320 |
| ttcgaaaaac cgccctgcaa ggcggttttt tcgttttcag agcaagagat tacgcgcaga | 4380 |
| ccaaaacgat ctcaagaaga tcatcttatt aatcagataa aatatttcta gatttcagtg | 4440 |
| caatttatct cttcaaatgt agcacctgaa gtcagcccca tacgatataa gttgtaattc | 4500 |
| tcatgttagt catgccccgc gcccaccgga aggagctgac tgggttgaag ctctcaagg | 4560 |

```
gcatcggtcg agatcccggt gcctaatgag tgagctaact tacattaatt gcgttgcgct    4620
cactgcccgc tttccagtcg ggaaacctgt cgtgccagct gcattaatga atcggccaac    4680
gcgcggggag aggcggtttg cgtattgggc gccagggtgg ttttcttttt caccagtgag    4740
acgggcaaca gctgattgcc cttcaccgcc tggccctgag agagttgcag caagcggtcc    4800
acgctggttt gccccagcag gcgaaaatcc tgtttgatgg tggttaacgg cgggatataa    4860
catgagctgt cttcggtatc gtcgtatccc actaccgaga tgtccgcacc aacgcgcagc    4920
ccggactcgg taatggcgcg cattgcgccc agcgccatct gatcgttggc aaccagcatc    4980
gcagtgggaa cgatgccctc attcagcatt tgcatggttt gttgaaaacc ggacatggca    5040
ctccagtcgc cttcccgttc cgctatcggc tgaatttgat tgcgagtgag atatttatgc    5100
cagccagcca gacgcagacg cgccgagaca gaacttaatg ggcccgctaa cagcgcgatt    5160
tgctggtgac ccaatgcgac cagatgctcc acgcccagtc gcgtaccgtc ttcatgggag    5220
aaaataatac tgttgatggg tgtctggtca gagacatcaa gaaataacgc cggaacatta    5280
gtgcaggcag cttccacagc aatggcatcc tggtcatcca gcggatagtt aatgatcagc    5340
ccactgacgc gttgcgcgag aagattgtgc accgccgctt tacaggcttc gacgccgctt    5400
cgttctacca tcgacaccac cacgctggca cccagttgat cggcgcgaga tttaatcgcc    5460
gcgacaattt gcgacggcgc gtgcagggcc agactggagg tggcaacgcc aatcagcaac    5520
gactgtttgc ccgccagttg ttgtgccacg cggttgggaa tgtaattcag ctccgccatc    5580
gccgcttcca cttttcccg cgttttcgca gaaacgtggc tggcctggtt caccacgcgg    5640
gaaacggtct gataagagac accggcatac tctgcgacat cgtataacgt tactggtttc    5700
acattcacca ccctgaattg actctcttcc gggcgctatc atgccatacc gcgaaaggtt    5760
ttgcgccatt cgatggtgtc cgggatctcg acgctctccc ttatgcgact cctgcattag    5820
gaaattaata cgactcacta ta                                            5842
```